(12) United States Patent
Brzezicki et al.

(10) Patent No.: US 9,047,559 B2
(45) Date of Patent: Jun. 2, 2015

(54) COMPUTER-IMPLEMENTED SYSTEMS AND METHODS FOR TESTING LARGE SCALE AUTOMATIC FORECAST COMBINATIONS

(75) Inventors: Jerzy Michal Brzezicki, Cary, NC (US); Dinesh P. Apte, Pune (IN); Michael J. Leonard, Cary, NC (US); Michael Ryan Chipley, Raleigh, NC (US); Sagar Arun Mainkar, Pune (IN); Edward Tilden Blair, Cary, NC (US)

(73) Assignee: SAS Institute Inc., Cary, NC (US)

( * ) Notice: Subject to any disclaimer, the term of this patent is extended or adjusted under 35 U.S.C. 154(b) by 169 days.

(21) Appl. No.: 13/440,045

(22) Filed: Apr. 5, 2012

(65) Prior Publication Data

US 2013/0024173 A1 Jan. 24, 2013

Related U.S. Application Data

(63) Continuation-in-part of application No. 13/189,131, filed on Jul. 22, 2011.

(60) Provisional application No. 61/594,442, filed on Feb. 3, 2012.

(51) Int. Cl.
| | |
|---|---|
| *G06F 7/60* | (2006.01) |
| *G06F 17/10* | (2006.01) |
| *G06G 7/48* | (2006.01) |
| *G06N 7/00* | (2006.01) |
| *G06F 17/18* | (2006.01) |

(Continued)

(52) U.S. Cl.
CPC ............... *G06N 7/005* (2013.01); *G06F 17/18* (2013.01); *G06F 17/5009* (2013.01); *G06F 19/24* (2013.01); *G06F 2217/10* (2013.01)

(58) Field of Classification Search
CPC . G06F 17/5009; G06F 19/24; G06F 2217/10; G06F 17/18; G06N 7/005
USPC .......................................................... 703/2, 6
See application file for complete search history.

(56) References Cited

U.S. PATENT DOCUMENTS

| | | |
|---|---|---|
| 5,461,699 A | 10/1995 | Arbabi et al. |
| 5,615,109 A | 3/1997 | Eder |

(Continued)

FOREIGN PATENT DOCUMENTS

WO 2005/124718 A2 12/2005

OTHER PUBLICATIONS

Yu Lean, NPL, "Time series forecasting with multiple candidate models: selecting or combining?", Jan. 2005.*

(Continued)

*Primary Examiner* — Omar Fernandez Rivas
*Assistant Examiner* — Angel Calle
(74) *Attorney, Agent, or Firm* — Kilpatrick Townsend & Stockton, LLP

(57) ABSTRACT

Systems and methods are provided for evaluating performance of forecasting models. A plurality of forecasting models may be generated using a set of in-sample data. Two or more forecasting models from the plurality of forecasting models may be selected for use in generating a combined forecast. An ex-ante combined forecast may be generated for an out-of-sample period using the selected two or more forecasting models. The ex-ante combined forecast may then be compared with a set of actual out-of-sample data to evaluate performance of the combined forecast.

24 Claims, 42 Drawing Sheets

(51) Int. Cl.
*G06F 17/50* (2006.01)
*G06F 19/24* (2011.01)

(56) References Cited

U.S. PATENT DOCUMENTS

| | | |
|---|---|---|
| 5,870,746 A | 2/1999 | Knutson et al. |
| 5,918,232 A | 6/1999 | Pouschine et al. |
| 5,953,707 A | 9/1999 | Huang et al. |
| 5,991,740 A | 11/1999 | Messer |
| 5,995,943 A | 11/1999 | Bull et al. |
| 6,052,481 A | 4/2000 | Grajski et al. |
| 6,128,624 A | 10/2000 | Papierniak et al. |
| 6,151,584 A | 11/2000 | Papierniak et al. |
| 6,169,534 B1 | 1/2001 | Raffel et al. |
| 6,189,029 B1 | 2/2001 | Fuerst |
| 6,208,975 B1 | 3/2001 | Bull et al. |
| 6,216,129 B1 | 4/2001 | Eldering |
| 6,223,173 B1 | 4/2001 | Wakio et al. |
| 6,230,064 B1 | 5/2001 | Nakase et al. |
| 6,286,005 B1 | 9/2001 | Cannon |
| 6,308,162 B1 | 10/2001 | Ouimet et al. |
| 6,317,731 B1 | 11/2001 | Luciano |
| 6,334,110 B1 | 12/2001 | Walter et al. |
| 6,356,842 B1 | 3/2002 | Intriligator et al. |
| 6,397,166 B1 | 5/2002 | Leung et al. |
| 6,400,853 B1 | 6/2002 | Shiiyama |
| 6,526,405 B1 | 2/2003 | Mannila et al. |
| 6,539,392 B1 | 3/2003 | Rebane |
| 6,542,869 B1 | 4/2003 | Foote |
| 6,564,190 B1 | 5/2003 | Dubner |
| 6,591,255 B1 | 7/2003 | Tatum et al. |
| 6,611,726 B1 | 8/2003 | Crosswhite |
| 6,640,227 B1 | 10/2003 | Andreev |
| 6,735,738 B1 | 5/2004 | Kojima |
| 6,775,646 B1 | 8/2004 | Tufillaro et al. |
| 6,792,399 B1 | 9/2004 | Phillips et al. |
| 6,850,871 B1 | 2/2005 | Barford et al. |
| 6,876,988 B2 | 4/2005 | Helsper et al. |
| 6,878,891 B1 | 4/2005 | Josten et al. |
| 6,928,398 B1 | 8/2005 | Fang et al. |
| 6,978,249 B1 | 12/2005 | Beyer et al. |
| 7,072,863 B1 | 7/2006 | Phillips et al. |
| 7,080,026 B2 | 7/2006 | Singh et al. |
| 7,103,222 B2 | 9/2006 | Peker |
| 7,130,822 B1 | 10/2006 | Their et al. |
| 7,130,833 B2 | 10/2006 | Kashima et al. |
| 7,171,340 B2 | 1/2007 | Brocklebank |
| 7,194,434 B2 | 3/2007 | Piccioli |
| 7,216,088 B1 | 5/2007 | Chappel et al. |
| 7,222,082 B1 | 5/2007 | Adhikari et al. |
| 7,236,940 B2 | 6/2007 | Chappel |
| 7,240,019 B2 | 7/2007 | Delurgio et al. |
| 7,251,589 B1 | 7/2007 | Crowe et al. |
| 7,260,550 B1 | 8/2007 | Notani |
| 7,280,986 B2 | 10/2007 | Goldberg et al. |
| 7,433,834 B2 | 10/2008 | Joao |
| 7,523,048 B1 | 4/2009 | Dvorak |
| 7,530,025 B2 | 5/2009 | Ramarajan et al. |
| 7,565,417 B2 | 7/2009 | Rowady, Jr. |
| 7,570,262 B2 | 8/2009 | Landau et al. |
| 7,610,214 B1 | 10/2009 | Dwarakanath et al. |
| 7,617,167 B2 | 11/2009 | Griffis et al. |
| 7,660,734 B1 | 2/2010 | Neal et al. |
| 7,689,456 B2 | 3/2010 | Schroeder et al. |
| 7,693,737 B2 | 4/2010 | Their et al. |
| 7,702,482 B2 | 4/2010 | Graepel et al. |
| 7,711,734 B2 | 5/2010 | Leonard et al. |
| 7,716,022 B1 | 5/2010 | Park et al. |
| 8,005,707 B1 | 8/2011 | Jackson et al. |
| 8,010,324 B1 | 8/2011 | Crowe et al. |
| 8,010,404 B1 | 8/2011 | Wu et al. |
| 8,326,677 B1 | 12/2012 | Fan et al. |
| 2002/0169657 A1 | 11/2002 | Singh et al. |
| 2003/0101009 A1 | 5/2003 | Seem |
| 2003/0105660 A1 | 6/2003 | Walsh et al. |
| 2003/0110016 A1 | 6/2003 | Stefek et al. |
| 2003/0154144 A1 | 8/2003 | Pokorny et al. |
| 2003/0187719 A1 | 10/2003 | Brocklebank |
| 2003/0200134 A1 | 10/2003 | Leonard et al. |
| 2003/0212590 A1 | 11/2003 | Klingler |
| 2004/0041727 A1 | 3/2004 | Ishii et al. |
| 2004/0172225 A1 | 9/2004 | Hochberg et al. |
| 2005/0055275 A1 | 3/2005 | Newman et al. |
| 2005/0102107 A1 | 5/2005 | Porikli |
| 2005/0114391 A1 | 5/2005 | Corcoran et al. |
| 2005/0159997 A1 | 7/2005 | John |
| 2005/0177351 A1 | 8/2005 | Goldberg et al. |
| 2005/0209732 A1 | 9/2005 | Audimoolam et al. |
| 2005/0249412 A1 | 11/2005 | Radhakrishnan et al. |
| 2005/0271156 A1 | 12/2005 | Nakano |
| 2006/0063156 A1 | 3/2006 | Willman et al. |
| 2006/0064181 A1 | 3/2006 | Kato |
| 2006/0085380 A1 | 4/2006 | Cote et al. |
| 2006/0112028 A1 | 5/2006 | Xiao et al. |
| 2006/0143081 A1 | 6/2006 | Argaiz |
| 2006/0164997 A1 | 7/2006 | Graepel et al. |
| 2006/0241923 A1 | 10/2006 | Xu et al. |
| 2006/0247900 A1 | 11/2006 | Brocklebank |
| 2007/0011175 A1 | 1/2007 | Langseth et al. |
| 2007/0094168 A1 | 4/2007 | Ayala et al. |
| 2007/0106550 A1 | 5/2007 | Umblijs et al. |
| 2007/0118491 A1 | 5/2007 | Baum et al. |
| 2007/0162301 A1 | 7/2007 | Sussman et al. |
| 2007/0203783 A1 | 8/2007 | Beltramo |
| 2007/0208492 A1 | 9/2007 | Downs et al. |
| 2007/0208608 A1 | 9/2007 | Amerasinghe et al. |
| 2007/0291958 A1 | 12/2007 | Jehan |
| 2008/0208832 A1 | 8/2008 | Friedlander et al. |
| 2008/0288537 A1 | 11/2008 | Golovchinsky et al. |
| 2008/0294651 A1 | 11/2008 | Masuyama et al. |
| 2009/0018996 A1 | 1/2009 | Hunt et al. |
| 2009/0172035 A1 | 7/2009 | Lessing et al. |
| 2009/0319310 A1* | 12/2009 | Little .............................. 705/7 |
| 2010/0030521 A1 | 2/2010 | Akhrarov et al. |
| 2010/0114899 A1 | 5/2010 | Guha et al. |
| 2011/0145223 A1 | 6/2011 | Cormode et al. |
| 2011/0208701 A1 | 8/2011 | Jackson et al. |
| 2011/0307503 A1 | 12/2011 | Dlugosch |
| 2013/0024167 A1 | 1/2013 | Blair et al. |
| 2013/0268318 A1 | 10/2013 | Richard |

OTHER PUBLICATIONS

Aiolfi, Marco et al., "Forecast Combinations," CREATES Research Paper 2010-21, School of Economics and Management, Aarhus University, 35 pp. (May 6, 2010).

Automatic Forecasting Systems Inc., Autobox 5.0 for Windows User's Guide, 82 pp. (1999).

Choudhury, J. Paul et al., "Forecasting of Engineering Manpower Through Fuzzy Associative Memory Neural Network with ARIMA: A Comparative Study", Neurocomputing, vol. 47, Iss. 1-4, pp. 241-257 (Aug. 2002).

Costantini, Mauro et al., "Forecast Combination Based on Multiple Encompassing Tests in a Macroeconomic DSGE System," Reihe Okonomie/ Economics Series 251, 24 pp. (May 2010).

Crowe, Keith E. et al., U.S. Appl. No. 11/431,089, filed May 9, 2006 entitled "Computer-Implemented System and Method for Generating Forecasts".

Crowe, Keith E. et al., U.S. Appl. No. 11/431,123, filed May 9, 2006 entitled "Computer-Implemented Systems and Methods for Storing Data Analysis Models".

Data Mining Group, available at http://www.dmg.org, printed May 9, 2005, 3 pp.

Funnel Web, Web site Analysis. Report, Funnel Web Demonstration, Authenticated Users History, http://www.quest.com/funnel.sub.--web/analyzer/sample/UserHist.html (1 pg.), Mar. 2002.

Funnel Web, Web site Analysis Report, Funnel Web Demonstration, Clients History, http://www/quest.com/funnel.sub.--web/analyzer/sample.ClientHist-.html (2 pp.), Mar. 2002.

Garavaglia, Susan et al., "A Smart Guide to Dummy Variables: Four Applications and a Macro," accessed from: http://web.archive.org/web/20040728083413/http://www.ats.ucla.edu/stat/sa- s/library/nesug98/p046.pdf, (2004).

(56) References Cited

OTHER PUBLICATIONS

Guerard John B. Jr., Automatic Time Series Modeling, Intervention Analysis, and Effective Forecasting. (1989) Journal of Statistical Computation and Simulation, 1563-5163, vol. 34, Issue 1, pp. 43-49.
Guralnik, V. and Srivastava, J., Event Detection from Time Series Data (1999), Proceedings of the 5th ACM SIGKDD International Conference on Knowledge Discovery and Data Mining, pp. 33-42.
Harrison, H.C. et al., "An Intelligent Business Forecasting System", ACM Annual Computer Science Conference, pp. 229-236 (1993).
Harvey, Andrew, "Forecasting with Unobserved Components Time Series Models," Faculty of Economics, University of Cambridge, Prepared for Handbook of Economic Forecasting, pp. 1-89 (Jul. 2004).
Jackson, Wilma S. et al., U.S. Appl. No. 11/431,127, filed May 9, 2006 entitled "Computer-Implemented Systems and Methods for Defining Events".
Jacobsen, Erik et al., "Assigning Confidence to Conditional Branch Predictions", IEEE, Proceedings of the 29th Annual International Symposium on Microarchitecture, 12 pp. (Dec. 2-4, 1996).
Keogh, Eamonn J. et al., "Derivative Dynamic Time Warping", In First SIAM International Conference on Data Mining (SDM'2001), Chicago, USA, pp. 1-11 (2001).
Kobbacy, Khairy A.H., et al., Abstract, "Towards the development of an intelligent inventory management system," Integrated Manufacturing Systems, vol. 10, Issue 6, (1999) 11 pp.
Kumar, Mahesh, "Combining Forecasts Using Clustering", Rutcor Research Report 40-2005, cover page and pp. 1-16 (Dec. 2005).
Leonard, Michael et al., "Mining Transactional and Time Series Data", abstract and presentation, International Symposium of Forecasting, 23 pp. (2003).
Leonard, Michael et al., "Mining Transactional and Time Series Data", abstract, presentation and paper, SUGI, 142 pp. (Apr. 10-13, 2005).
Leonard, Michael James, U.S. Appl. No. 11/696,951, filed Apr. 5, 2007 entitled "Systems and Methods for Mining Transactional and Times Series Data".
Leonard, Michael, "Large-Scale Automatic Forecasting Using Inputs and Calendar Events", abstract and presentation, International Symposium on Forecasting Conference, 56 pp. (Jul. 4-7, 2004).
Leonard, Michael, "Large-Scale Automatic Forecasting Using Inputs and Calendar Events", White Paper, pp. 1-27 (2005).
Leonard, Michael, "Large-Scale Automatic Forecasting: Millions of Forecasts", abstract and presentation, International Symposium of Forecasting, 156 pp. (2002).
Leonard, Michael, "Predictive Modeling Markup Language for Time Series Models", abstract and presentation, International Symposium on Forecasting Conference, 35 pp. (Jul. 4-7, 2004).
Leonard, Michael, "Promotional Analysis and Forecasting for Demand Planning: A Practical Time Series Approach", with exhibits 1 and 2, SAS Institute Inc., Cary, North Carolina, 50 pp. (2000).
Lu, Sheng et al., "A New Algorithm for Linear and Nonlinear ARMA Model Parameter Estimation Using Affine Geometry", IEEE Transactions on Biomedical Engineering, vol. 48, No. 10, pp. 1116-1124 (Oct. 2001).
Malhotra, Manoj K. et al., "Decision making using multiple models", European Journal of Operational Research, 114, pp. 1-14 (1999).
McQuarrie, Allan D.R. et al., "Regression and Time Series Model Selection", World Scientific Publishing Co. Pte. Ltd., 40 pp. (1998).
Oates, Tim et al., "Clustering Time Series with Hidden Markov Models and Dynamic Time Warping", Computer Science Department, LGRC University of Massachusetts, In Proceedings of the IJCAI-99, 5 pp. (1999).
Park, Kwan Hee, Abstract "Development and evaluation of a prototype expert system for forecasting models", Mississippi State University, 1990, 1 pg.
Park, Youngjin et al., U.S. Appl. No. 11/431,116, filed May 9, 2006 entitled "Computer-Implemented Systems and Methods for Processing Time Series Data".
Product Brochure, Forecast PRO, 2000, 12 pp.

Quest Software, "Funnel Web Analyzer: Analyzing the Way Visitors Interact with Your Web Site", http://www.quest.com/funnel.sub.--web/analyzer (2 pp.), Mar. 2002.
Safavi, Alex "Choosing the right forecasting software and system." The Journal of Business Forecasting Methods & Systems 19.3 (2000): 6-10. ABI/INFORM Global, ProQuest.
SAS Institute Inc., SAS/ETS User's Guide, Version 8, Cary NC; SAS Institute Inc., (1999) 1543 pages.
Seasonal Dummy Variables, Mar. 2004, http://shazam.econ.ubc.ca/intro/dumseas.htm, Accessed from: http://web.archive.org/web/20040321055948/http://shazam.econ.ubc.ca/intro-/dumseas.htm.
Simoncelli, Eero, "Least Squares Optimization," Center for Neural Science, and Courant Institute of Mathematical Sciences, pp. 1-8 (Mar. 9, 2005).
Tashman, Leonard J. et al., Abstract "Automatic Forecasting Software: A Survey and Evaluation", International Journal of Forecasting, vol. 7, Issue 2, Aug. 1991, 1 pg.
Using Predictor Variables, (1999) SAS OnlineDoc: Version 8, pp. 1325-1349, Accessed from: http://www.okstate.edu/sas/v8/saspdf/ets/chap27.pdf.
van Wijk, Jarke J. et al., "Cluster and Calendar based Visualization of Time Series Data", IEEE Symposium on Information Visualization (INFOVIS '99), San Francisco, pp. 1-6 (Oct. 25-26, 1999).
Vanderplaats, Garret N., "Numerical Optimization Techniques for Engineering Design", Vanderplaats Research & Development (publisher), Third Edition, 18 pp. (1999).
Wang, Liang et al., "An Expert System for Forecasting Model Selection", IEEE, pp. 704-709 (1992).
Weiss, Jack, "Lecture 16—Wednesday, Feb. 8, 2006," http://www.unc.edu/courses/2006spring/ecol/145/001/docs/lectures/lecture16.htm, 9 pp. (Feb. 9, 2006).
Atuk, Oguz et al., "Seasonal Adjustment in Economic Time Series," Statistics Department, Discussion Paper No. 2002/1, Central Bank of the Republic of Turkey, Central Bank Review, 15 pp. (2002).
Babu, G., "Clustering in non-stationary environments using a clan-based evolutionary approach," Biological Cybernetics, Sep. 7, 1995, Springer Berlin I Heidelberg, pp. 367-374, vol. 73, Issue: 4.
Bruno, Giancarlo et al., "The Choice of Time Intervals in Seasonal Adjustment: A Heuristic Approach," Institute for Studies and Economic Analysis, Rome Italy, 14 pp. (2004).
Bruno, Giancarlo et al., "The Choice of Time Intervals in Seasonal Adjustment: Characterization and Tools," Institute for Studies and Economic Analysis, Rome, Italy, 21 pp. (Jul. 2001).
Bradley, D.C. et al., "Quantitation of measurement error with Optimal Segments: basis for adaptive time course smoothing," Am J Physiol Endocrinol Metab Jun. 1, 1993 264:(6) E902-E911.
Huang, N. E. et al., "Applications of Hilbert-Huang transform to non-stationary financial time series analysis." Appl. Stochastic Models Bus. Ind., 19: 245-268 (2003).
IBM, "IBM Systems, IBM Power Executive Installation and User's Guide," Version 2.10, 62 pp. (Aug. 2007).
Kalpakis, K. et al., "Distance measures for effective clustering of ARIMA time-series," Data Mining, 2001. ICDM 2001, Proceedings IEEE International Conference on, vol., No., pp. 273-280, 2001.
Keogh, E. et al., "An online algorithm for segmenting time series," Data Mining, 2001. ICDM 2001, Proceedings IEEE International Conference on , vol., No., pp. 289-296, 2001.
Keogh, Eamonn et al., "Segmenting Time Series: A Survey and Novel Approach," Department of Information and Computer Science, University of California, Irvine, California 92697, 15 pp. (2004).
Palpanas, T. et al., "Online amnesic approximation of streaming time series," Data Engineering, 2004. Proceedings. 20th International Conference on , vol., No., pp. 339-349, Mar. 30-Apr. 2, 2004.
Wang Xiao-Ye; Wang Zheng-Ou; "A structure-adaptive piece-wise linear segments representation for time series," Information Reuse and Integration, 2004. IR I 2004. Proceedings of the 2004 IEEE International Conference on , vol., No., pp. 433-437, Nov. 8-10, 2004.
Yu, Lean et al., "Time Series Forecasting with Multiple Candidate Models: Selecting or Combining?" Journal of System Science and Complexity, vol. 18, No. 1, pp. 1-18 (Jan. 2005).
Non-Final Office Action of Aug. 29, 2012 for U.S. Appl. No. 13/031,828, 18 pages.

(56) References Cited

OTHER PUBLICATIONS

Non-Final Office Action of Oct. 31, 2007 for U.S. Appl. No. 10/402,849, 14 pages.
Final Office Action of May 21, 2008 for U.S. Appl. No. 10/402,849, 19 pages.
Non-Final Office Action of Feb. 20, 2009 for U.S. Appl. No. 10/402,849, 21 pages.
Final Office Action of Jul. 1, 2010 for U.S. Appl. No. 10/402,849, 24 pages.
Non-Final Office Action of Aug. 30, 2013 for U.S. Appl. No. 10/402,849, 29 pages.
Notice of Allowance of Sep. 16, 2013 for U.S. Appl. No. 13/031,828 17 pages.
Non-Final Office Action of Oct. 25, 2013 for U.S. Appl. No. 13/189,131, 37 pages.
Non-Final Office Action of Mar. 26, 2014 for U.S. Appl. No. 13/548,282, 40 pages.
Final Office Action of Apr. 24, 2014 for U.S. Appl. No. 13/189,131, 30 pages.
Non-Final Office Action of Aug. 8, 2014 for U.S. Appl. No. 10/402,849, 39 pages.

* cited by examiner

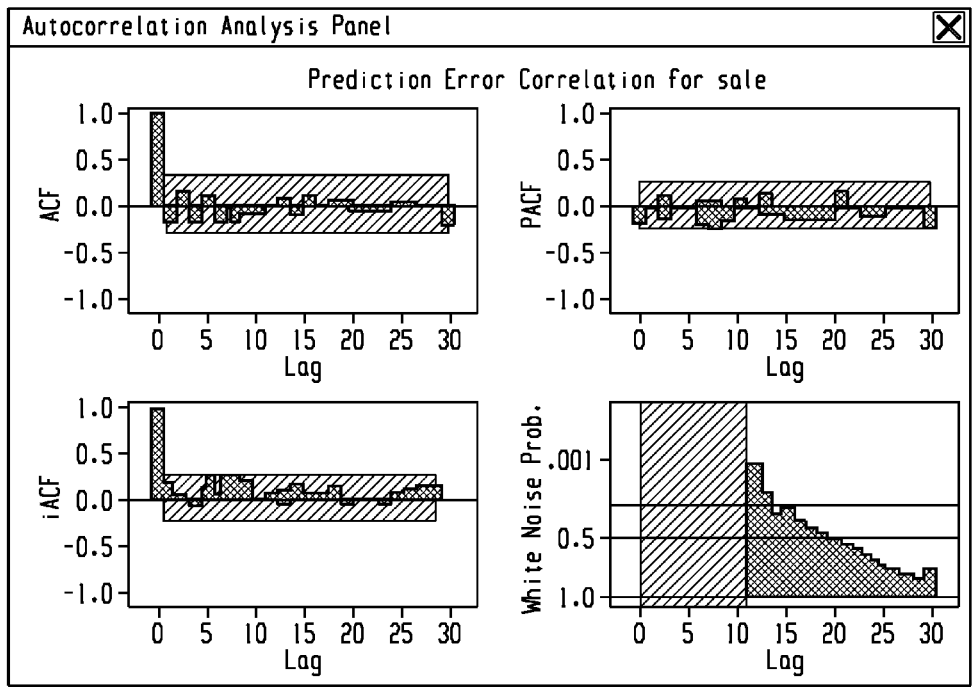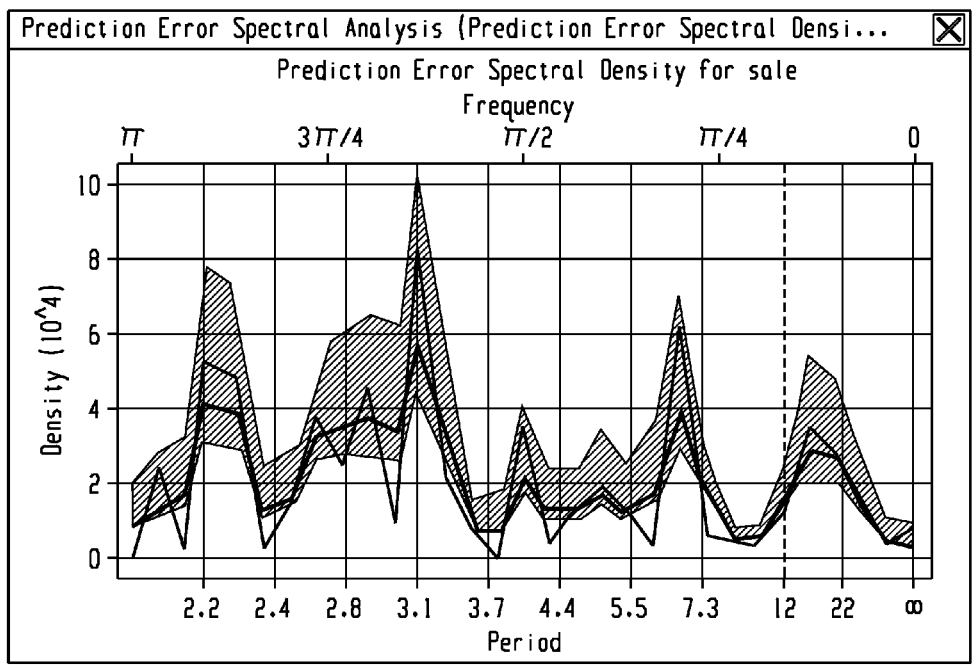
Fig. 25

Combine Models

⚠ If this model is currently in use, editing it will cause all affected series to be automatically updated and the project to be reconciled. Forecasts may be affected.
To see if and where the model is currently being used, you may search here.

Name: COMBINEDMODEL2
Description: Combined Model specification

| Use | Model/ | Type | MAPE | Weight |
|-----|--------|------|------|--------|
| ☐ | HPF2_83 | Generated | 5.29 | 0.0 |
| ☑ | HPF2_84 | Generated | 5.29 | 0.4 |
| ☑ | HPF2_84COPY1 | Custom | 5.29 | 0.5 |
| ☐ | HPF2_85 | Generated | 6.7 | 0.0 |
| ☑ | HPF2_85COPY1 | Custom | 6.7 | 0.1 |

Method of combination: USERDEF
Statistic: RMSE
Treatment of missing values: RESCALE
Compute prediction error variance series: DIAG ☐ Forecast encompassing test: OLS  0
☐ Percentage of missing forecast values in the combination horizon: 1
☐ Percentage of missing forecast values in the combination estimation region: 1

[ View Code... ]
[ OK ]  [ Cancel ]

*Fig. 26*

| Combine Models | | | | | |
|---|---|---|---|---|---|

If this model is currently in use, editing it will cause all affected series to be automatically updated and the project to be reconciled. Forecasts may be affected.
To see if and where the model is currently being used, you may search here.

Name: COMBINEDMODEL2

Description: Combined Model specification

| Use | Model/ | Type | MAPE | Weight |
|---|---|---|---|---|
| ☐ | HPF2_83 | Generated | 5.29 | 0.0 |
| ☑ | HPF2_84 | Generated | 5.29 | 0.0 |
| ☑ | HPF2_84COPY1 | Custom | 5.29 | 0.0 |
| ☐ | HPF2_85 | Generated | 6.7 | 0.0 |
| ☑ | HPF2_85COPY1 | Custom | 6.7 | 0.0 |

Method of combination: RANKWGT ▽   SET RANKED WEIGHT

Statistic: RMSE ▽

Treatment of missing

| Set Ranked Weights | | ☒ |
|---|---|---|
| 0.20 | 0.30 | 0.50 |

Compute prediction er

☐ Forecast encompass

☐ Percentage of miss       OK    Cancel

☐ Percentage of miss                                on: 0

View Code...

OK    Cancel

*Fig. 27*

Compare Models

Plot | Statistics of Fit

Selection Statistics of Fit

| Model | C | APC | GMAPE | GMAPES | GMAPPE | GMASPE | GMAAE | MAE | MAPE | MAPES |
|---|---|---|---|---|---|---|---|---|---|---|
| COMBINEDMODEL2 | 0.305541 | 943.125721 | 3.91 | 44.910443 | 3.90 | 3.90 | 0.90 | 23.305216 | 5.54 | 62.454877 |
| Generated ARIMA Model (HPF2_83) | 0.137771 | 849.367408 | 3.47 | 39.495851 | 3.46 | 3.47 | 0.75 | 22.270652 | 5.29 | 59.218332 |
| Generated ARIMA Model (HPF2_84) | 0.137771 | 849.367408 | 3.47 | 39.495851 | 3.46 | 3.47 | 0.75 | 22.270652 | 5.29 | 59.215002 |
| HPF2_84COPY1 | 0.137771 | 849.367408 | 3.47 | 39.495851 | 3.46 | 3.47 | 0.75 | 22.270652 | 5.29 | 59.208002 |
| Generated Smoothing Model (HPF2_85) | 0.512457 | 1418.555837 | 4.37 | 50.062623 | 4.36 | 4.36 | 1.01 | 22.559106 | 6.70 | 76.534604 |
| HPF2_85COPY1 | 0.512457 | 1418.555837 | 4.37 | 50.062623 | 4.36 | 4.36 | 1.01 | 22.559106 | 6.70 | 76.534604 |
| Generated Model (HPF2_86) | 0.636126 | 921.317558 | 3.60 | 41.310580 | 3.60 | 3.60 | 0.83 | 22.002476 | 5.27 | 59.175088 |

Close    Help

*Fig. 29*

Create New Scenario

Name: Scenario1

Description: Scenario for Combination Model

Choose a model to create a scenario:

| Model | Type | Rank | MAPE | All Input.... | No Input.... |
|---|---|---|---|---|---|
| Generated Model (TOP_7) | Combination (Generated) | 1 | 1.18 | | x |
| Generated Smoothing Model (TOP_6) | Generated | 2 | 1.29 | | x |
| COMBINEDMODEL1 | Combination (Custom) | 2 | 1.29 | | x |
| TOP_2COPY1 | Custom | 2 | 1.29 | | x |

Quick View....

[OK] [Cancel]

Fig. 31

COMPUTER-IMPLEMENTED SYSTEMS AND METHODS FOR TESTING LARGE SCALE AUTOMATIC FORECAST COMBINATIONS

This is a continuation-in-part of U.S. patent application Ser. No. 13/189,131, titled "Computer-Implemented Systems and Methods for Large Scale Automatic Forecast Combinations," filed on Jul. 22, 2011; this application also claims priority to U.S. Provisional Application No. 61/594,442, filed on Feb. 3, 2012. The entirety of these priority applications are incorporated herein by reference.

TECHNICAL FIELD

This document relates generally to computer-implemented forecasting and more particularly to testing a combined forecast that is generated using multiple forecasts.

BACKGROUND

Forecasting is a process of making statements about events whose actual outcomes typically have not yet been observed. A commonplace example might be estimation for some variable of interest at some specified future date. Forecasting often involves formal statistical methods employing time series, cross-sectional or longitudinal data, or alternatively to less formal judgmental methods. Forecasts are often generated by providing a number of input values to a predictive model, where the model outputs a forecast. While a well designed model may give an accurate forecast, a configuration where predictions of multiple models are considered when generating a forecast may provide even stronger forecast results.

SUMMARY

In accordance with the teachings herein, systems and methods are provided for evaluating a physical process with respect to one or more attributes of the physical process by combining forecasts for the one or more physical process attributes, where data for evaluating the physical process is generated over time. In one example, a forecast model selection graph is accessed, the forecast model selection graph comprising a hierarchy of nodes arranged in parent-child relationships. A plurality of model forecast nodes are resolved, where resolving a model forecast node includes generating a node forecast for the one or more physical process attributes. A combination node is processed, where a combination node transforms a plurality of node forecasts at child nodes of the combination node into a combined forecast. A selection node is processed, where a selection node chooses a node forecast from among child nodes of the selection node based on a selection criteria.

As another example, a system for storing evaluating a physical process with respect to one or more attributes of the physical process by combining forecasts for the one or more physical process attributes, where data for evaluating the physical process is generated over time is provided. The system may include one or more data processors and a computer-readable medium encoded with instructions for commanding the one or more data processors to execute steps. In the steps, a forecast model selection graph is accessed, the forecast model selection graph comprising a hierarchy of nodes arranged in parent-child relationships. A plurality of model forecast nodes are resolved, where resolving a model forecast node includes generating a node forecast for the one or more physical process attributes. A combination node is processed, where a combination node transforms a plurality of node forecasts at child nodes of the combination node into a combined forecast. A selection node is processed, where a selection node chooses a node forecast from among child nodes of the selection node based on a selection criteria.

As a further example, a computer-readable storage medium may be encoded with instructions for commanding one or more data processors to execute a method. In the method, a forecast model selection graph is accessed, the forecast model selection graph comprising a hierarchy of nodes arranged in parent-child relationships. A plurality of model forecast nodes are resolved, where resolving a model forecast node includes generating a node forecast for the one or more physical process attributes. A combination node is processed, where a combination node transforms a plurality of node forecasts at child nodes of the combination node into a combined forecast. A selection node is processed, where a selection node chooses a node forecast from among child nodes of the selection node based on a selection criteria.

As an additional example, one or more computer-readable storage mediums may store data structures for access by an application program being executed on one or more data processors for evaluating a physical process with respect to one or more attributes of the physical process by combining forecasts for the one or more physical process attributes, where physical process data generated over time is used in the forecasts for the one or more physical process attributes. The data structures may include a predictive models data structure, the predictive models data structure containing predictive data model records for specifying predictive data models and a forecast model selection graph data structure, where the forecast model selection graph data structure contains data about a hierarchical structure of nodes which specify how the forecasts for the one or more physical process attributes are combined, where the hierarchical structure of nodes has a root node wherein the nodes include model forecast nodes, one or more model combination nodes, and one or more model selection nodes. The forecast model selection graph data structure may include model forecast node data which specifies for the model forecast nodes which particular predictive data models contained in the predictive models data structure are to be used for generating forecasts, model combination node data which specifies for the one or more model combination nodes which of the forecasts generated by the model forecast nodes are to be combined, and selection node data which specifies for the one or more model selection nodes model selection criteria for selecting, based upon model forecasting performance, models associated with the model forecast nodes or the one or more model combination nodes.

In accordance with the teachings herein, systems and methods are provided for evaluating performance of forecasting models. A plurality of forecasting models may be generated using a set of in-sample data. A selection of two or more forecasting models may be received from the plurality of forecasting models for use in generating a combined forecast. A set of actual out-of-sample data may be received. An ex-ante combined forecast may be generated for an out-of-sample period using the selected two or more forecasting models. The ex-ante combined forecast and the set of actual out-of-sample data may be provided for use in evaluating performance of the combined forecast.

BRIEF DESCRIPTION OF THE FIGURES

FIGS. 15-32 depict graphical user interfaces that may be used in generating and comparing combined forecasts.

DETAILED DESCRIPTION

Figure 1:
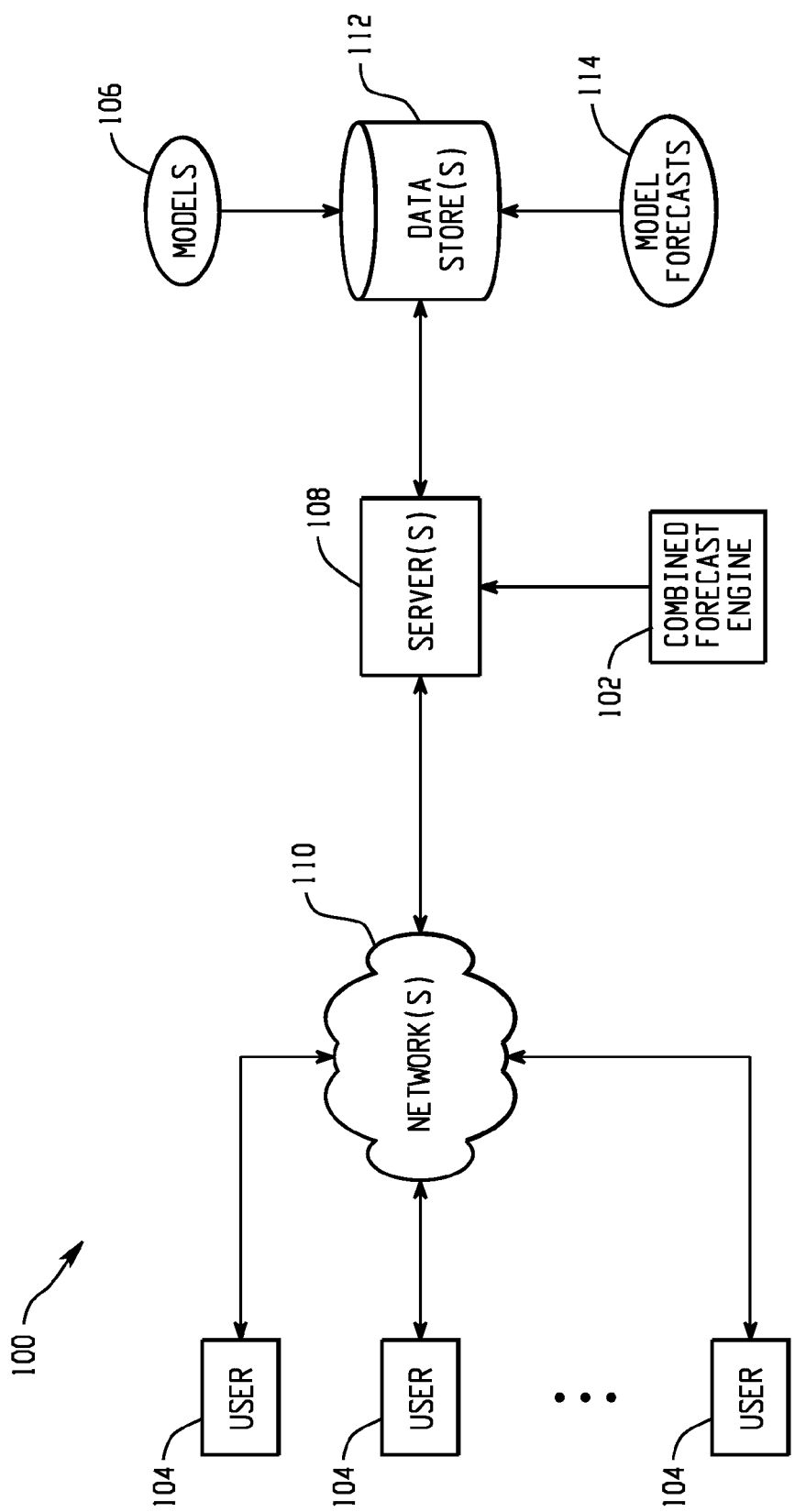
FIG. 1 is a block diagram depicting a computer-implemented combined forecast engine.

FIG. 1 is a block diagram depicting a computer-implemented combined forecast engine. FIG. 1 depicts a computer-implemented combined forecast engine 102 for facilitating the creation of combined forecasts and evaluation of created combined forecasts against individual forecasts as well as other combined forecasts. Forecasts are predictions that are typically generated by a predictive model based on one or more inputs to the predictive model. A combined forecast engine 102 combines predictions made by multiple models, of the same or different type, to generate a single, combined forecast that can incorporate the strengths of the multiple, individual models which comprise the combined forecast.

For example, a combined forecast may be generated (e.g., to predict a manufacturing process output, to estimate product sales) by combining individual forecasts from two linear regression models and one autoregressive regression model. The individual forecasts may be combined in a variety of ways, such as by a straight average, via a weighted average, or via another method. To generate a weighted forecast, automated analysis of the individual forecasts may be performed to identify weights to generate an optimum combined forecast that best utilizes the available individual forecasts.

The combined forecast engine 102 provides a platform for users 104 to generate combined forecasts based on individual forecasts generated by individual predictive models 106. A user 104 accesses the combined forecast engine 102, which is hosted on one or more servers 108, via one or more networks 110. The one or more servers 108 are responsive to one or more data stores 112. The one or more data stores 112 may contain a variety of data that includes predictive models 106 and model forecasts 114.

Figure 2:
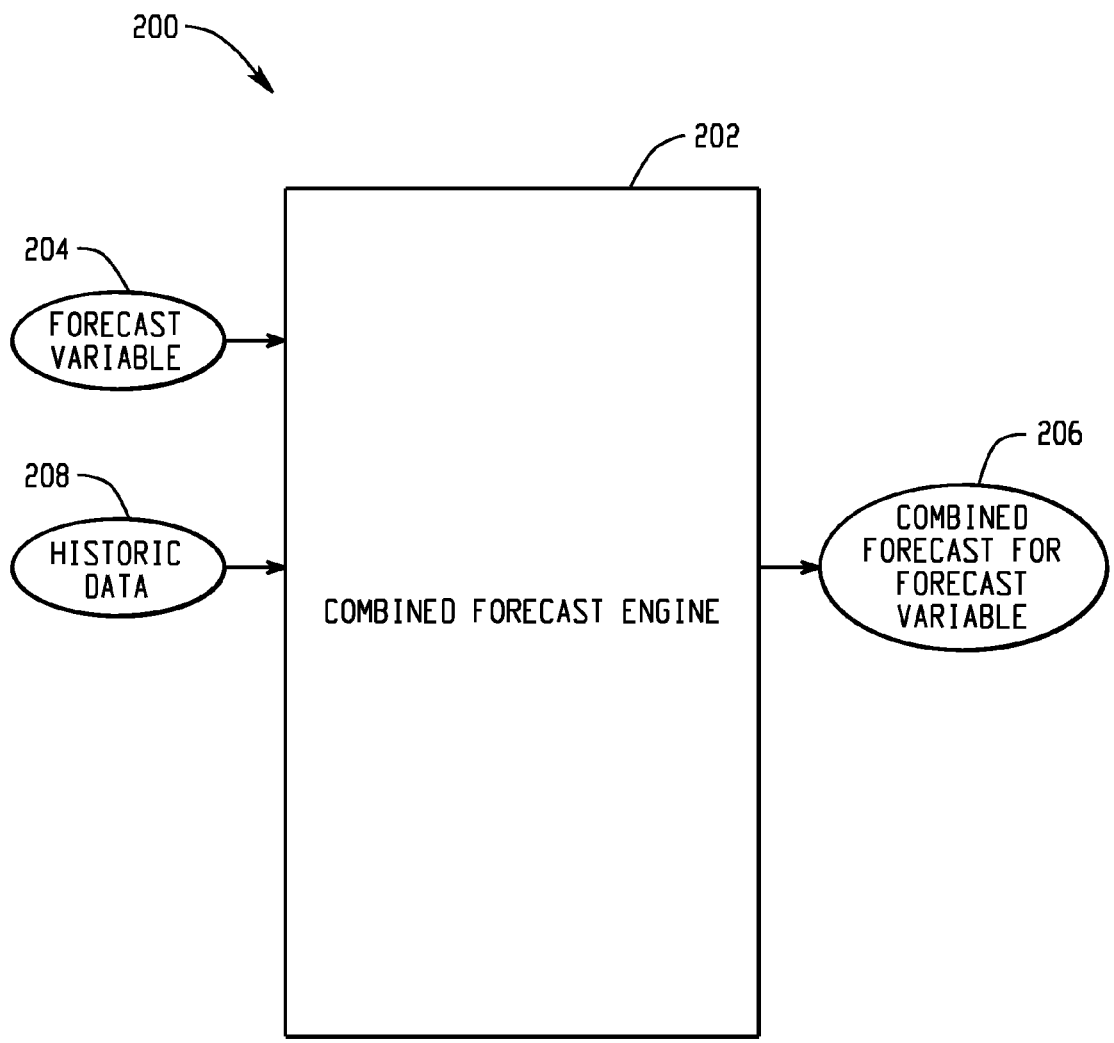
FIG. 2 is a block diagram depicting the generation of a combined forecast for a forecast variable.

FIG. 2 is a block diagram depicting the generation of a combined forecast for a forecast variable (e.g., one or more physical process attributes). The combined forecast engine 202 receives an identification of a forecast variable 204 for which to generate a combined forecast 206. For example, a user may command that the combined forecast engine 202 generate a combined forecast 206 of sales for a particular clothing item. To generate the combined forecast 206, the combined forecast engine 202 may identify a number of individual predictive models. Those individual predictive models may be provided historic data 208 as input, and those individual predictive models provide individual forecasts based on the provided historic data 208. The combined forecast engine 202 performs operations to combine those individual predictions of sales of the particular clothing item to generate the combined forecast of sales for the particular clothing item.

Figure 3:
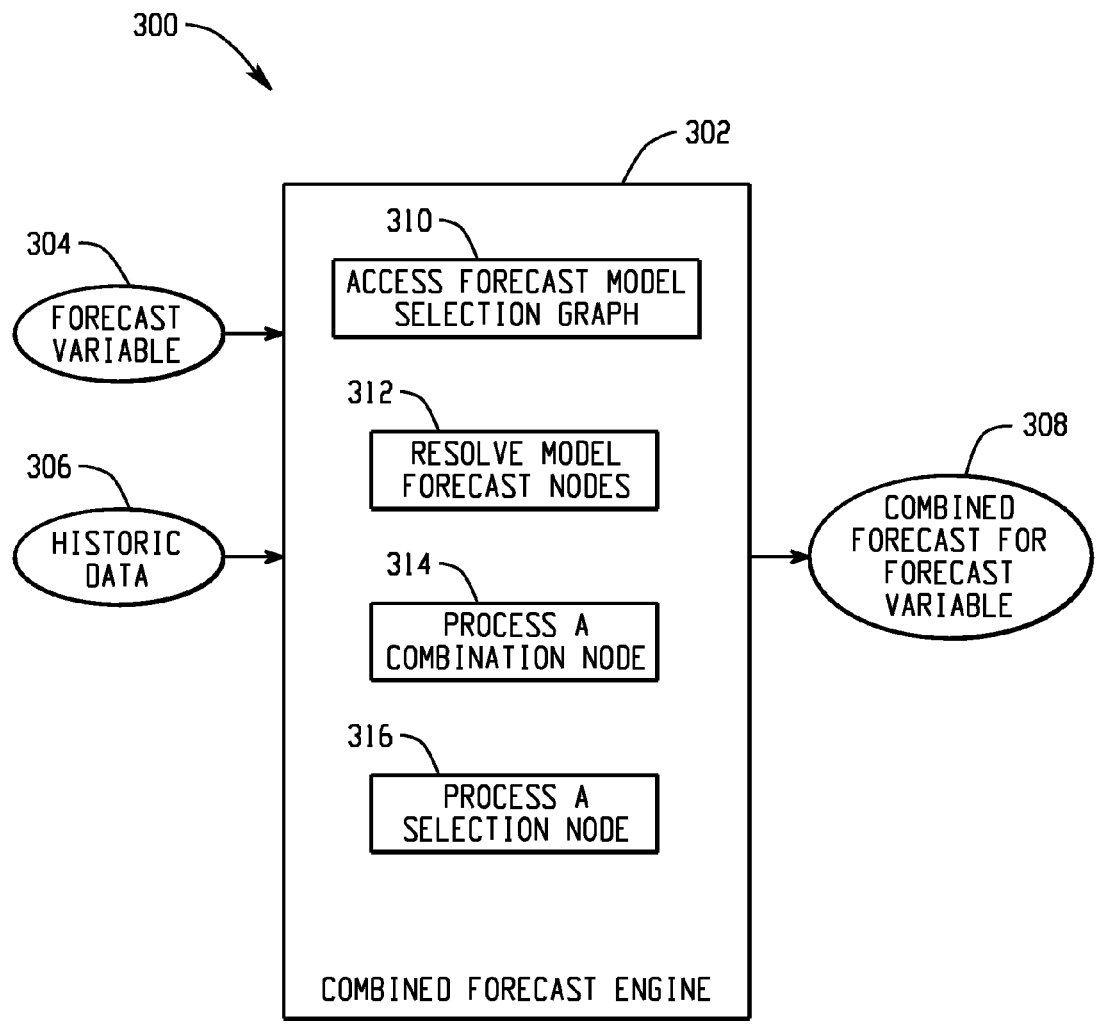
FIG. 3 is a block diagram depicting steps that may be performed by a combined forecast engine in generating a combined forecast.

FIG. 3 is a block diagram depicting steps that may be performed by a combined forecast engine in generating a combined forecast. The combined forecast engine 302 receives a forecast variable 304 for which to generate a combined forecast as well as historic data 306 to be used as input to individual predictive models whose predictions become components of the combined forecast 308.

The combined forecast engine 302 may utilize model selection and model combination operations to generate a combined forecast. For example, the combined forecast engine 302 may evaluate a physical process with respect to one or more attributes of the physical process by combining forecasts for the one or more physical process attributes. Data for evaluating the physical process may be generated over time, such as time series data.

At 310, the combined forecast engine accesses a forecast model selection graph. A forecast model selection graph incorporates both model selection and model combination into a decision based framework that, when applied to a time series, automatically selects a forecast from an evaluation of independent, individual forecasts generated. The forecast model selection graph can include forecasts from statistical models, external forecasts from outside agents (e.g., expert predictions, other forecasts generated outside of the combined forecast engine 302), or combinations thereof. The forecast model selection graph may be used to generate combined forecasts as well as comparisons among competing generated forecasts to select a best forecast. A forecast model selection graph for a forecast decision process of arbitrary complexity may be created, limited only by external factors such as computational power and machine resource limits.

A forecast model selection graph may include a hierarchy of nodes arranged in parent-child relationships including a root node. The hierarchy may include one or more selection nodes, one or more combination nodes, and a plurality of model forecast nodes. Each of the model forecast nodes is associated with a predictive model. The combined forecast engine may resolve the plurality of model forecast nodes, as shown at 312. Resolving a model forecast node includes generating a node forecast for the forecast variable 304 using the predictive model for the model forecast node. For example, a first model forecast node may be associated with a regression model. To resolve the first model forecast node, the combined forecast engine 302 provides the historic data 306 to the regression model, and the regression model generates a node forecast for the model forecast node. A second model forecast node may be associated with a human expert prediction. In such a case, computation by the combined forecast engine 302 may be limited, such as simply accessing the human expert's prediction from storage. A third model forecast node may be associated with a different combined model. To resolve the third model forecast node, the combined forecast engine 302 provides the historic data 306 to the different combined model, and the different combined model generates a node forecast for the model forecast node. Other types of models and forecasts may also be associated with a model forecast node.

At 314, the combined forecast engine processes a combination node. In processing a combination node, the combined forecast engine 302 transforms a plurality of node forecasts at child nodes of the combination nodes into a combined forecast. For example, a combination node having three child nodes would have the node forecasts for those three child nodes combined into a combined forecast for the combination node. Combining node forecasts may be done in a variety of ways, such as via a weighted average. A weighted average may weight each of the three node forecasts equally, or the combined forecast engine 302 may implement more complex logic to identify a weight for each of the three node forecasts. For example, weight types may include a simple average, user-defined weights, rank weights, ranked user-weights, AICC weights, root mean square error weights, restricted least squares eights, OLS weights, and least absolute deviation weights.

At 316, the combined forecast engine processes a selection node. In processing a selection node, the combined forecast engine 302 chooses a node forecast from among child nodes of the selection node based on a selection criteria. The selection criteria may take a variety of forms. For example, the selection criteria may dictate selection of a node forecast associated with a node whose associated model performs best in a hold out sample analysis.

As another example, metadata may be associated with models associated with node forecasts, where the metadata identifies a model characteristic of a model. The selection criteria may dictate selection of a node forecast whose metadata model characteristic best matches a characteristic of the forecast variable 304. For example, if the forecast variable 304 tends to behave in a seasonal pattern, then the selection criteria may dictate selection of a node forecast that was generated by a model whose metadata identifies it as handling seasonal data. Other example model metadata characteristics include trending model, intermittent model, and transformed model.

As a further example, the selection criteria may dictate selection of a node forecast having the least amount of missing data. A node forecast may include forecasts for the forecast variable 304 for a number of time periods in the future (e.g., forecast variable at t+1, forecast variable at t+2, . . . ). In some circumstances, a node forecast may be missing data for certain future time period forecasts (e.g., the node forecast is an expert's prediction, where the expert only makes one prediction at t+6 months). If a certain time period in the future is of specific interest, the selection criteria may dictate that a selected node forecast must not be missing a forecast at the time period of interest (e.g., when the time period of interest is t+1 month, the node forecast including the expert's prediction may not be selected).

As another example, the selection criteria may be based on a statistic of fit. For example, the combined forecast engine 302 may fit models associated with child nodes of a selection node with the historic data 306 and calculate statistics of fit for those models. Based on the determined statistics of fit, the combined forecast engine 302 selects the forecast node associated with the model that is a best fit.

The combined forecast engine 302 may continue resolving model forecast nodes 312 and processing combination and selection nodes 314, 316 until a final combined forecast is generated. For example, the combined forecast engine may work from the leaves up to the root in the forecast model selection graph hierarchy, where the final combined forecast is generated at the root node.

Figure 4:
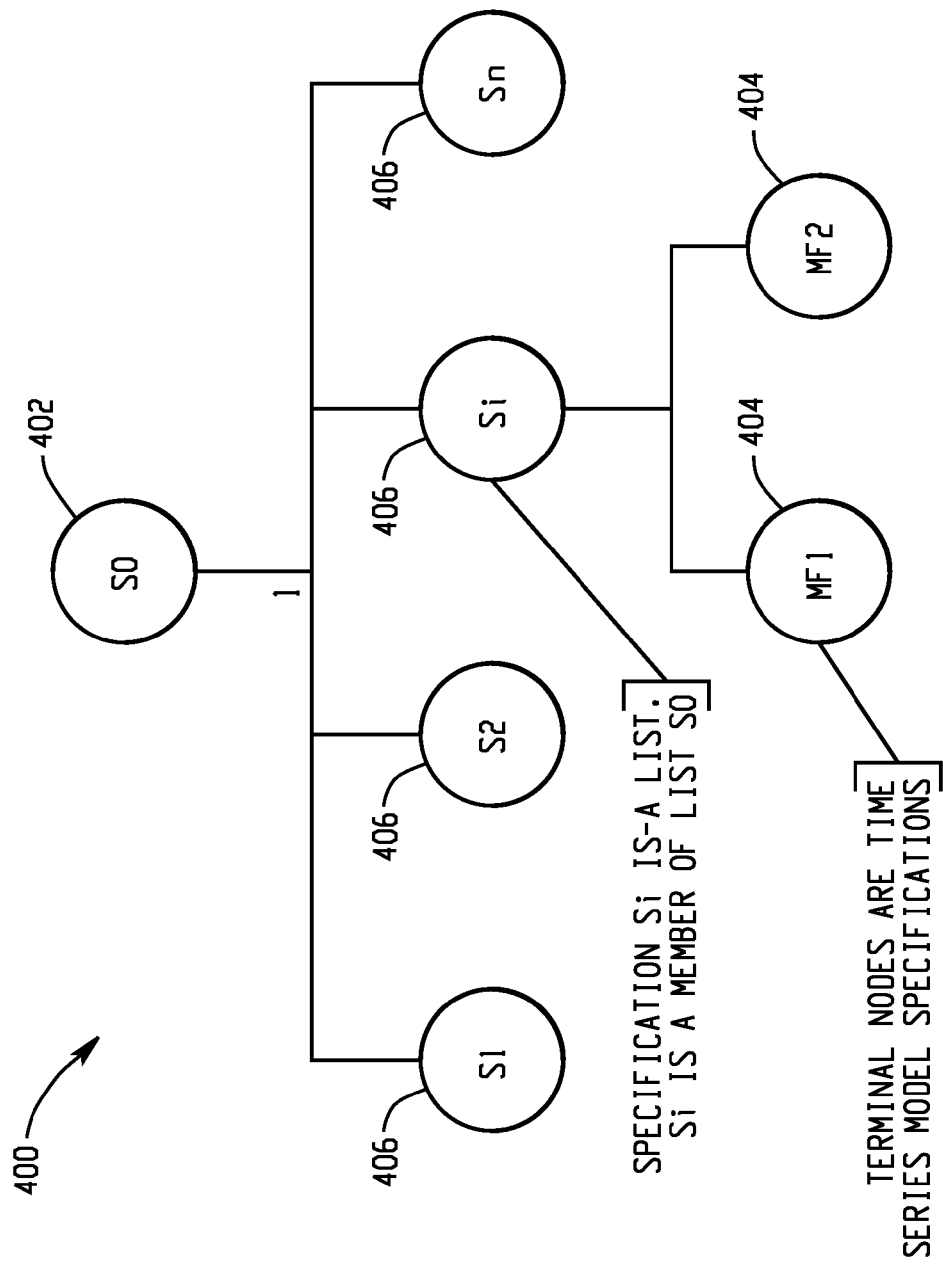
FIG. 4 depicts an example forecast model selection graph.

FIG. 4 depicts an example forecast model selection graph. The forecast model selection graph includes a hierarchy of nodes arranged in parent-child relationships that includes a root node 402. The forecast model selection graph also includes two model forecast nodes 404. The model forecast nodes 404 may be associated with a model that can be used to forecast one or more values for a forecast variable. A model associated with a model forecast node 404 may also be a combined model or a forecast generated outside of the combined forecast engine, such as an expert or other human generated forecast. The model forecast nodes 404 are resolved to identify a node forecast (e.g., using an associated model to generate a node forecast, accessing an expert forecast from storage).

The forecast model selection graph also includes selection nodes 406. A selection node may include a selection criteria for choosing a node forecast from among child nodes (e.g., model forecast nodes 404) of the selection node 406. Certain of the depicted selection nodes S1, S2, Sn do not have their child nodes depicted in FIG. 4.

Figure 5:
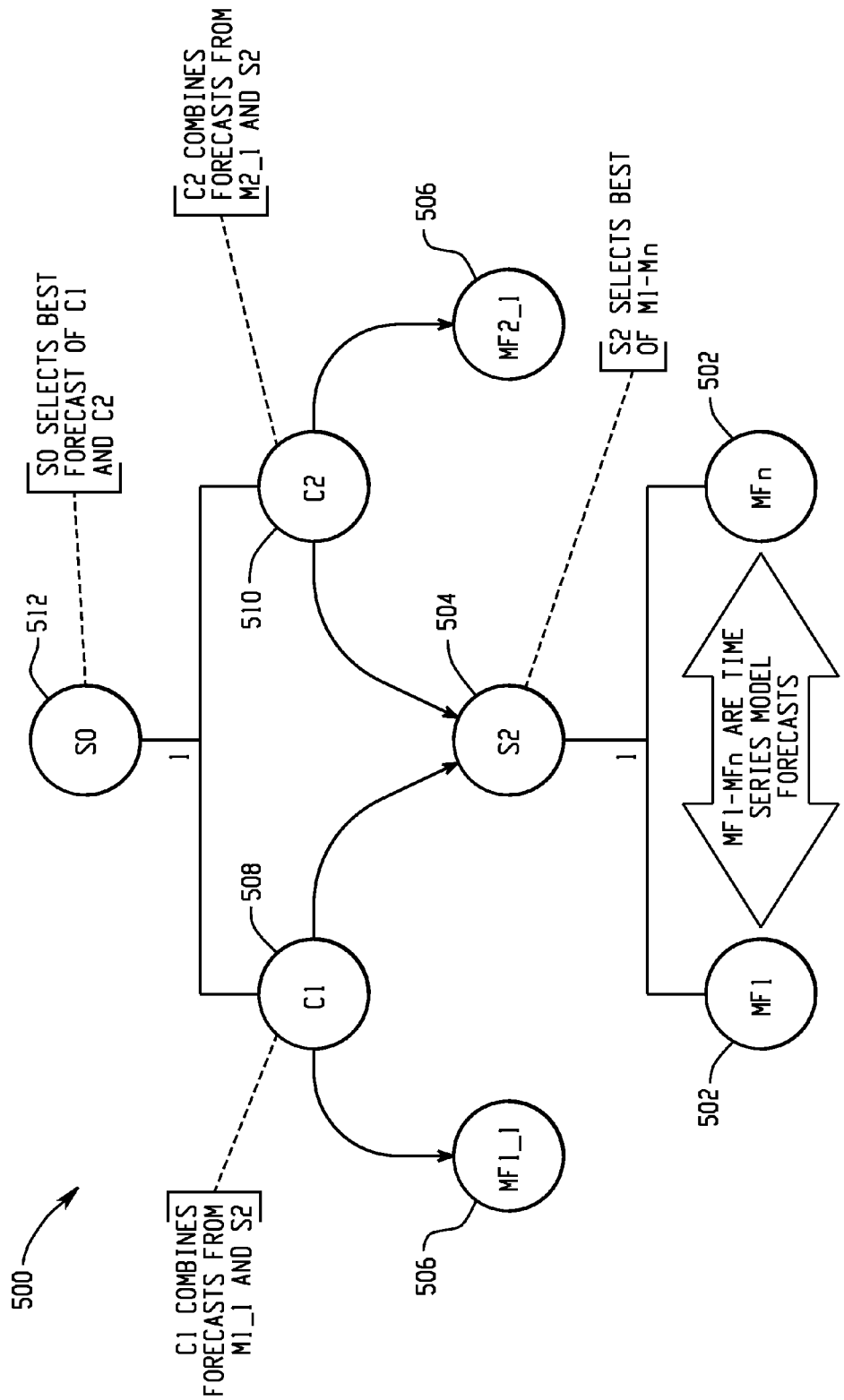
FIG. 5 depicts an example forecast model selection graph including selection nodes, combination nodes, and model forecast nodes.

FIG. 5 depicts an example forecast model selection graph including selection nodes, combination nodes, and model forecast nodes. To generate a combined forecast for the forecast model selection graph 500, model forecast nodes 502 are resolved to generate node forecasts for one or more forecast variables (e.g., physical process attributes). With node forecasts resolved for the model forecast nodes 502, a selection node 504 selects one of the node forecasts associated with the model forecast nodes 502 based on a selection criteria. For example, the selection criteria may dictate a model forecast based on metadata associated with a model used to generate the model forecast at the model forecast node 502.

Additional model forecast nodes 506 may be resolved to generate node forecasts at those model forecast nodes 506. A first combined forecast node 508 combines a model forecast associated with model forecast node MF1_1 and the model forecast at the selection node 504 to generate a combined forecast at the combination node 508. A second combined forecast node 510 combines a model forecast associated with model forecast node MF2_1 and the model forecast at the selection node 504 to generate a combined forecast at the combination node 510. Another selection node 512 selects a model forecast from one of the two combination nodes 508, 510 based on a selection criteria as the final combined forecast for the forecast model selection graph 500.

A forecast model selection graph may take a variety of forms. For example, the forecast model selection graph may be represented in one or more records in a database or described in a file. In another implementation, the forecast model selection graph may be represented via one or more XML based data structures. The XML data structures may identify the forecast sources to combine, diagnostic tests used in the selection and filtering of forecasts, methods for determining weights to forecasts to be combined, treatment of missing values, and selection of methods for estimating forecast prediction error variance.

Figure 6:
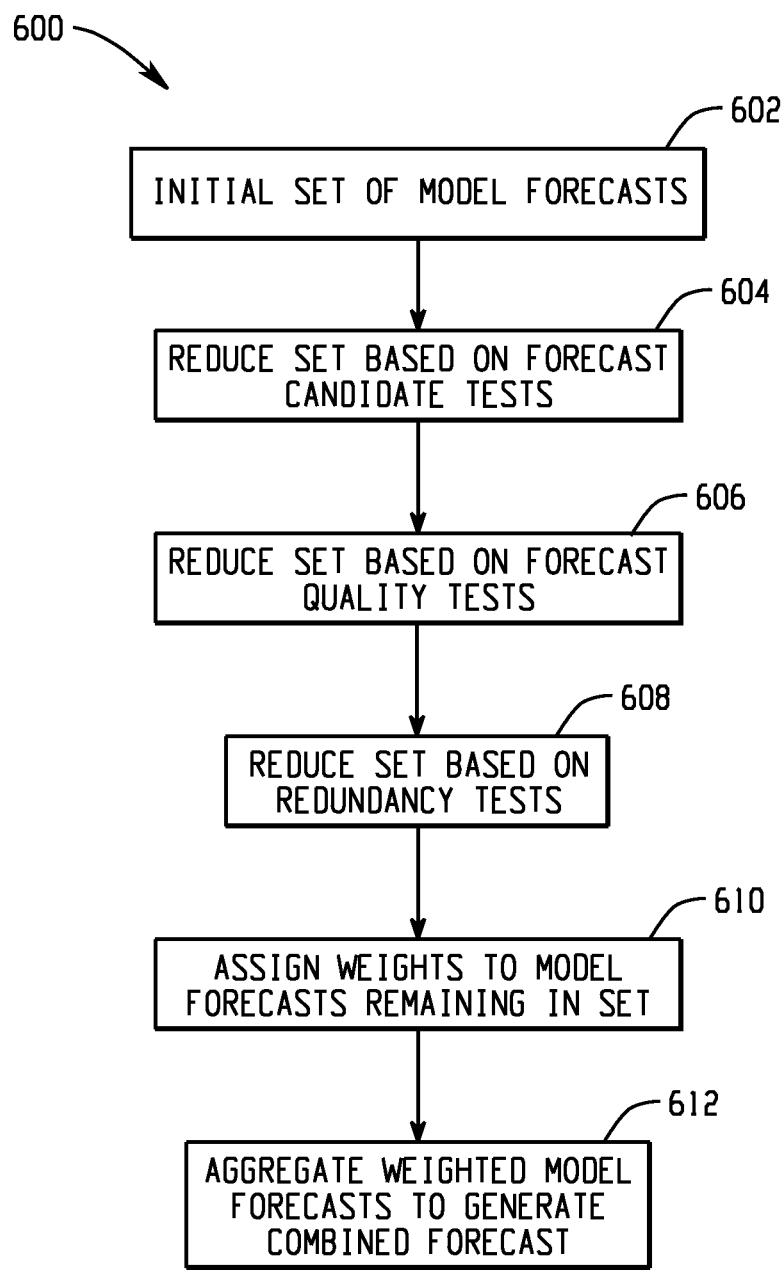
FIG. 6 is a block diagram depicting example operations that may be performed by a combined forecast engine in combining one or more forecasts.

FIG. 6 is a block diagram depicting example operations that may be performed by a combined forecast engine in combining one or more forecasts (e.g., when processing a combination node). At 602, an initial set of model forecasts is identified. In some implementations, all identified model forecasts may be combined to create a combined forecast. However, in some implementations, it may be desirable to filter the models used in creating a combined forecast. For example, at 604, the set of model forecasts may be reduced at 604 based on one or more forecast candidate tests. The forecast candidate tests may take a variety of forms, such as analysis of the types of models used to generate the model forecasts identified at 602 and characteristics of the forecast variable. For example, if the forecast variable is a trending variable, the candidate tests may eliminate model forecasts generated by models that are designed to handle seasonal data.

At 606, the set of model forecasts may be reduced based on one or more forecast quality tests. Forecast quality tests may take a variety of forms. For example, forecast quality tests may analyze missing values of model forecasts. For example, model forecasts may be filtered from the set if the model forecasts have missing values in an area of interest (e.g., a forecast horizon). In another example, a model forecast may be filtered from the set if it is missing more than a particular % of values in the forecast horizon.

At 608, the set of model forecasts may be reduced based on redundancy tests. A redundancy test may analyze models associated with model forecasts nodes to identify robust models, and those models having a high degree of redundancy (e.g., models that are producing forecasts that are statistically too similar). Model forecasts having a high degree of redundancy may be excluded from the combined model being generated.

In addition to generating a combined forecast, certain statistics for a combined forecast may be determined. For example, a prediction error variance estimate may be calculated. The prediction error variance estimate may incorporate pair-wise correlation estimates between the individual forecast prediction errors for the predictions that make up the combined forecast and their associated prediction error variances.

Figure 7:
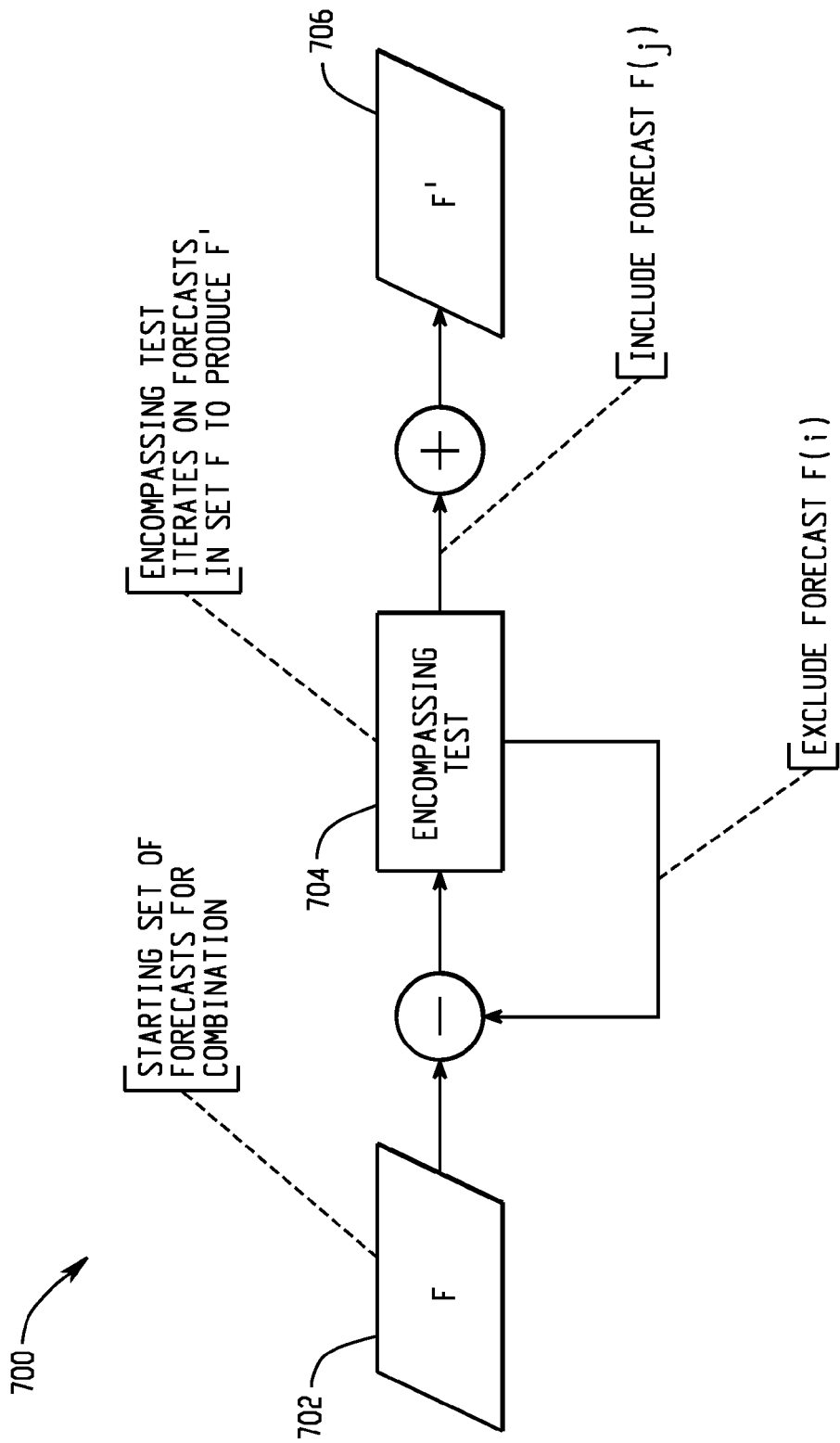
FIG. 7 is a flow diagram depicting an example redundancy test in the form of an encompassing test.

FIG. 7 is a flow diagram depicting an example redundancy test in the form of an encompassing test. The set of model forecasts is shown at 702. At 704, each model in the set 702 is analyzed to determine whether the current model forecast is redundant (e.g., whether the information in the current model forecast is already represented in the continuing set of forecasts 706). If the current model forecast is redundant, then it is excluded. If the current model forecast is not redundant, then it remains in the set of forecasts 706.

With reference back to FIG. 6, at 610, weights are assigned to the model forecasts remaining in the set. Weights may be assigned using a number of different algorithms. For example, weights may be assigned as a straight average of the set of remaining model forecasts, or more complex processes may be implemented, such as a least absolute deviation procedure. At 612, the weighted model forecasts are aggregated to generate a combined forecast.

Figure 8:
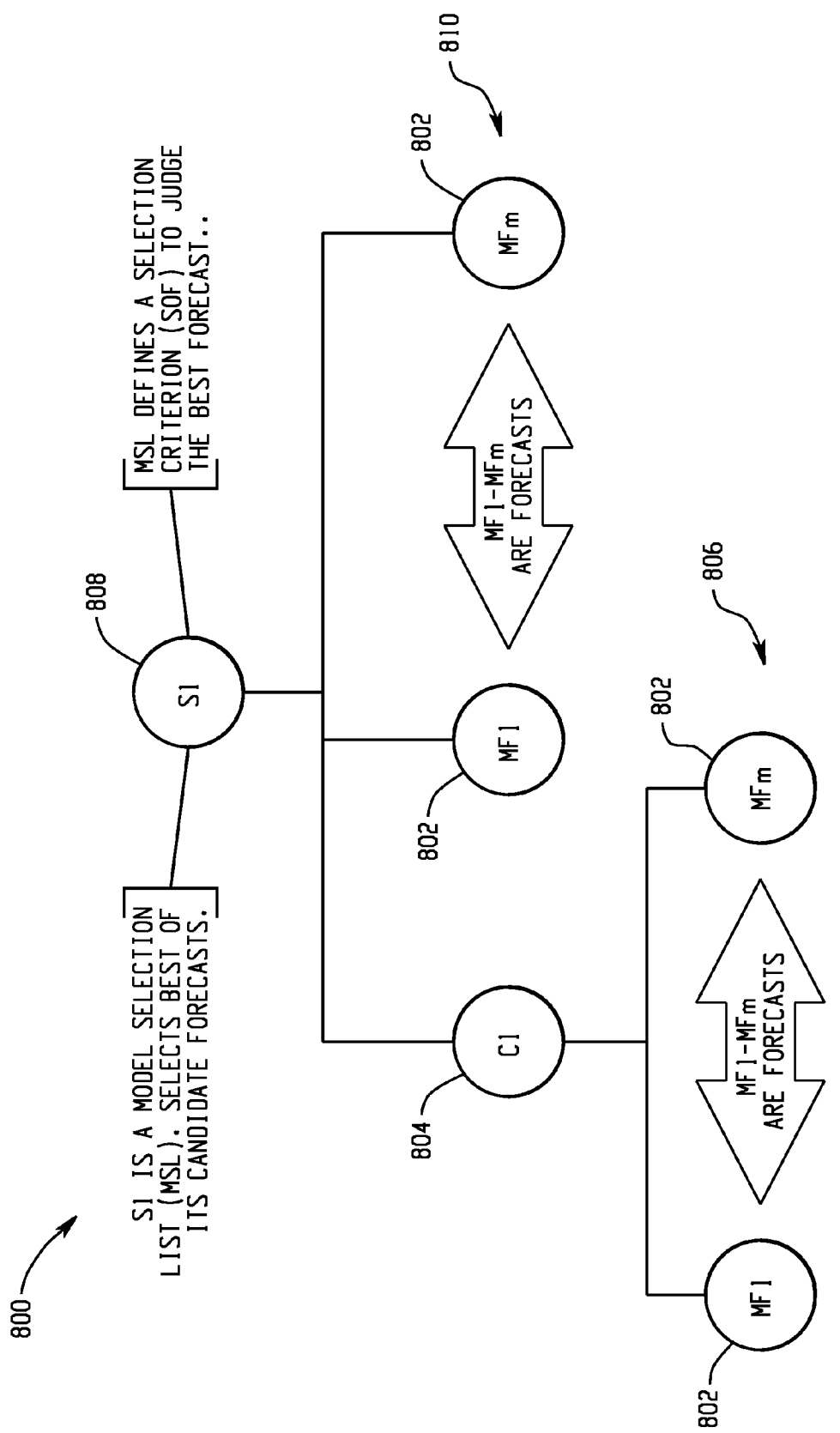
FIG. 8 depicts a forecast model selection graph having a selection node as a root node.

FIG. 8 depicts a forecast model selection graph having a selection node as a root node. A number of node forecasts 802 are resolved (e.g., by generating node forecasts using a model, accessing externally generated forecasts from computer memory). A combination node 804 combines the model forecasts of child nodes 806 of the combination node 804. A selection node 808 selects a forecast from among the combination node 804 and model forecasts at child nodes 810 of the selection node 808 based on a selection criteria.

Figure 9:
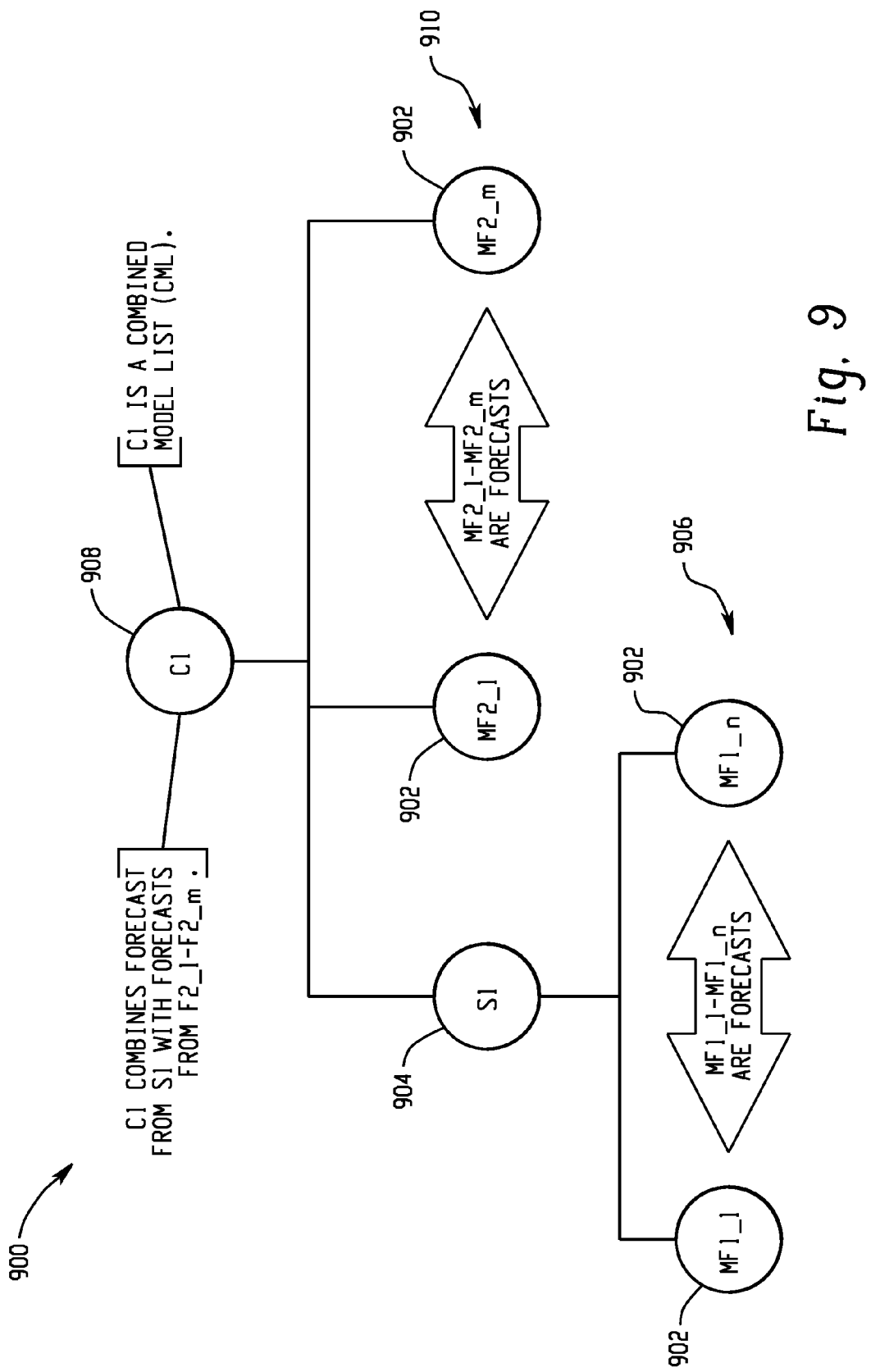
FIG. 9 depicts a forecast model selection graph having a combination node as a root node.

FIG. 9 depicts a forecast model selection graph having a combination node as a root node. A number of node forecasts 902 are resolved (e.g., by generating node forecasts using a model, accessing externally generated forecasts from memory). A selection node 904 selects a model forecast from the child nodes 906 of the selection node. A combination node 908 combines the model forecast from the selection node 904 and model forecasts at child nodes 910 of the combination node 908 to generate a combined forecast.

Figure 10:
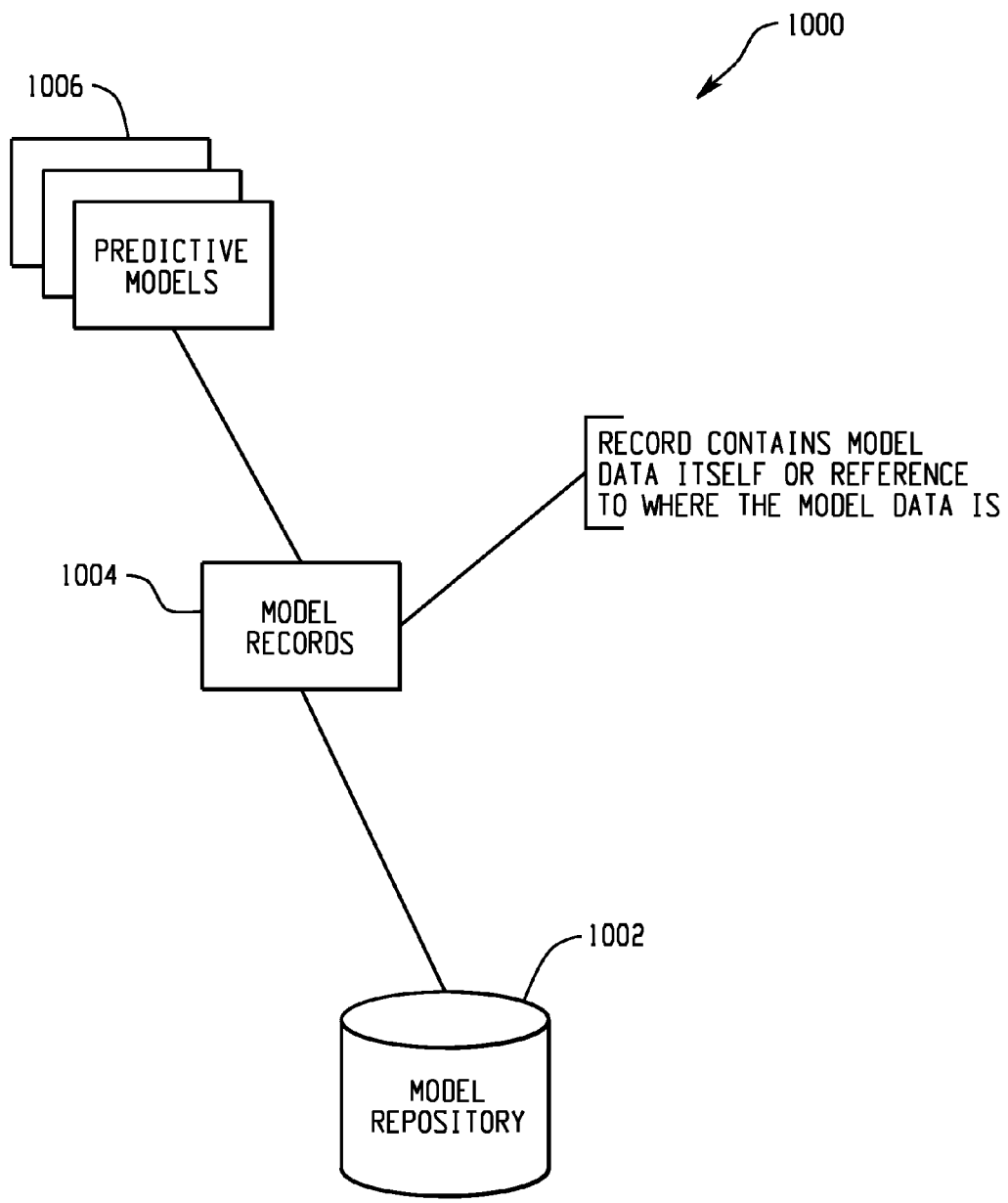
FIG. 10 depicts an example model repository for storing predictive models.

As noted previously, a model forecast node may be associated with a predictive model that is used to generate a model forecast for the model forecast node. In one embodiment, the predictive models may be stored in a model repository for convenient access. FIG. 10 depicts an example model repository for storing predictive models. The model repository 1002 includes a number of model records 1004. A model record may contain model data for implementing a predictive model 1006. In another embodiment, a model record 1004 may contain a reference to where data for implementing the predictive model 1006 can be found (e.g., a file location, a pointer to a memory location, a reference to a record in a database). Other example details of a model repository are described in U.S. Pat. No. 7,809,729, entitled "Model Repository," the entirety of which is herein incorporated by reference.

Figure 11:
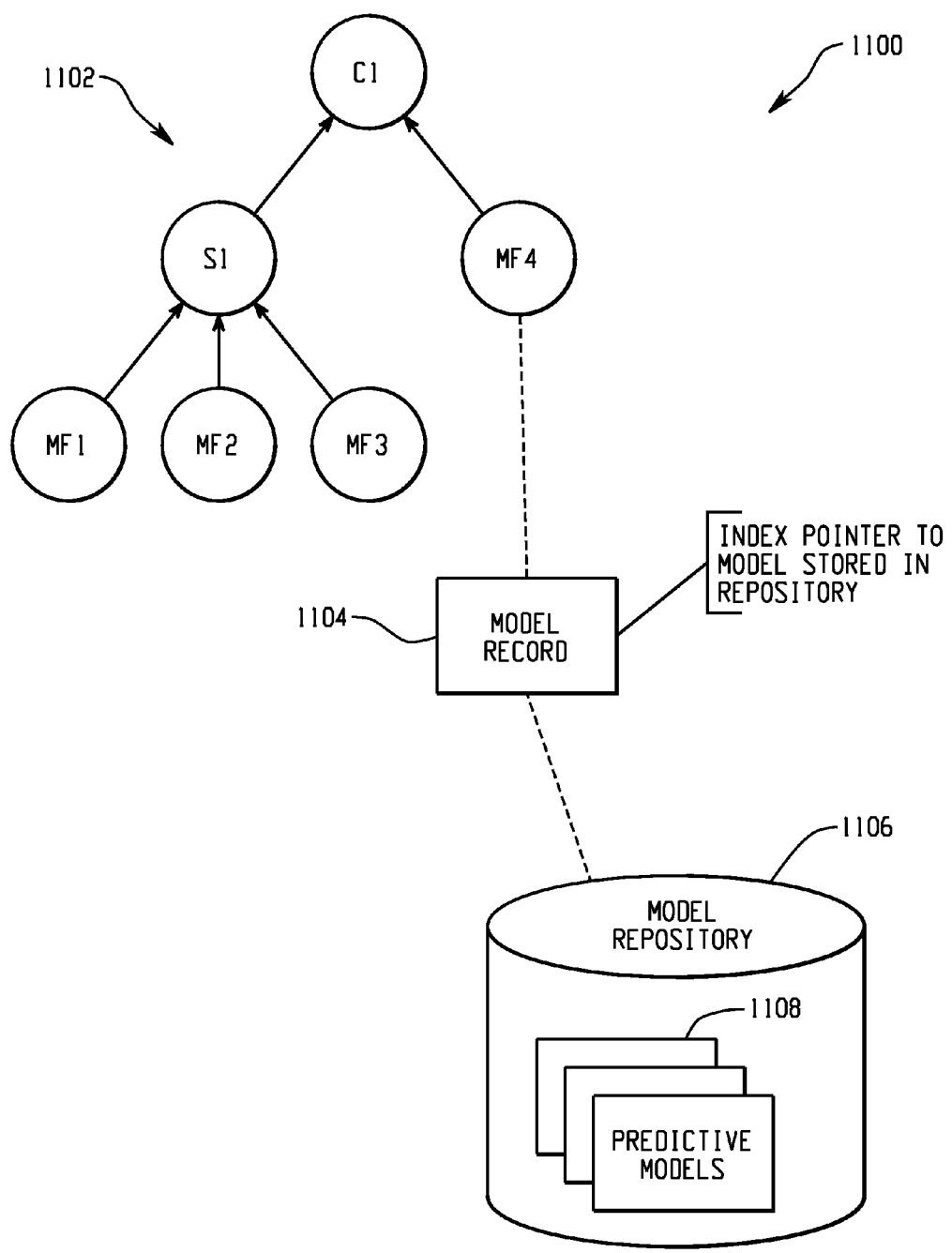
FIG. 11 depicts a link between a forecast model selection graph and a model repository.

A model repository configuration may streamline the data contained in a forecast model selection graph. FIG. 11 depicts a link between a forecast model selection graph and a model repository. A forecast model selection graph 1102 includes a number of model forecast nodes MF1, MF2, MF3, MF4, a selection node S1, and a combination node C1. The model forecast nodes are resolved to generate node forecasts. One of the model forecast nodes, MF4, is associated with a model record 1104. For example, model forecast node, MF4, may contain an index value for the model record 1104. The model record is stored in the model repository 1104 and may contain data for implementing a predictive model to generate the node forecast, or the model record may contain a reference to the location of such data 1108, such as a location in a the model repository 1106. When the model forecast node, MF4, is to be resolved, the model record 1104 is located based on the index identified by the model forecast node, MF4. Data for the desired predictive model 1108 to be used to generate the node forecast is located in the model repository 1106 based on data contained in the model record 1104.

Figure 12:
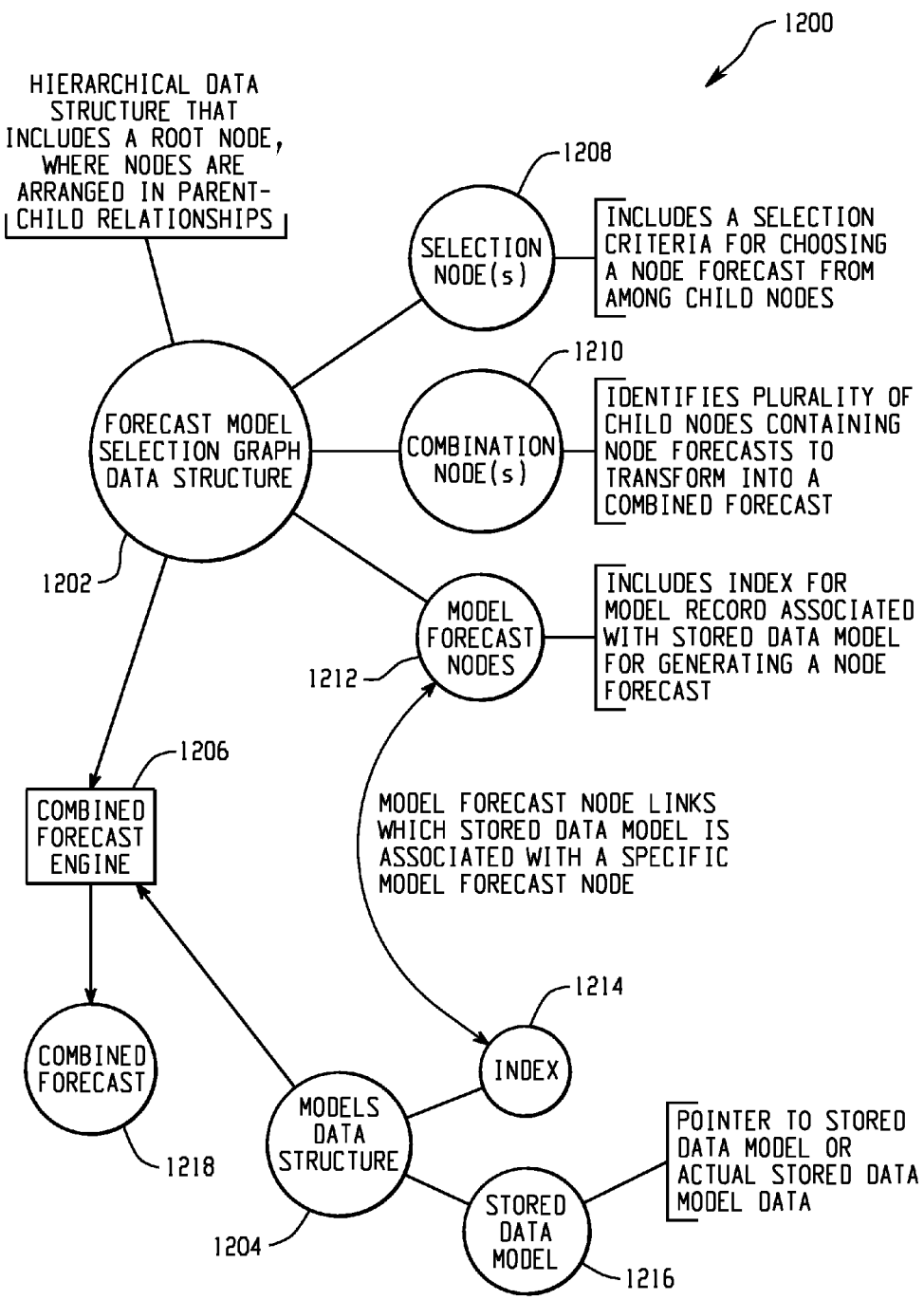
FIG. 12 is a diagram depicting relationships among a forecast model selection graph data structure, a models data structure, and a combined forecast engine.

FIG. 12 is a diagram depicting relationships among a forecast model selection graph data structure, a models data structure, and a combined forecast engine. A forecast model selection graph data structure 1202 and a models data structure 1204 may be stored on one or more computer-readable storage mediums for access by an application program, such as a combined forecast engine 1206 being executed on one or more data structures. The data structures 1202, 1204 may be used as part of a process for evaluating a physical process with respect to one or more attributes of the physical process by combining forecasts for the one or more physical process attributes. Physical process data generated over time (e.g., time series data) may be used in the forecasts for the one or more physical attributes.

The forecast model selection graph data structure 1202 may contain data about a hierarchical structure of nodes which specify how forecasts for the one or more physical attributes are combined, where the hierarchical structure of nodes has a root node, and where the nodes include one or more selection nodes 1208, one or more model combination nodes 1210, and model forecast nodes 1212. The forecast model selection graph data structure 1202 may include selection node data 1208 that specifies, for the one or more model selection nodes, model selection criteria for selecting, based upon model forecasting performance, models associated with the model forecast nodes or the one or more model combination nodes. The forecast model selection graph data structure 1202 may also include model combination node data 1210 that specifies, for the one or more model combination nodes, which of the forecasts generated by the model forecast nodes are to be combined.

The forecast model selection graph data structure 1202 may also include model forecast node data 1212 that specifies, for the model forecast nodes, which particular predictive data models contained in the models data structure are to be used for generating forecasts. For example, the model forecast node data 1212 may link which stored data model is associated with a specific model forecast node, such as via an index 1214. The stored data model 1216 identified by the model forecast node data 1212 may be accessed as part of a resolving process to generate a node forecast for a particular node of the model forecast selection graph. The combined forecast engine 1206 may process the forecast model selection graph data structure 1202, using stored data models 1216 identified by the models data structure 1204 via the link between the model forecast node data 1212 and the models data structure 1204 to generate a combined forecast 1218.

Figure 13:
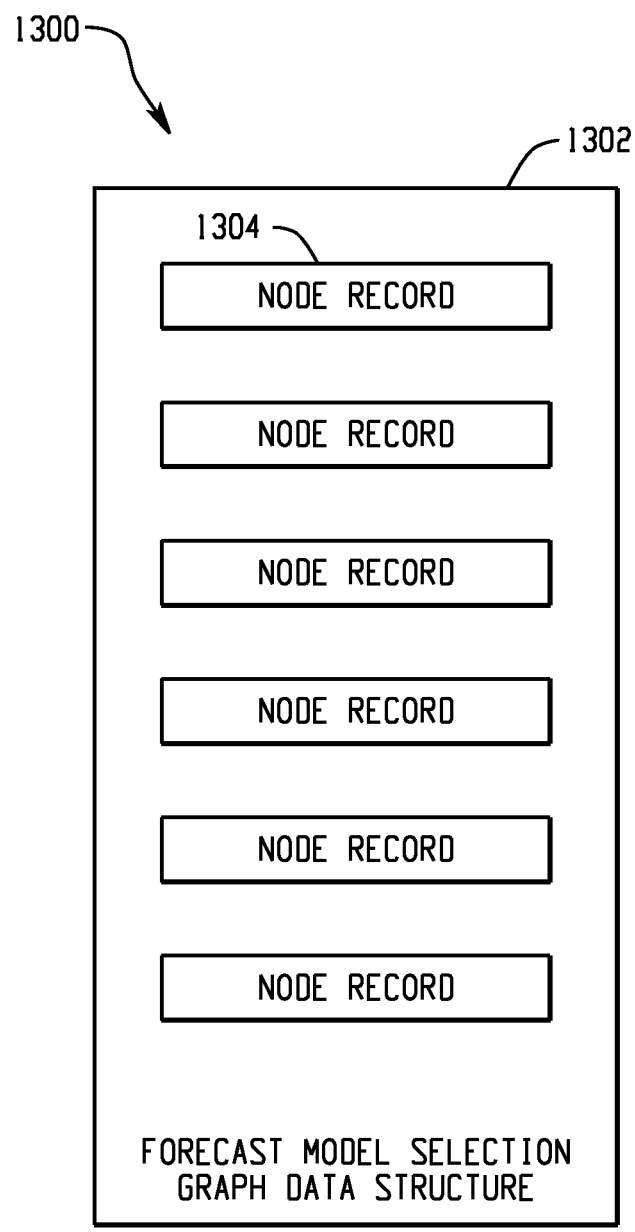
FIG. 13 depicts an example forecast model selection graph data structure.

FIG. 13 depicts an example forecast model selection graph data structure. In FIG. 13, the forecast model selection graph data structure 1302 is a data structure that includes a number of node records 1304 as sub-data structures. The node records 1304 may each be descriptive of a model forecast node, a combination node, or a selection node. Each of the node records 1304 includes data.

Figure 14:
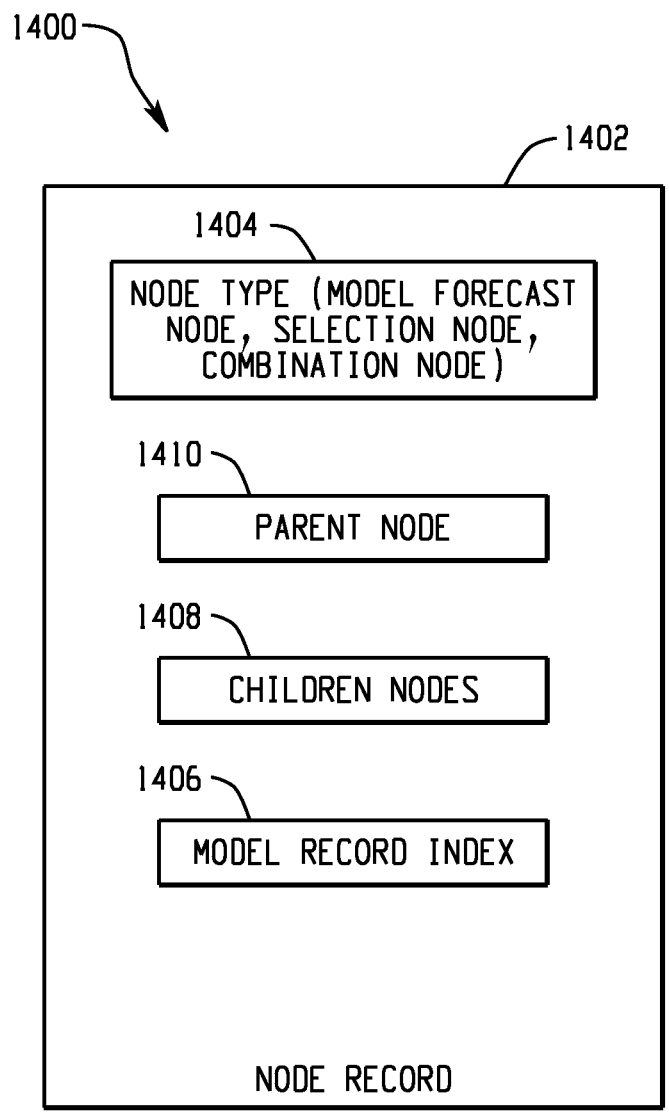
FIG. 14 depicts an example node record.

FIG. 14 depicts an example node record. For example, the node record 1402 may contain data related to the type of a node 1404 and data for the node to be processed, such as an identification of a model to generate a node forecast 1406 or a selection criteria for selecting among child nodes. Additionally, a node record 1402 may include structure data that identifies, in whole or in part, a position of a node in the forecast model selection graph. For example, the node record data may contain data identifying child nodes 1408 of a node and a parent node 1410 of the node. The node record 1402 may also identify a node as a root or a leaf node or the exact position of a node in the forecast model selection graph hierarchy (e.g., a pre-order or a post-order value).

Figure 15:
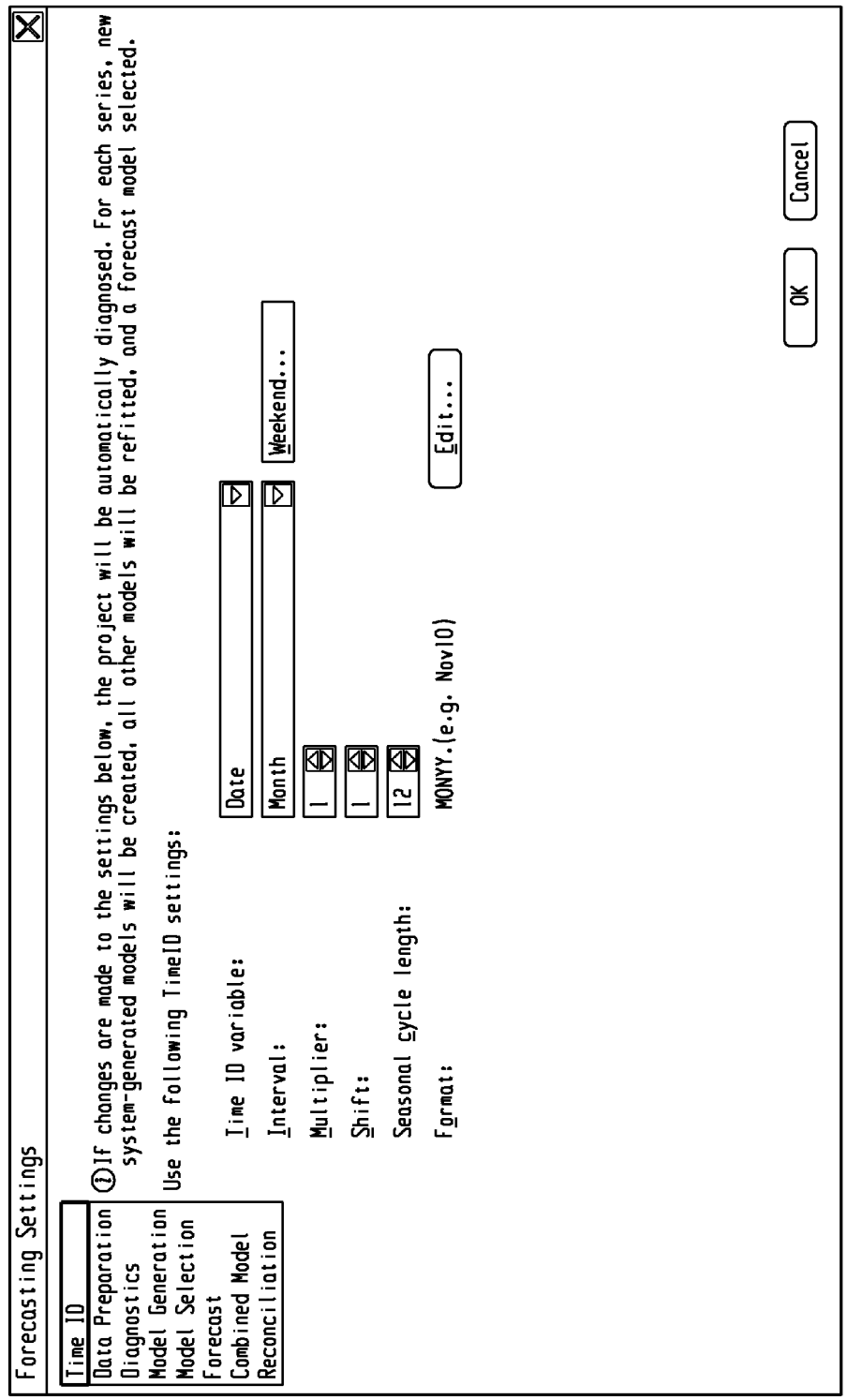

FIGS. 15-32 depict graphical user interfaces that may be used in generating and comparing combined forecasts. FIG. 15 depicts an example graphical user interface for identifying parameters related to time, where a user may specify parameters such as a time interval, a multiplier value, a shift value, a seasonal cycle length, and a date format.

Figure 16:
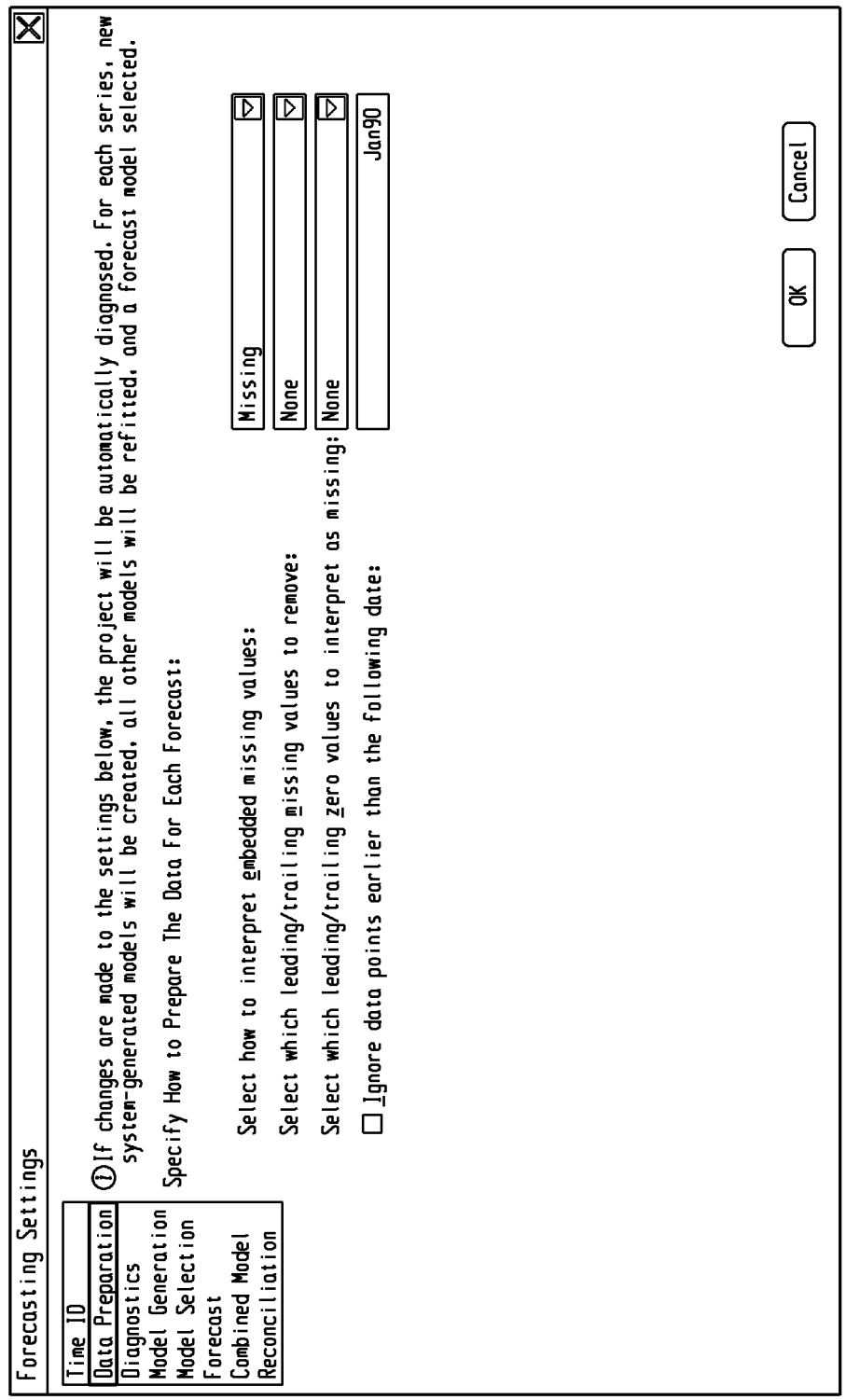

FIG. 16 depicts an example forecasting settings graphical user interface for identifying parameters related to data preparation, where a user may specify how to prepare data for forecasting. Example settings include how to interpret embedded missing values, which leading or trailing missing values to remove, which leading or trailing zero values to interpret as missing, and whether to ignore data points earlier than a specified date.

Figure 17:
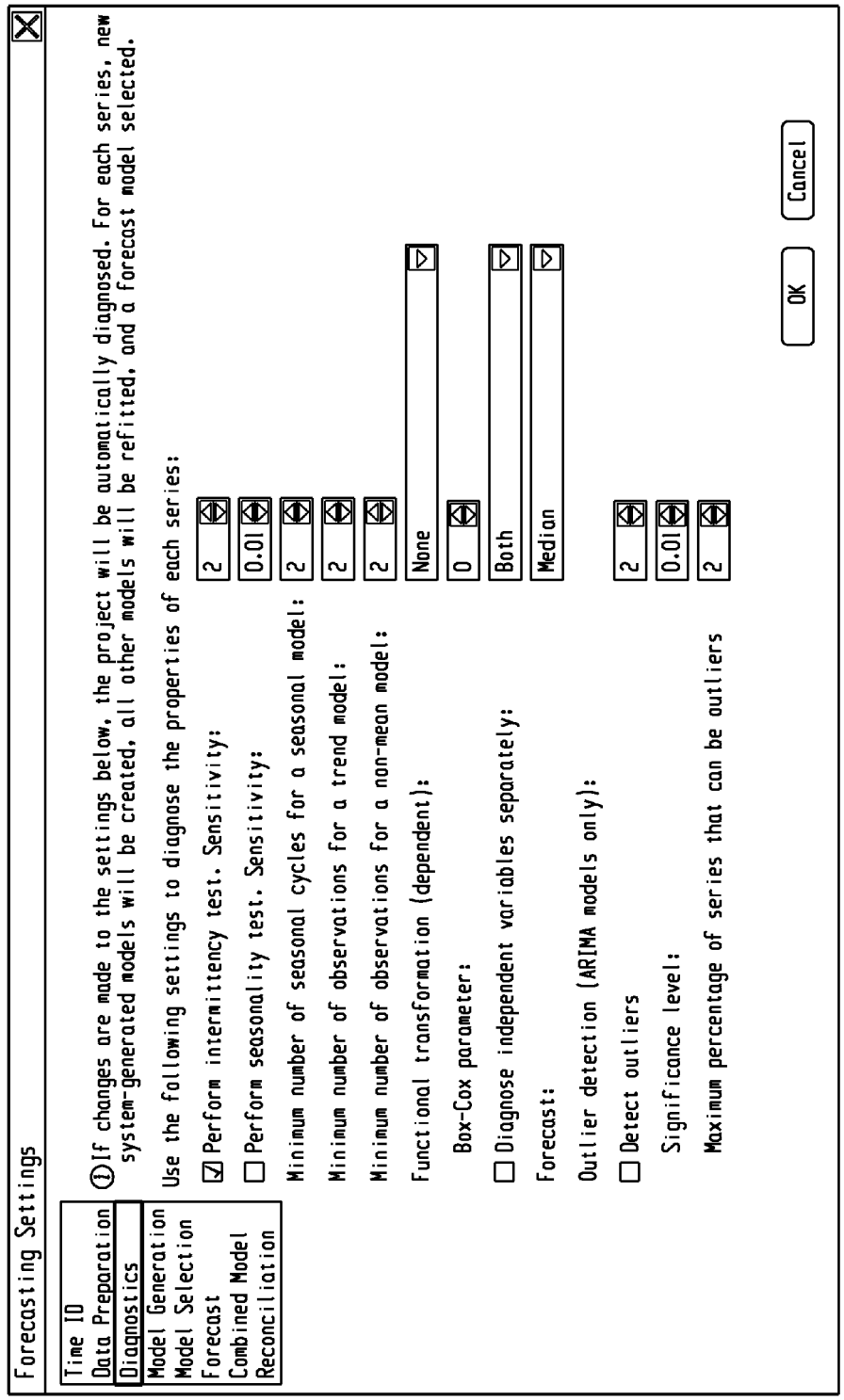

FIG. 17 depicts an example forecasting settings graphical user interface for identifying diagnostics settings. Example settings include intermittency test settings, seasonality test settings, independent variable diagnostic settings, and outlier detection settings. Such diagnostic settings may be used in a variety of contexts, including processing of combination nodes of a forecast model selection graph.

Figure 18:
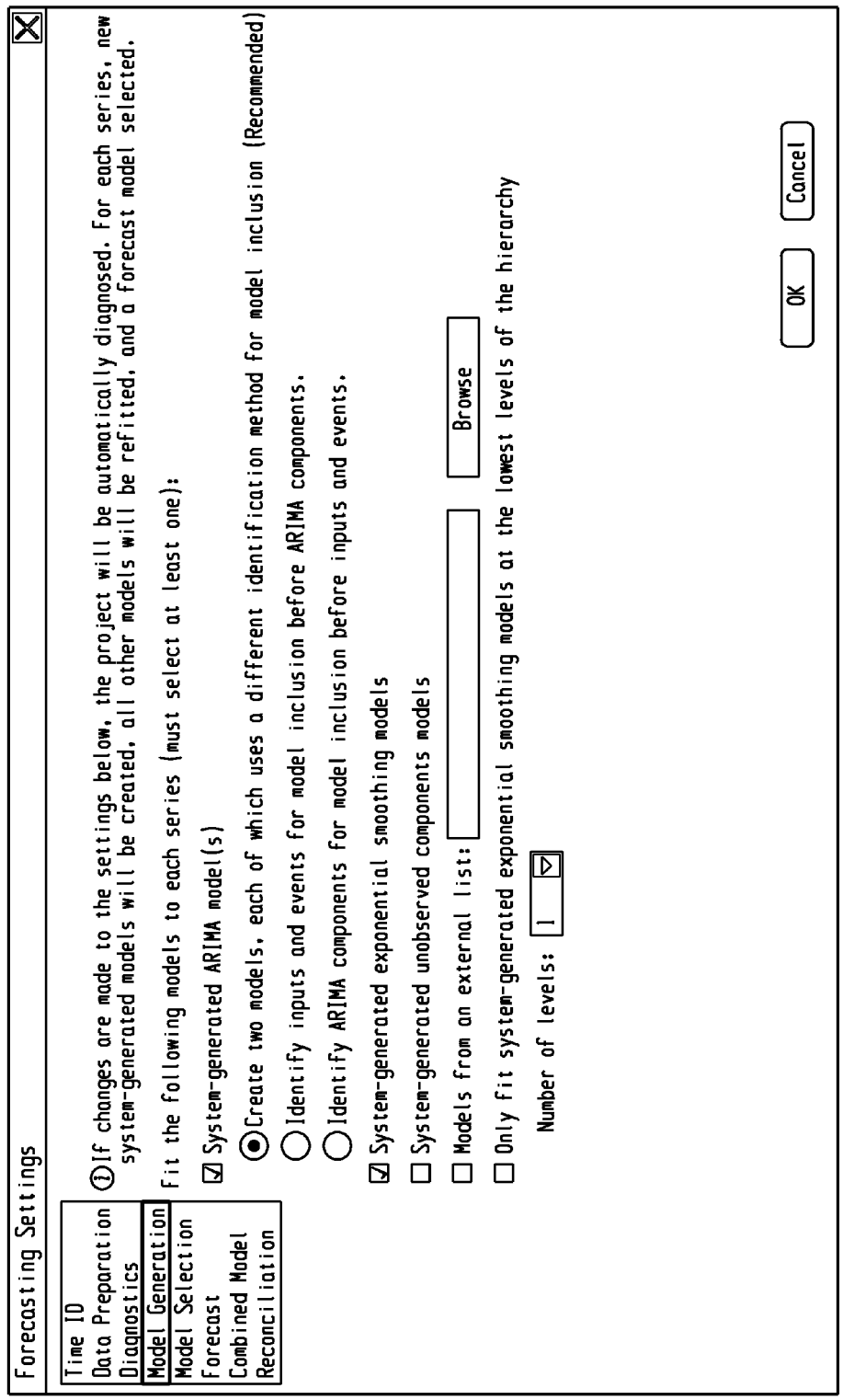

FIG. 18 depicts an example forecasting settings graphical user interface for identifying model generation settings. Example settings include identifications of which models to fit to each time series. Example models include system-generated ARIMA models, system-generated exponential smoothing models, system-generated unobserved components models, and models from an external list. Such model generation settings may be used in a variety of contexts, including with model forecast nodes of a forecast model selection graph.

Figure 19:
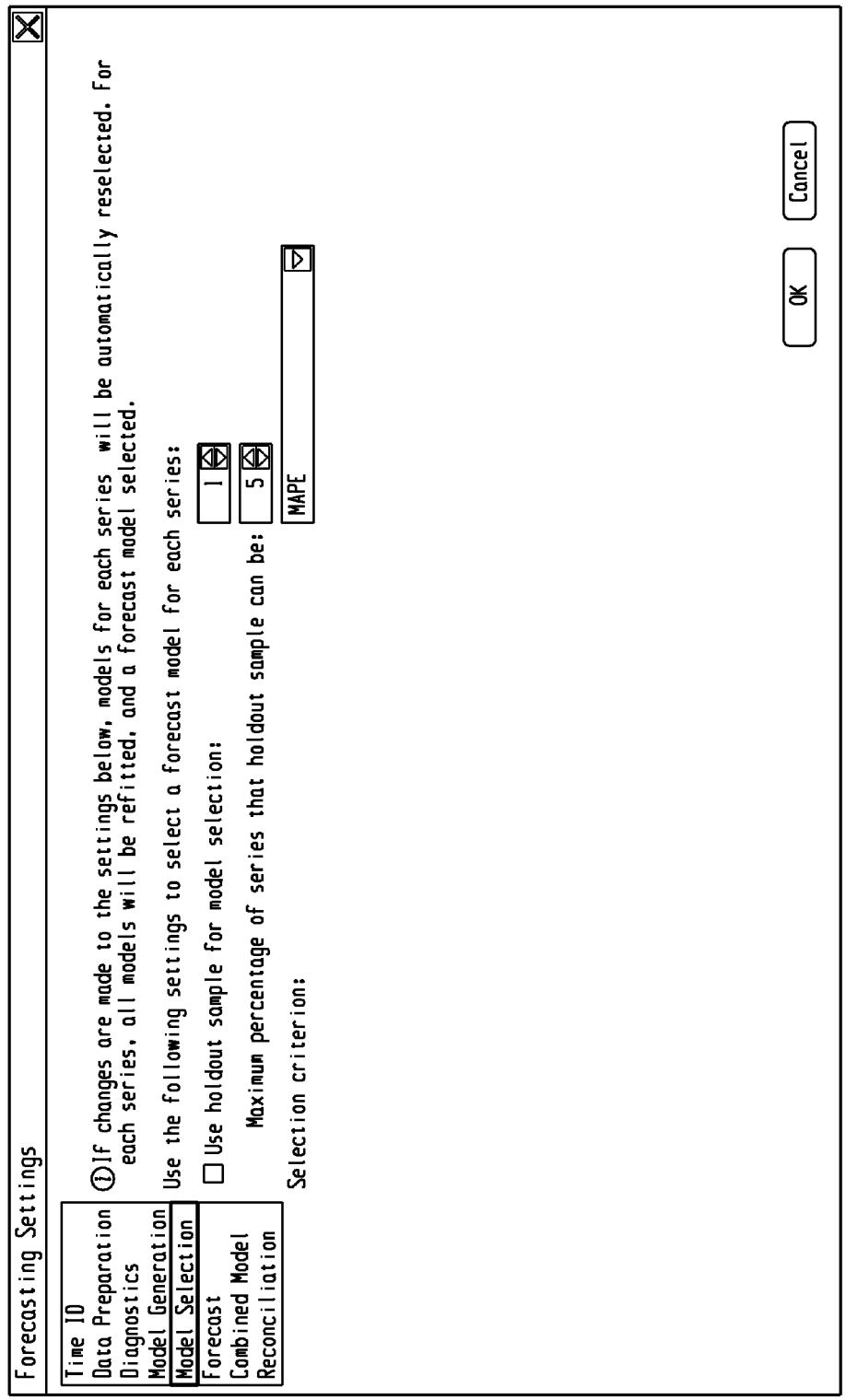

FIG. 19 depicts an example forecasting settings graphical user interface for identifying model selection settings. Example settings include whether to use a holdout sample in performing model selection and a selection criteria for selecting a forecast. Such model selection settings may be used in a variety of contexts, including with model selection nodes of a forecast model selection graph.

Figure 20:
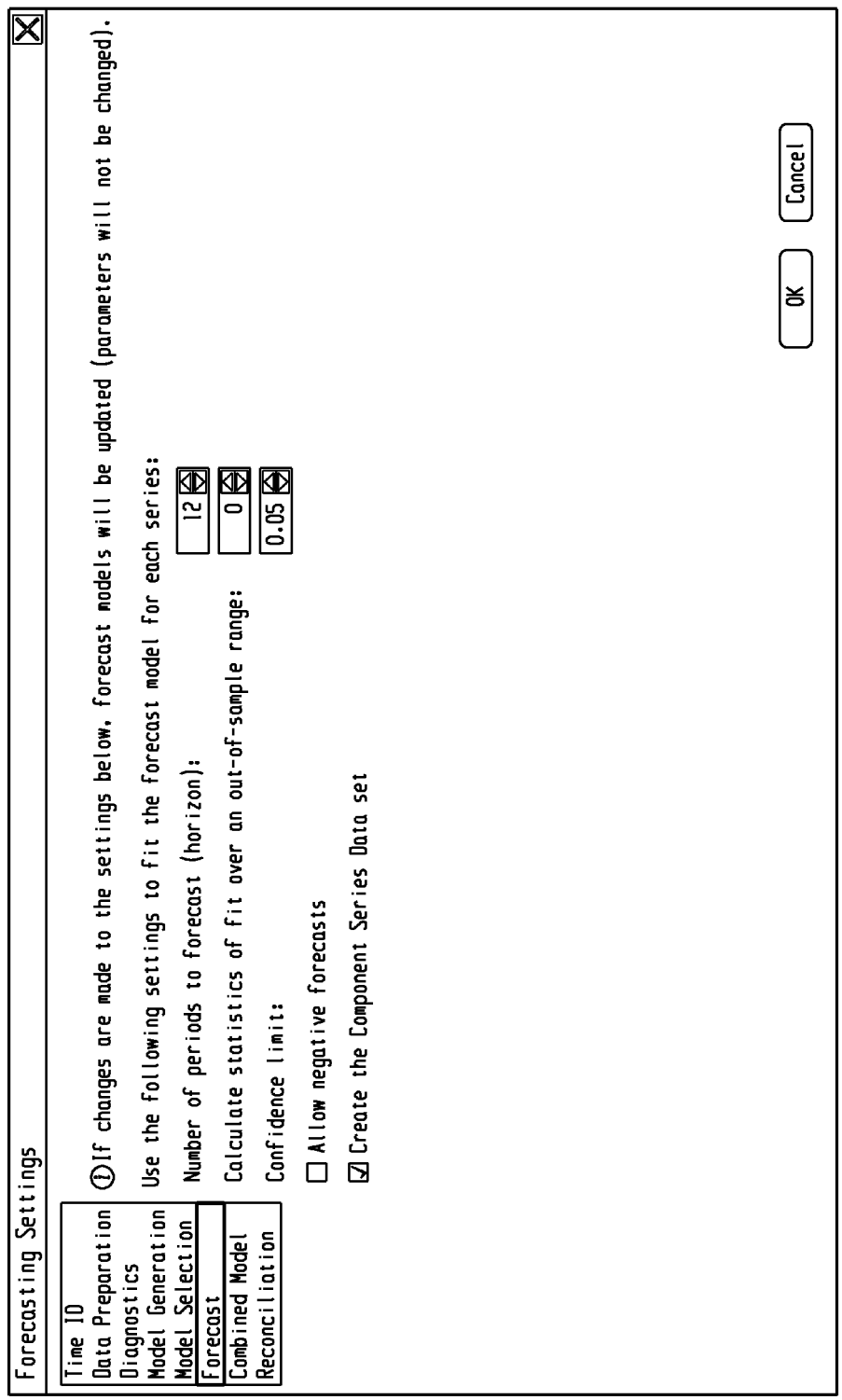

FIG. 20 depicts an example forecasting settings graphical user interface for identifying model forecast settings. Example settings include a forecast horizon, calculation of statistics of fit settings, confidence limit settings, negative forecast settings, and component series data set settings.

Figure 21:
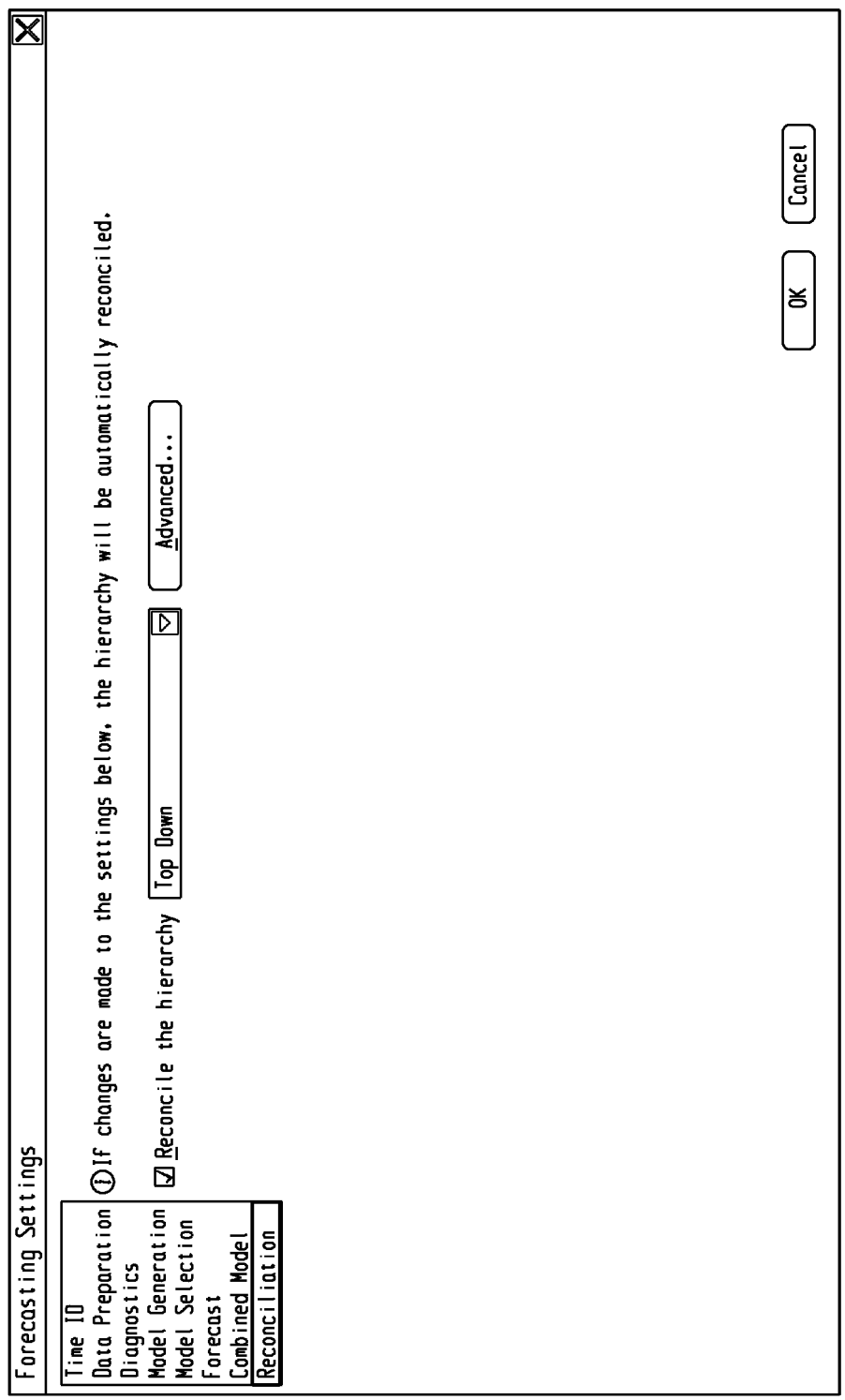

FIG. 21 depicts an example forecasting settings graphical user interface for identification of hierarchical forecast reconciliation settings. Using the user interface of FIG. 21, a preference for reconciliation of a forecast hierarchy may be selected along with a method for performing the reconciliation, such as a top-down, bottom-up, or middle-out process.

Figure 22:
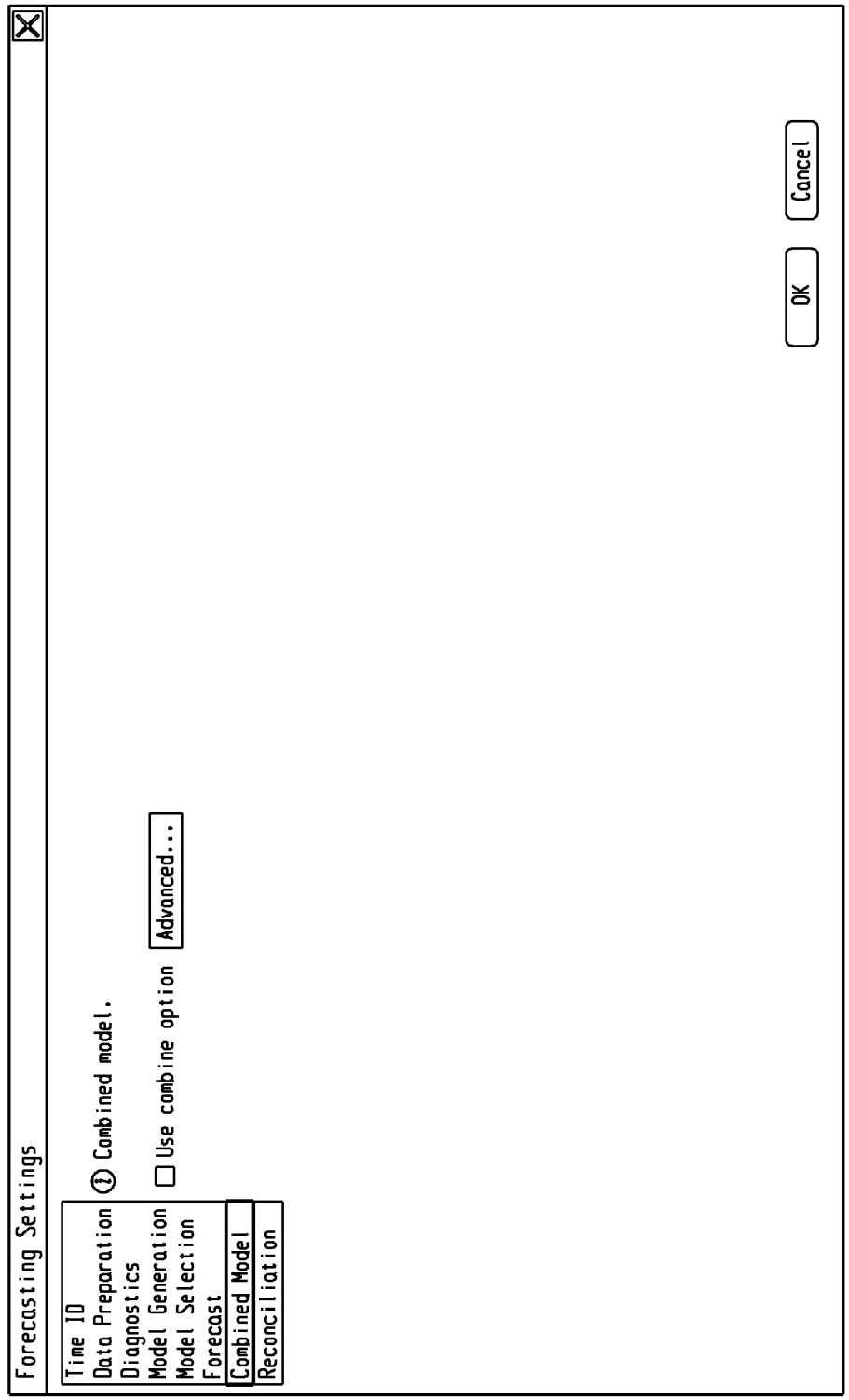
Figure 23:
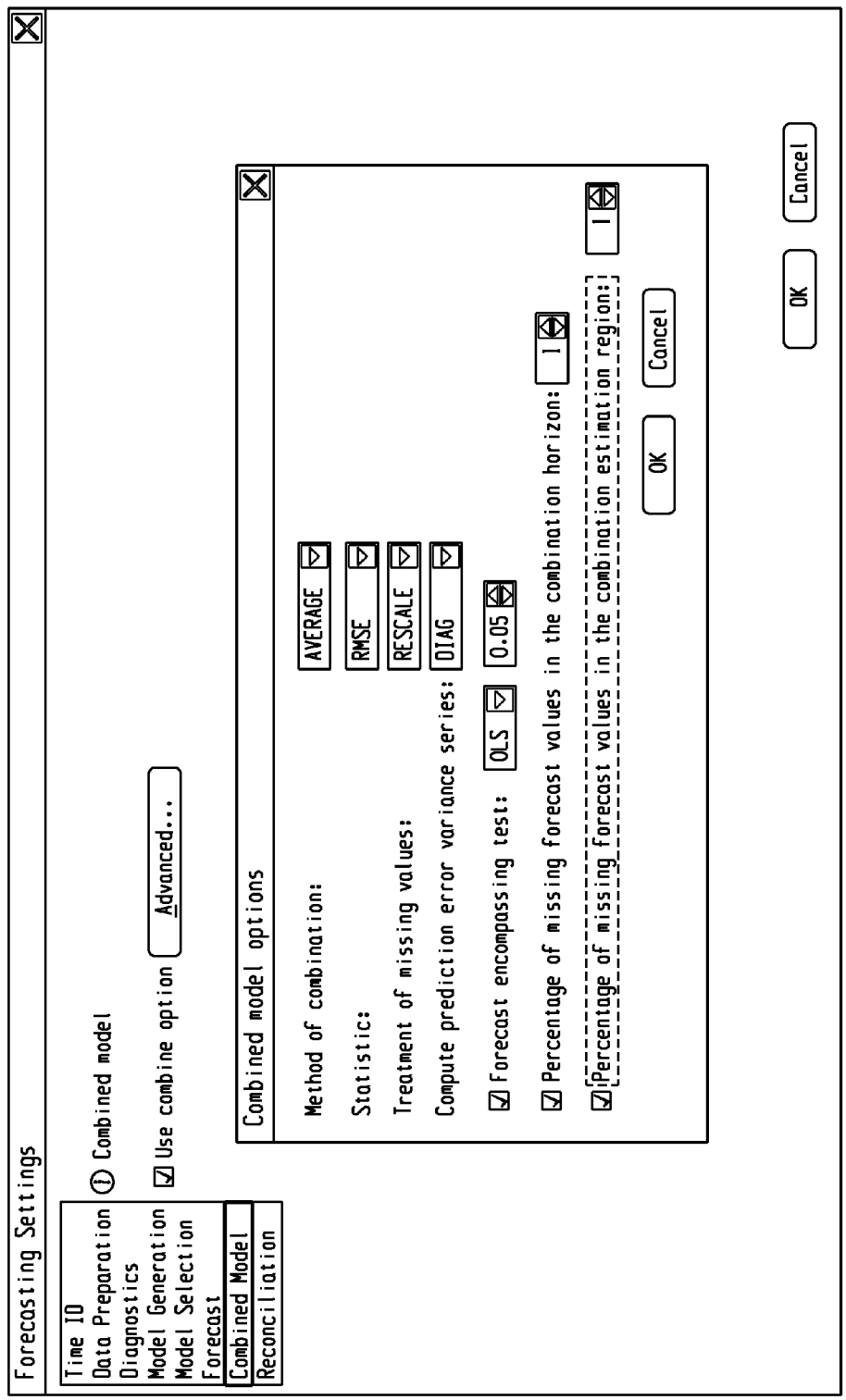

FIG. 22 depicts an example forecasting settings graphical user interface for combined model settings. The combined model settings user interface allows selection of a combine model option. The user interface of FIG. 22 also includes an advanced options control. FIG. 23 depicts an example graphical user interface for specification of advanced combined model settings. The settings of FIG. 23 may be used in a variety of contexts, including in processing of a combination node of a forecast model selection graph.

Example settings for advanced combined model settings include a method of combination setting. Example parameters include a RANKWGT setting, where a combined forecast engine analyzes the forecasts to be combined and assigns weights to those forecasts based on the analysis. In another example, the RANKWGT option may accept a set of user-defined weights that are substituted for the automatic rank weight settings for each ordinal position in the ranked set. The combined forecast engine analyzes and ranks the forecasts to be combined and then assigns the user-defined weights to the forecasts according to the forecast's ordinal position in the ranking. As another option, a user may directly assign weights to the individual forecasts, and as a further option, a mean-average of the individual forecasts may be utilized.

The advanced settings interface also includes an option for directing that a forecast encompassing test be performed. When selected, the combined forecast engine ranks individual forecasts for pairwise encompassing elimination. The advanced setting interface further includes options related to treatment of missing values. For example, a rescale option may be selected for weight methods that incorporate a sum-to-one restriction for combination weights. A further option directs a method of computation of prediction error variance series. This option is an allowance for treating scenarios where the cross-correlation between two forecast error series is localized over segments of time when it is assumed that the error series are not jointly stationary. DIAG may be the default setting, while ESTCORR presumes that the combination forecast error series are jointly stationary and estimates the pairwise cross-correlations over the complete time spans.

Figure 24:
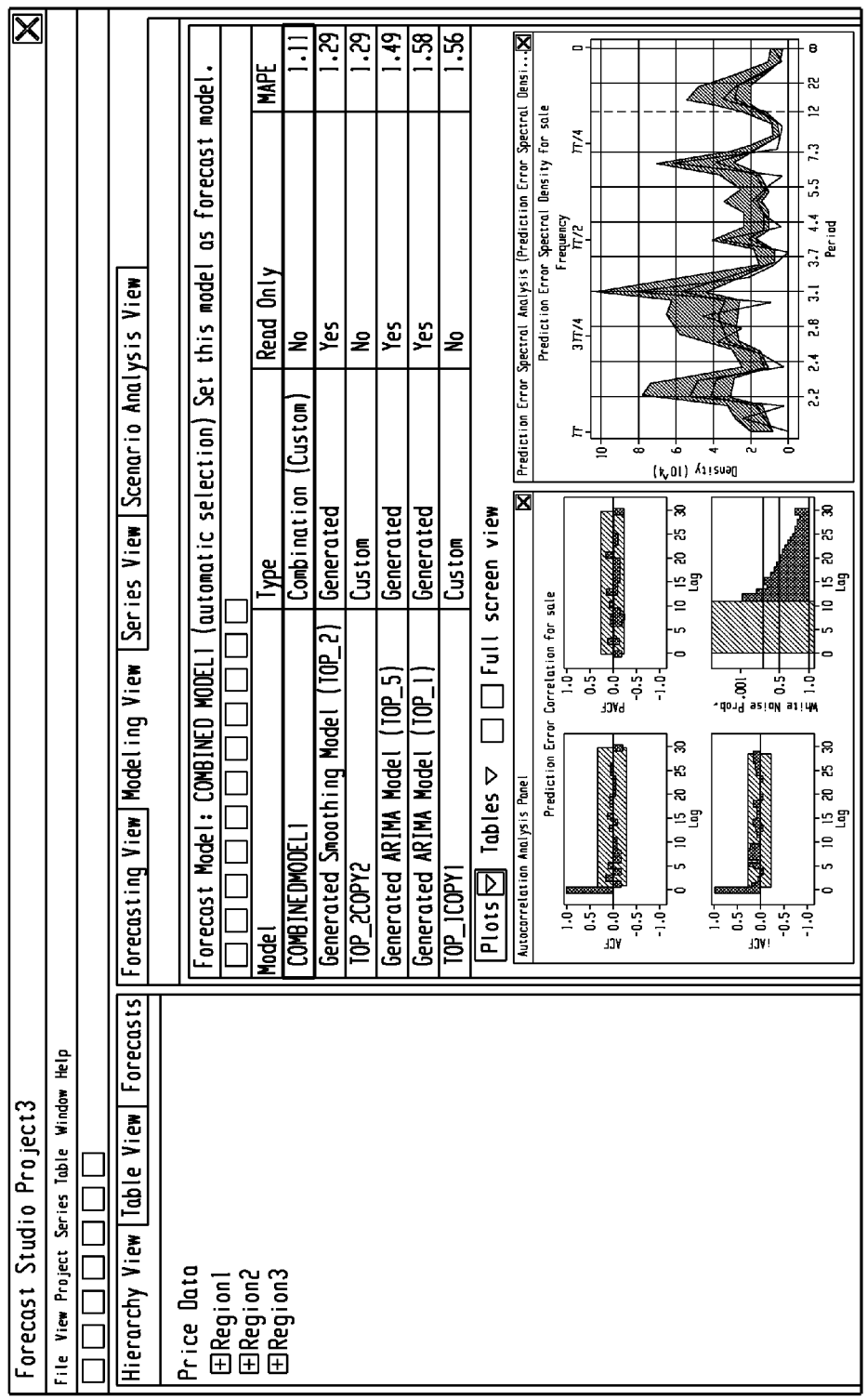

FIG. 24 depicts a model view graphical user interface. Using the model view, a user can evaluate combined model residuals. The user interface is configured to enable graphical analysis of a model residual series plot, residual distribution, time domain analysis (e.g., ACF, PACF, IACF, white noise), frequency domain analysis (e.g., spectral density, periodogram). The user interface also enables exploration of parameter estimates, statistics of fit (e.g., RMSE, MAPE, AIC), and bias statistics. FIG. 25 depicts example graphs that may be provided by a model view graphical interface. Other options provided by a model view graphical user interface may include options for managing model combinations, such as adding a model for consideration, editing a previously added model, copying a model, and deleting a model (e.g., a previously added combined model).

FIG. 26 depicts an example graphical user interface for manually defining a combined model. For example, a manually defined combined model may be utilized with a model forecast node in a forecast model selection graph. The graphical user interface may be configured to receive a selection of one or more models to be combined, weights to be applied to those combined models in generating the combination, as well as other parameters. For example, FIG. 27 depicts the manual entry of ranked weights to be applied to the selected models after they are ranked by a combined forecast engine.

Figure 28:
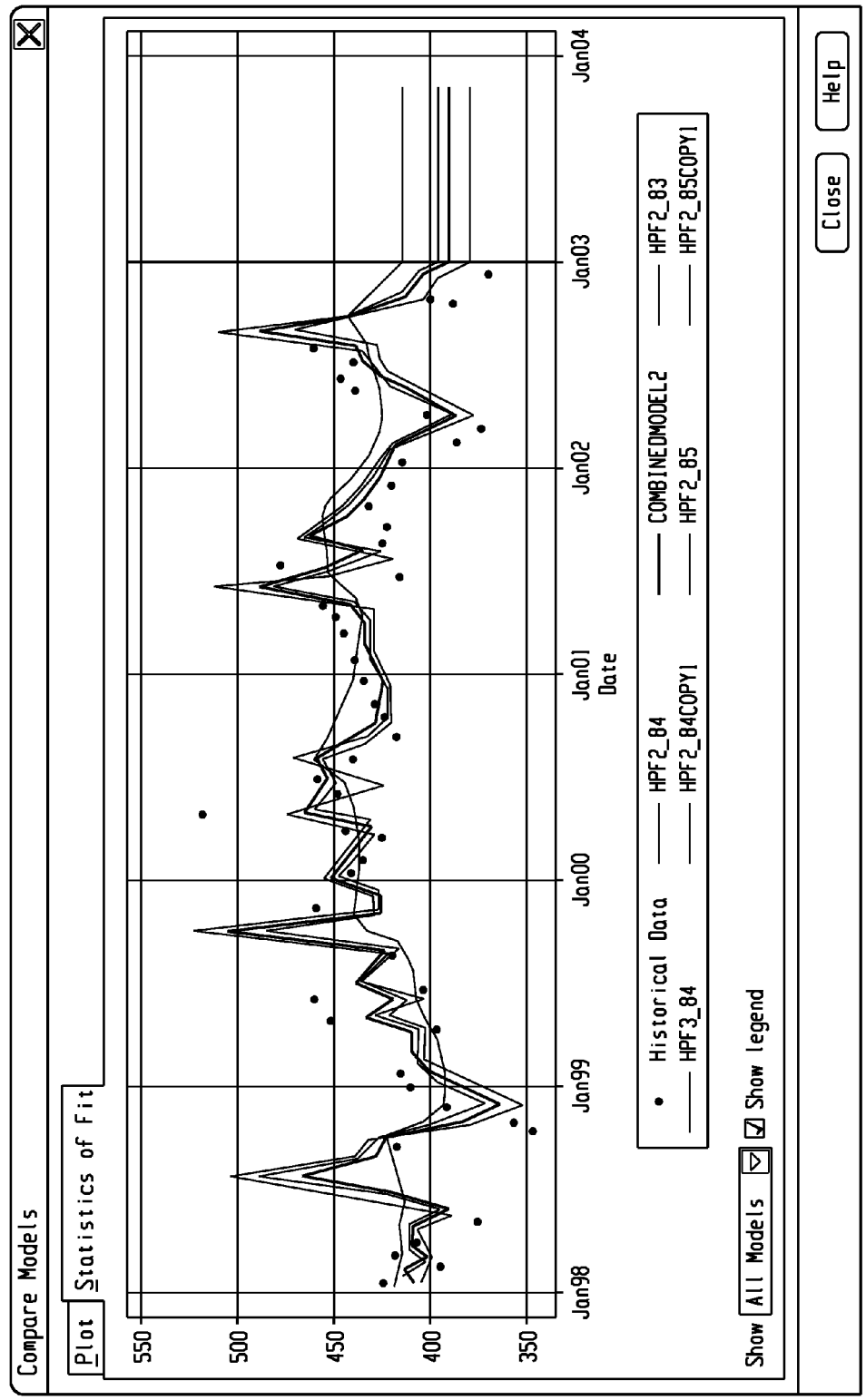

FIG. 28 depicts an example interface for comparing models. The example interface may be accessed via a model view interface. The present interface enables comparison of selected model combinations in graphical form. FIG. 29 depicts a table that enables comparison of selected model combinations statistically in text form.

Figure 30:
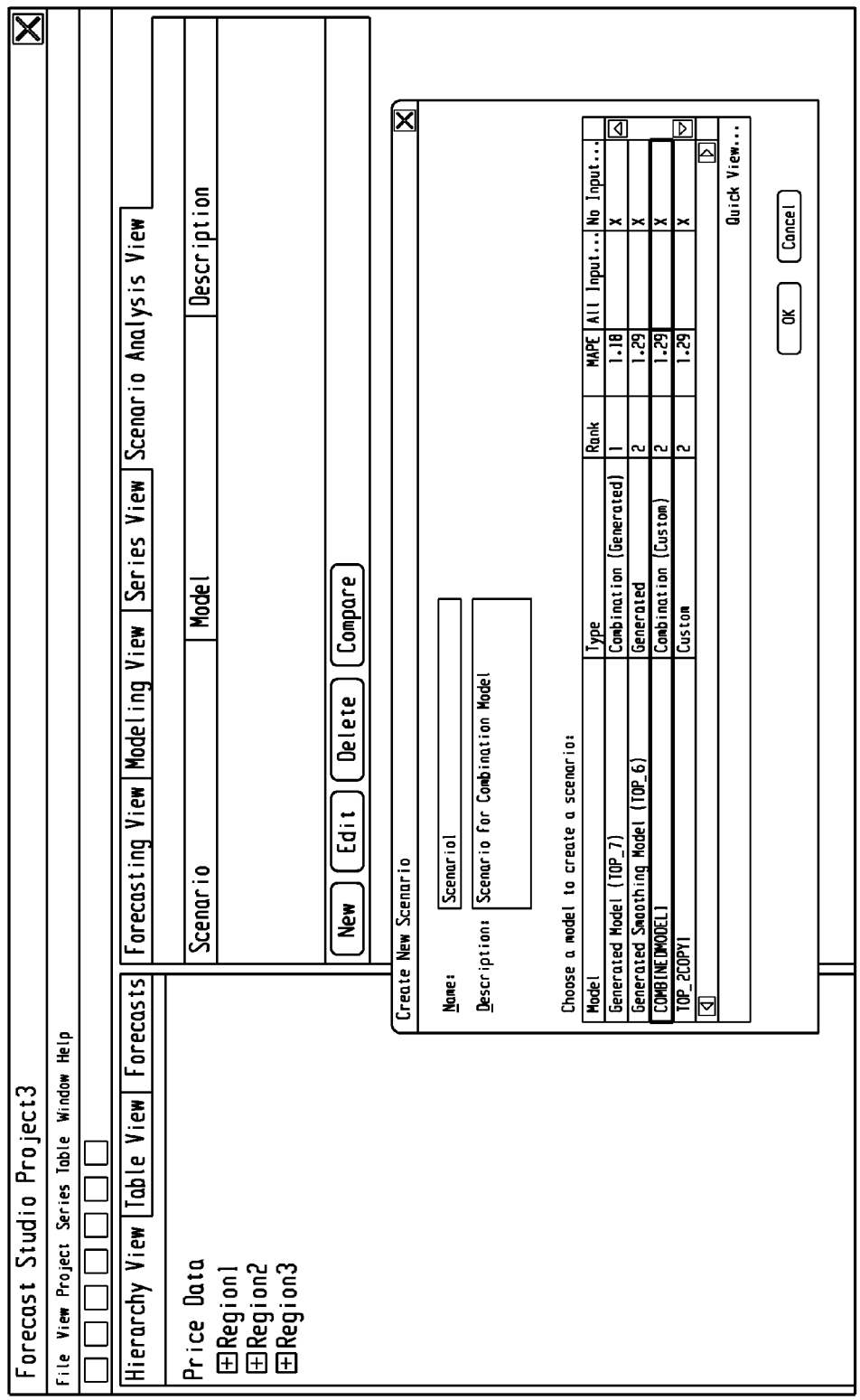
Figure 32:
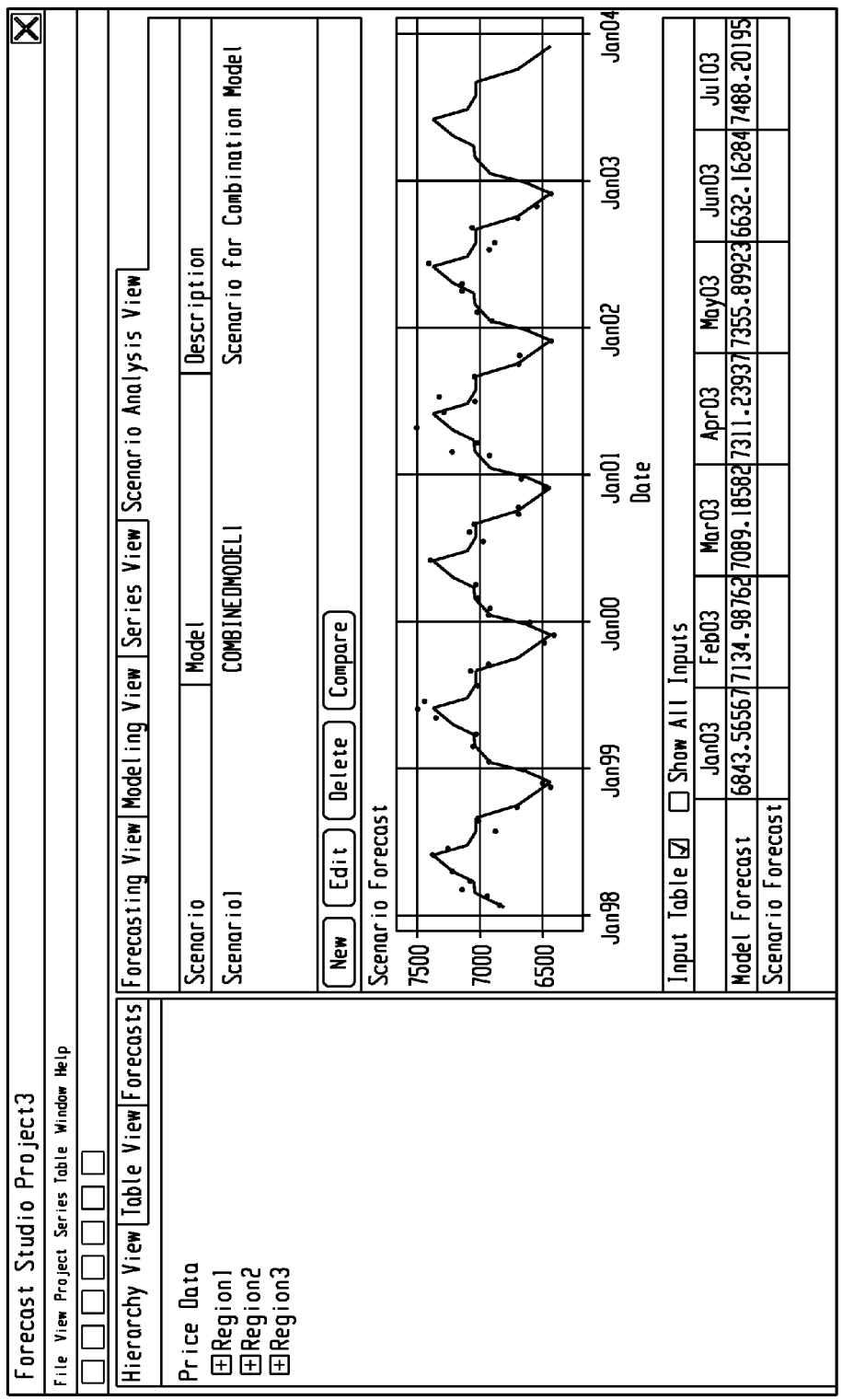

FIG. 30 depicts a graphical user interface for performing scenario analysis using model combinations. Using scenario analysis, scenarios can be generated, where an input time series can be varied to better understand possible future outcomes and to evaluate a model's sufficiency to different input values. A create new scenario menu may be accessed by selecting a new control in a scenario analysis view. Using the create new scenario menu, shown in further detail in FIG. 31, a model is selected for analysis. A scenario is generated, and a graph depicting results of the scenario analysis is displayed, such as the graph of FIG. 32.

The systems and methods described herein may, in some implementations, be utilized to achieve one or more of the following benefits. For example, forecast accuracy may often be significantly improved by combining forecasts of individual predictive models. Combined forecasts also tend to produce reduced variability compared to the individual forecasts that are components of a combined forecast. The disclosed combination process may automatically generate forecast combinations and vet them against other model and expert forecasts as directed by the forecast model selection graph processing. Combined forecasts allow for better predicting systematic behavior of an underlying data generating process that cannot be captured by a single model forecast alone. Frequently, combinations of forecasts from simple models outperform a forecast from a single, complex model.

Figure 33A:
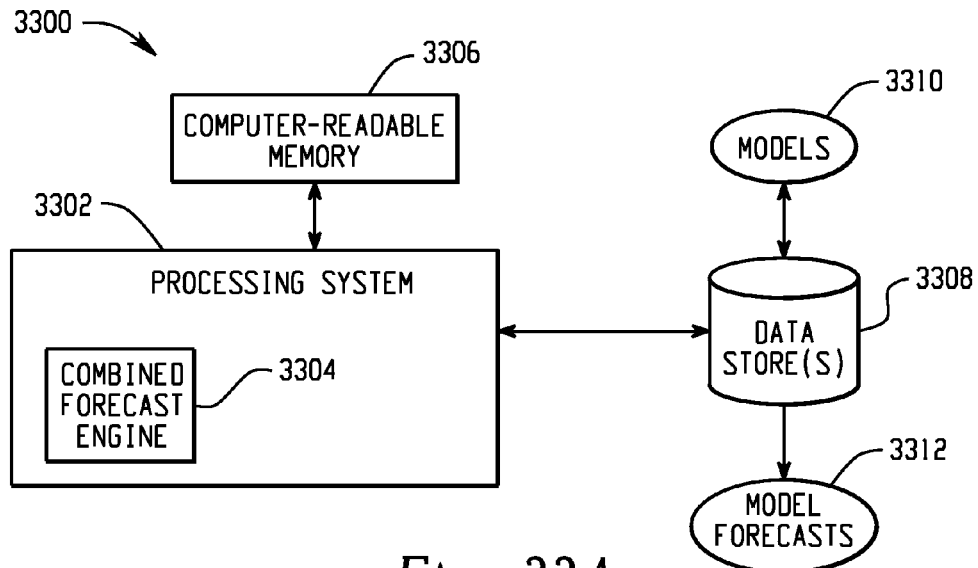
FIGS. 33A, 33B, and 33C depict example systems for use in implementing combined forecast engine.
Figure 33B:
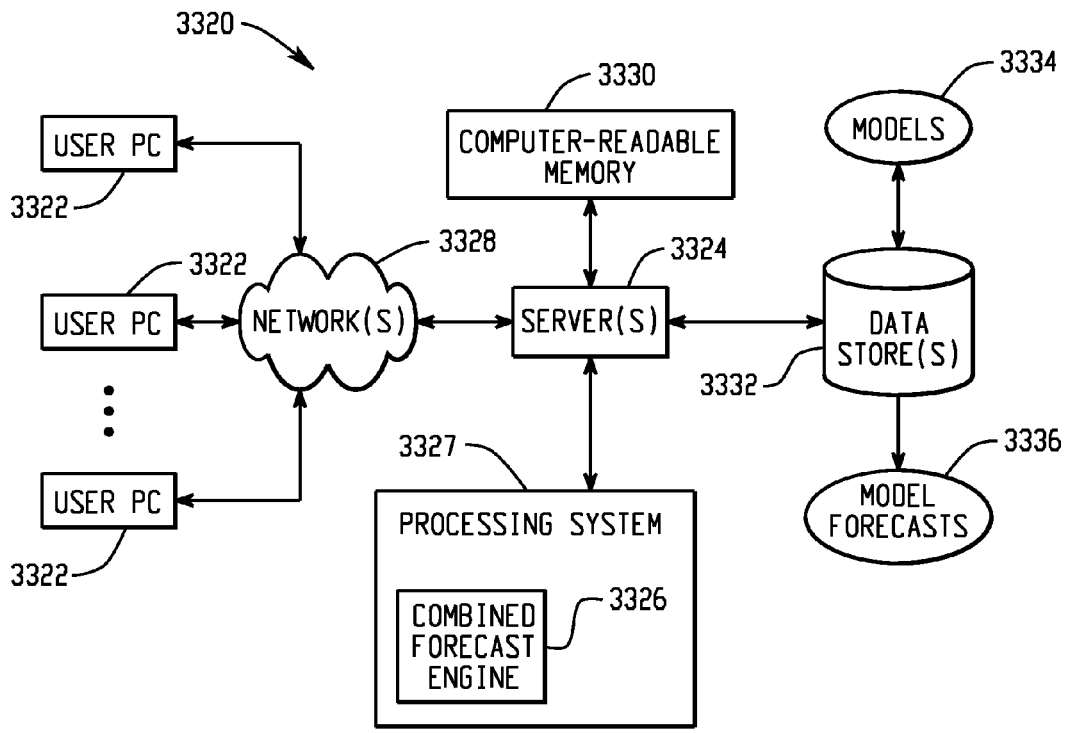
Figure 33C:
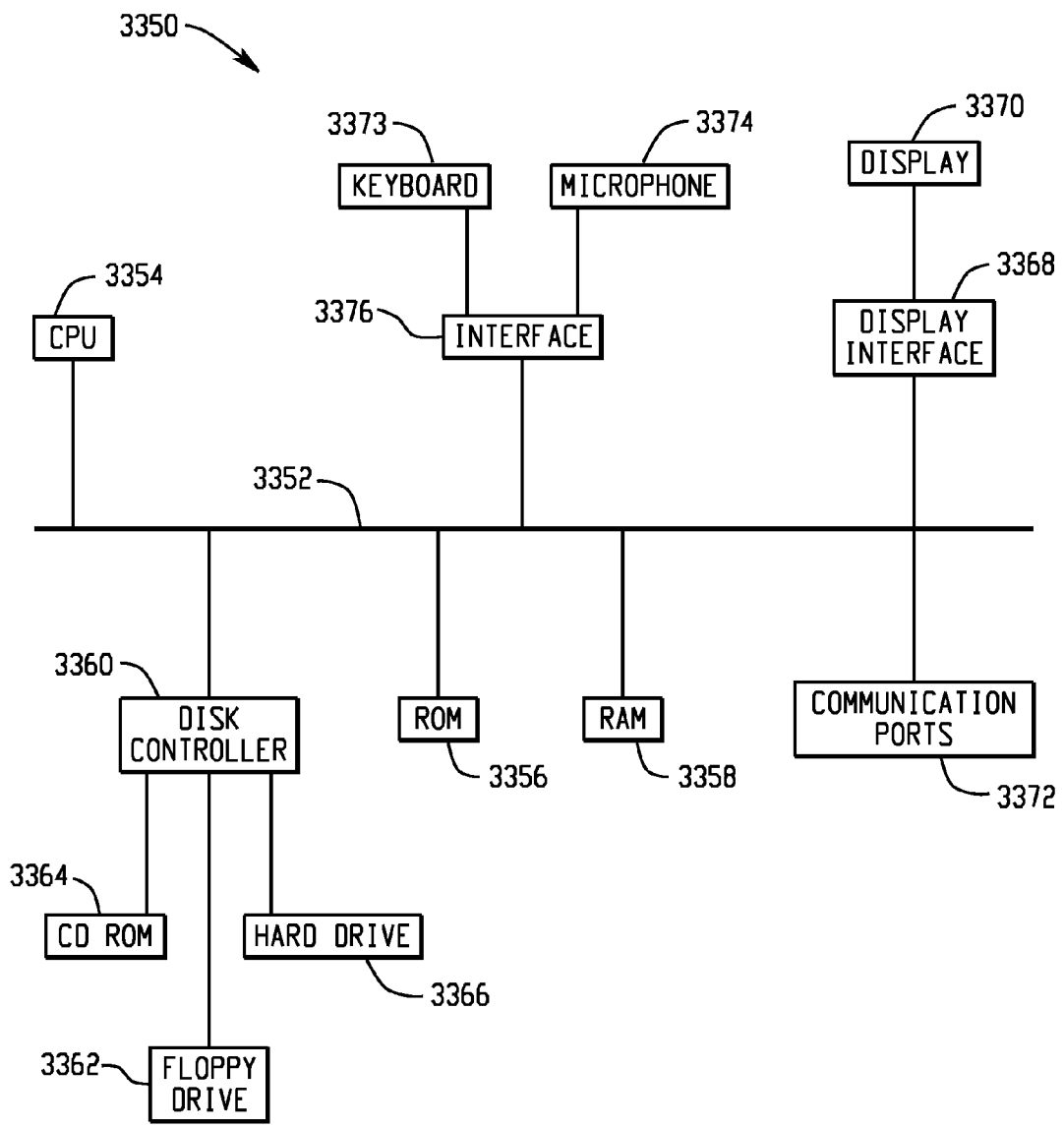

FIGS. 33A, 33B, and 33C depict example systems for use in implementing an enterprise data management system. For example, FIG. 33A depicts an exemplary system 3300 that includes a standalone computer architecture where a processing system 3302 (e.g., one or more computer processors) includes a combined forecast engine 3304 being executed on it. The processing system 3302 has access to a computer-readable memory 3306 in addition to one or more data stores 3308. The one or more data stores 3308 may include models 3310 as well as model forecasts 3312.

FIG. 33B depicts a system 3320 that includes a client server architecture. One or more user PCs 3322 accesses one or more servers 3324 running a combined forecast engine 3326 on a processing system 3327 via one or more networks 3328. The one or more servers 3324 may access a computer readable memory 3330 as well as one or more data stores 3332. The one or more data stores 3332 may contain models 3334 as well as model forecasts 3336.

FIG. 33C shows a block diagram of exemplary hardware for a standalone computer architecture 3350, such as the architecture depicted in FIG. 33A that may be used to contain and/or implement the program instructions of system embodiments of the present invention. A bus 3352 may serve as the information highway interconnecting the other illustrated components of the hardware. A processing system 3354 labeled CPU (central processing unit) (e.g., one or more computer processors), may perform calculations and logic operations required to execute a program. A processor-readable storage medium, such as read only memory (ROM) 3356 and random access memory (RAM) 3358, may be in communication with the processing system 3354 and may contain one or more programming instructions for performing the method of implementing a combined forecast engine. Optionally, program instructions may be stored on a computer readable storage medium such as a magnetic disk, optical disk, recordable memory device, flash memory, or other physical storage medium. Computer instructions may also be communicated via a communications signal, or a modulated carrier wave.

A disk controller 3360 interfaces one or more optional disk drives to the system bus 3352. These disk drives may be external or internal floppy disk drives such as 3362, external or internal CD-ROM, CD-R, CD-RW or DVD drives such as 3364, or external or internal hard drives 3366. As indicated previously, these various disk drives and disk controllers are optional devices.

Each of the element managers, real-time data buffer, conveyors, file input processor, database index shared access memory loader, reference data buffer and data managers may include a software application stored in one or more of the disk drives connected to the disk controller 3360, the ROM 3356 and/or the RAM 3358. Preferably, the processor 3354 may access each component as required.

A display interface 3368 may permit information from the bus 3352 to be displayed on a display 3370 in audio, graphic, or alphanumeric format. Communication with external devices may optionally occur using various communication ports 3372.

In addition to the standard computer-type components, the hardware may also include data input devices, such as a keyboard 3373, or other input device 3374, such as a microphone, remote control, pointer, mouse and/or joystick.

FIGS. 34-41 depict example systems and methods for evaluating the performance of a combined forecast model using rolling simulations. Before using a time series model to forecast a time series, it is often important to evaluate the model's performance by validating the model's ability to forecast previously acquired data. Such performance measures are commonly referred to as ex-ante model performance measures. Ex-ante (i.e., before the fact) model performance measures are similar to ex-post (i.e., after the fact) forecast performance measures; however, ex-post forecast performance measures are used to evaluate the performance of forecasts regardless of the source (e.g., model-based, judgment-based, possible adjustments, etc.) Rolling simulations can be used to perform ex-ante model performance by repeating the analyses over several forecast origins and lead times.

Figure 34:
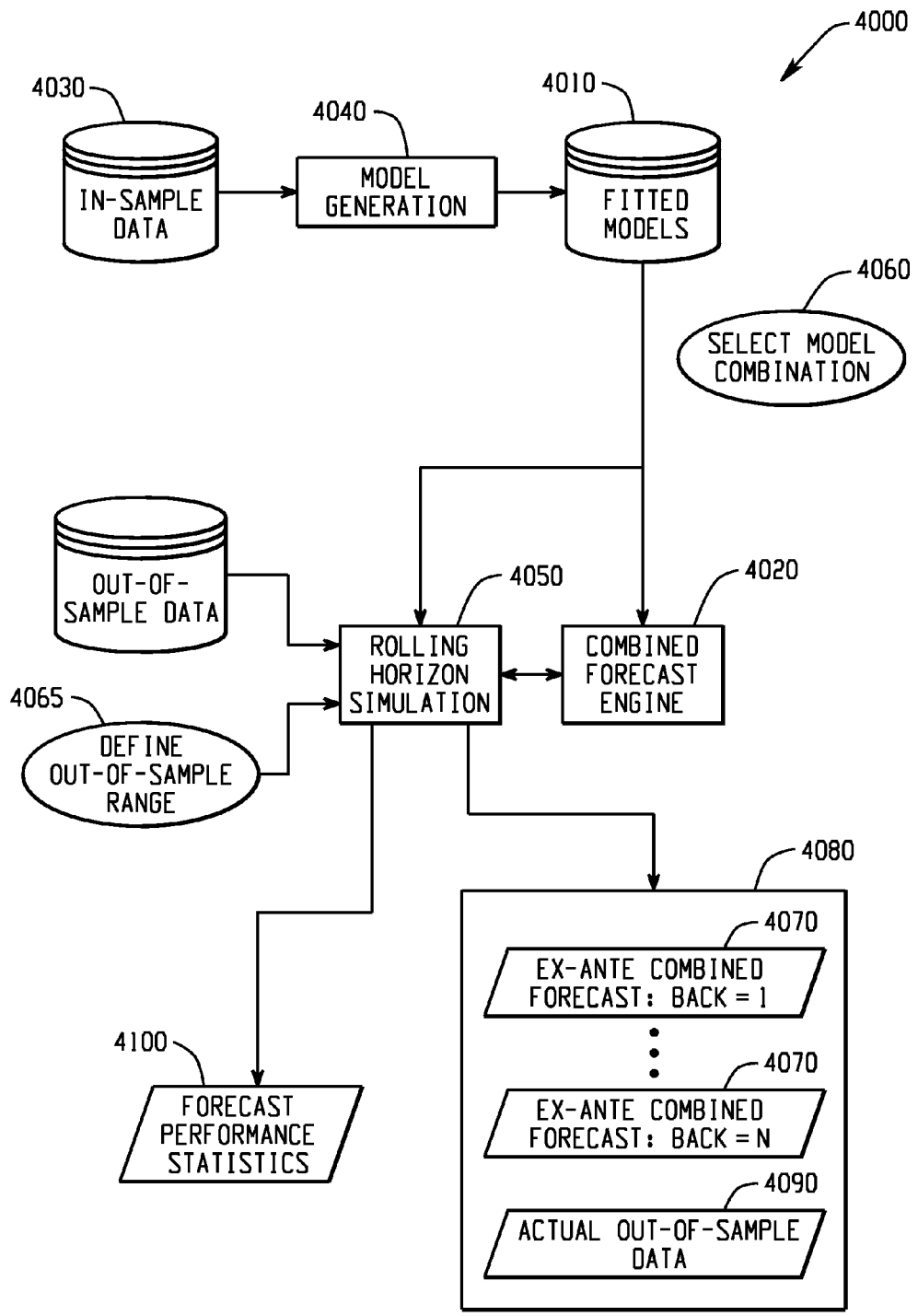
FIG. 34 is a block diagram depicting an example system for evaluating the performance of a combined forecast model using a rolling simulation analysis.

FIG. 34 is a block diagram depicting an example system 4000 for evaluating the performance of a combined forecast model using a rolling simulation analysis. The combined forecast model may be generated from a plurality of individual forecast models 4010 using a combined forecast engine 4020, for example using one or more of the systems and methods described above with reference to FIGS. 1-33. The plurality of forecast models 4010 may, for example, be generated based on sampled time-series data 4030 using a hierarchical time series forecasting system 4040, such as the Forecast Studio and Forecast Server software sold by SAS Institute Inc. of Cary, N.C.

The example system 4000 includes a rolling simulation engine 4050 that works in combination with the combined forecast engine 4020 to select a model combination 4060 and evaluate its performance over an out-of-sample range 4065. For instance, the rolling simulation engine 4050 and/or the combined forecast engine 4020 may present a user interface to select two or more of the individual forecast models 4010 for use in generating a combined forecast. In addition, a user interface may be provided by the rolling simulation engine 4050 to define the out-of-sample range 4065 (e.g., BACK=) over which the combined forecast is to be evaluated. The combined forecast is then repeated over the entire out-of-sample range, e.g., over the range of BACK=0 to a specified "back" value. The resulting ex-post forecasts 4070 (e.g., the forecasts for each BACK=value in the out-of-sample range) may then be displayed on a user interface 4080 along with the actual out-of-sample data 4090, such that the ex-post forecasts may be visually compared with the actual out-of-sample data over the specified period. In certain embodiments, the rolling simulation engine 4050 may also be used to simulate and display ex-ante forecasts for the combined model over a rolling simulation horizon (e.g., LEAD=value).

The rolling simulation engine 4050 may also calculate one or more performance statistics 4100 based on statistical comparisons of the actual out-of-sample data and the ex-post forecasts over the specified out-of-sample period 4065. The performance statistics 4100 may, for example, be displayed on a different tab of the user interface 4080. The performance statistics 4100 may include statistics that provide an indication of the average error between the forecast 4070 and the actual out-of-sample data 4090, such as mean, mean absolute percentage error (MAPE), mean absolute error (MAE), median absolute deviation (MAD) and/or MAD/Mean ratio calculations. Because these statistics indicate average errors between the actual and forecasted data, a low variance for the statistics over different out-of-sample ranges (e.g., different BACK=values) may provide an indication that the combined model is forecasting with required accuracy. On the other hand, a high variation in the forecast performance statistics 4100 over an out-of-sample range may indicate that the combined model is not performing at the required accuracy and may therefore result in larger errors when used over a wider horizon.

In certain embodiments, the rolling simulation engine 4050 and/or the combined forecast engine 4020 may be further configured to dynamically adjust one or more characteristics of the combined model based on the forecast horizon. For instance, the combined model list may be re-run for each (BACK, LEAD) pair such that the set of model candidates included in the combination can change from one pair of (BACK, LEAD) values to the next depending on how the combined forecast list is defined. For example, certain forecast quality tests, such as an encompassing test can be specified. An encompassing test examines forecasts produced by the component models of a combined model to determine whether the forecasts produced by one or more of the component models that make up the combined model are redundant when processing given data. For each (BACK, LEAD) pair, an encompassing test may be performed on the combined model based on the out-of-sample input data to be provided to the combined model for that (BACK, LEAD) pair. Should one or more of the component models be found to be redundant, those component models can be omitted from the combined model for that (BACK, LEAD) pair, with the weightings of the component models of the combined model being automatically adjusted accordingly. Component models can be dropped for other quality reasons as well, such as the inability or ineffectiveness of those component models in handling missing values present in the candidate model forecast's historical period and/or its horizon for a particular (BACK, LEAD) pair. In addition, component models may be dropped if the chosen method of weight estimation fails to produce a valid weight estimate for that model's forecast. Component model weights may also adaptively rescale over the span of the (BACK, LEAD) period to account for candidate models with missing values in their forecasts.

Figure 35:
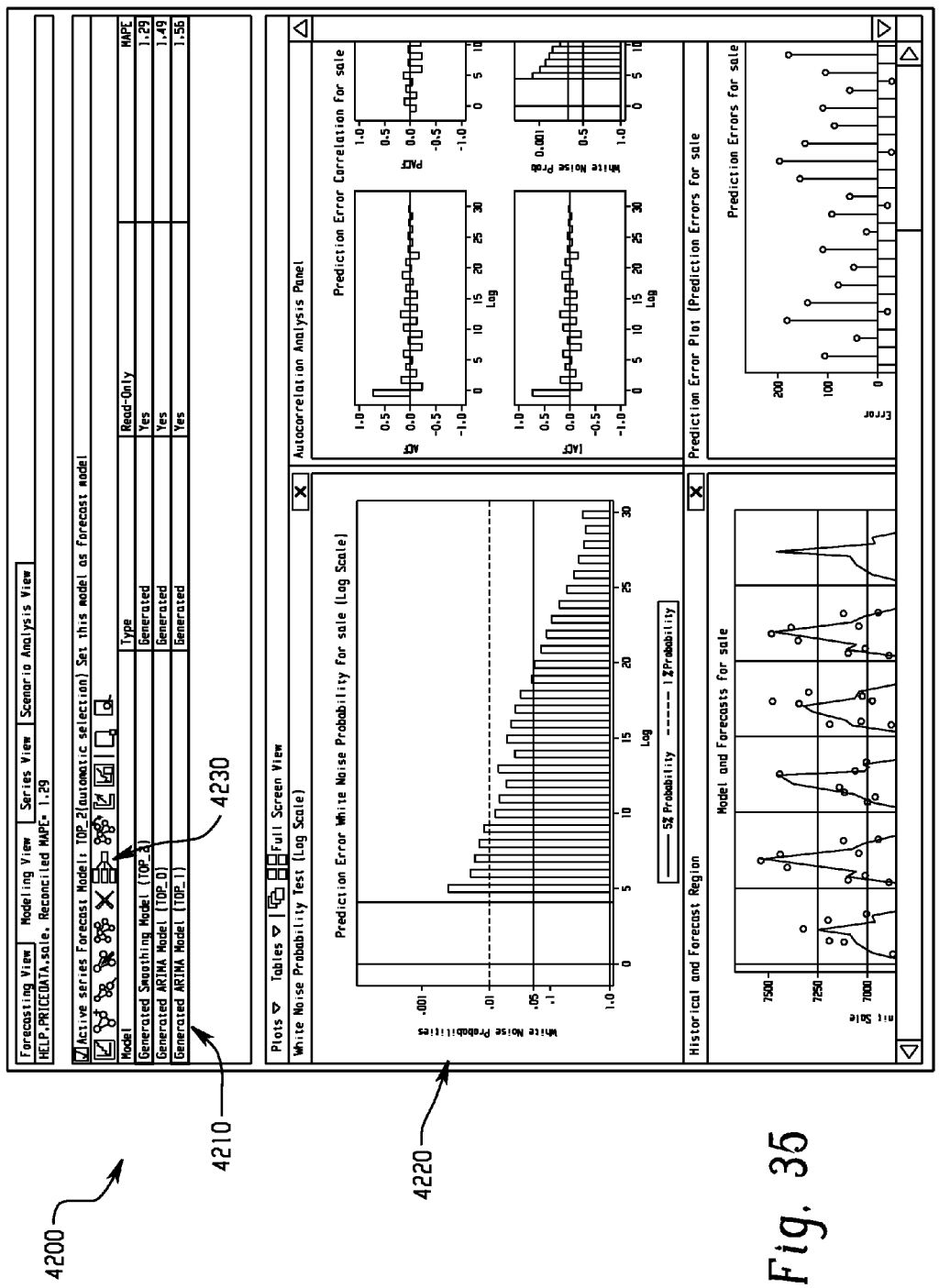
FIGS. 35-41 depict example user interfaces for evaluating the performance of a combined forecast model using a rolling simulation analysis.

An example operation of the system 4000 of FIG. 34 is further detailed with reference to the exemplary screen shots set forth in FIGS. 35-41. With reference first to FIG. 35, this figure illustrates an example interface 4200 which may be generated to select a model or model combination for the rolling simulation analysis. The interface 4200 includes a model selection region 4210 that lists the fitted individual models that are available for analysis. The interface 4200 may also include a forecast summary region 4220 that displays forecast data and/or other information relating to a selected one of the fitted models listed in the selection region 4210. In order to specify a combined model for evaluation, the interface 4200 may enable the user to highlight two or more of the individual models from the selection region 4210 and then select a combine models icon 4230. Selecting the combine model icon 4230 may cause a combine models interface to be displayed, for example in a pop-up window, as illustrated in FIG. 36.

Figure 36:
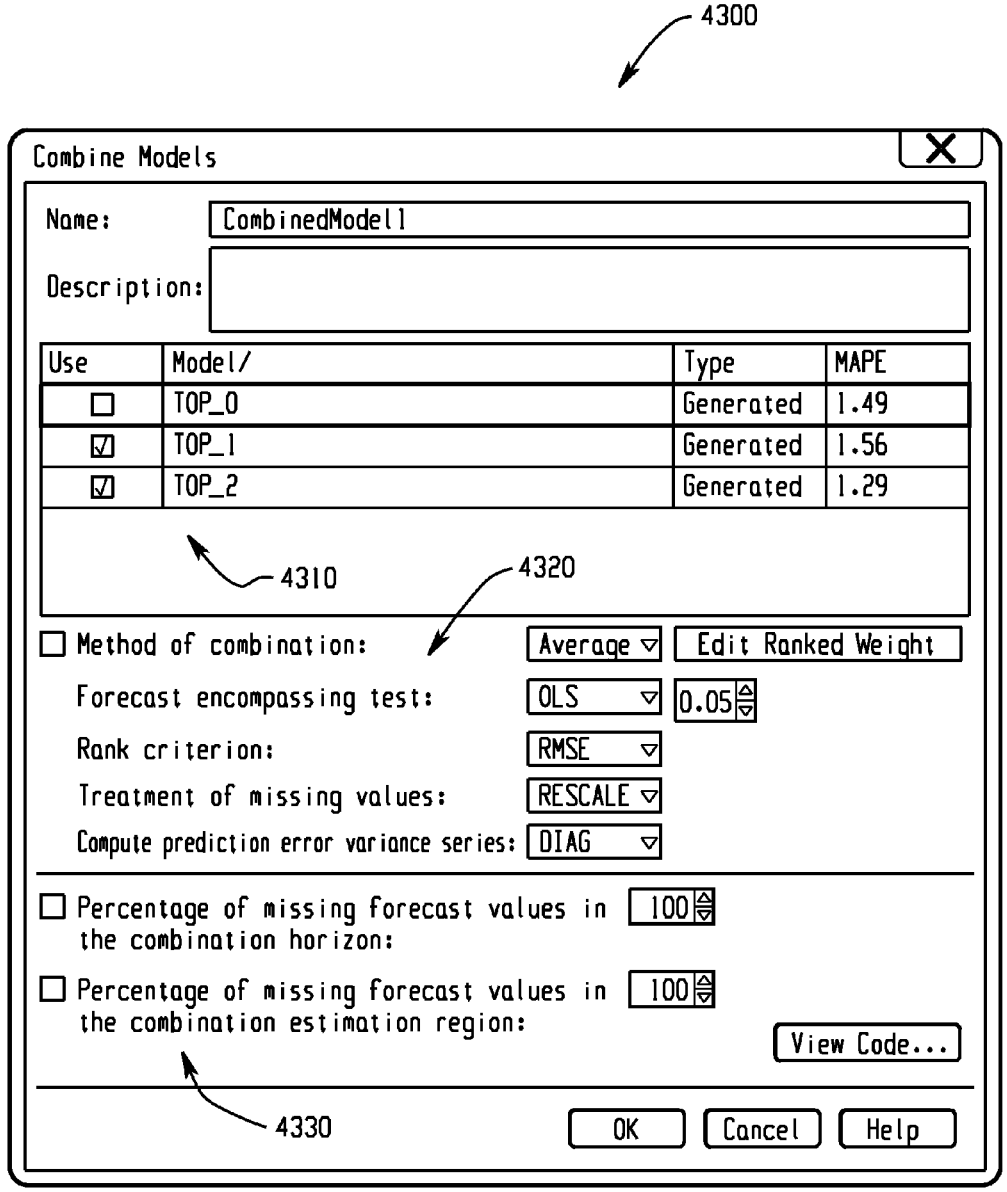

FIG. 36 depicts an example of an interface 4300 which may be generated to define the characteristics of a combined model for the rolling simulation analysis. The interface 4300 includes a model selection region 4310 for selecting the individual models for combination. As illustrated, the model selection region 4310 may list the model names along with one or more characteristics of the model, such as the model type and a model performance statistic (e.g., MAPE). In the illustrated example, two models (TOP_1 and TOP_2) are selected for combination.

The model combination interface 4300 provides a plurality of user-editable fields 4320 for defining the characteristics of the combined model. For instance, the user-editable fields 4320 may include a field for defining the model combination method (e.g., average or specify weights), a field for editing any specific weights applied to each individual model, a field to define how the combined model will treat missing values, and/or other fields for defining the characteristics of the combined model. In addition, the interface 4300 may further include fields 4330 that may be used to define the percentage of missing forecast values in the combination horizon and the percentage of missing forecast values in the combination estimation region. The interface 4300 may also provide regions for naming the combined model and providing a model description.

Figure 37:
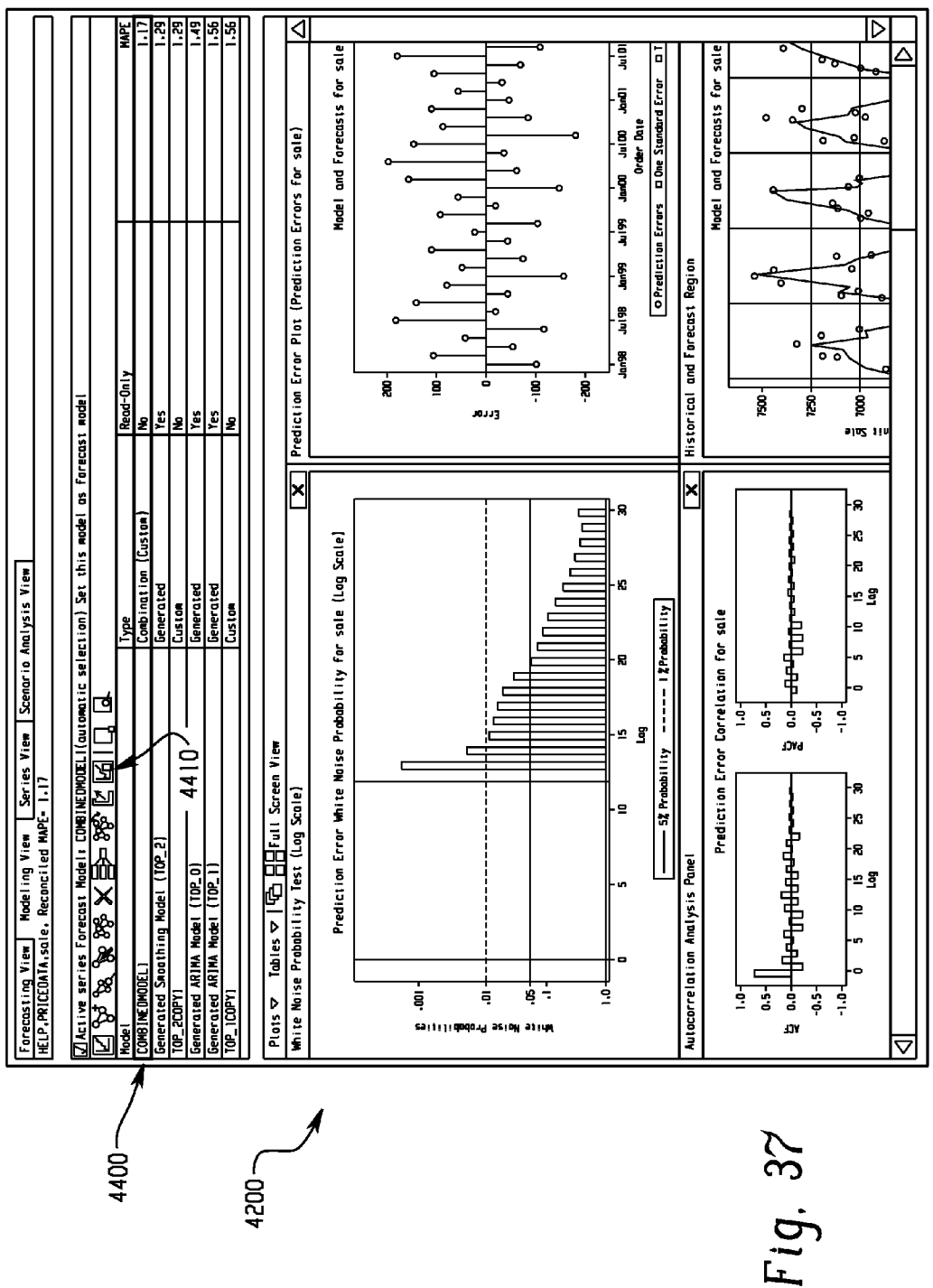

As illustrated in FIG. 37, once the characteristics of the combined model have been established using the model combination interface, the model selection interface is updated to list the newly defined combined model 4400. The combined model 4400 may then be selected for rolling simulation analysis, as shown in FIG. 37. The rolling simulation analysis may, for example, be executed on the selected combined model 4400 by selecting a rolling simulation icon 4410 on the interface 4200.

Figure 38:
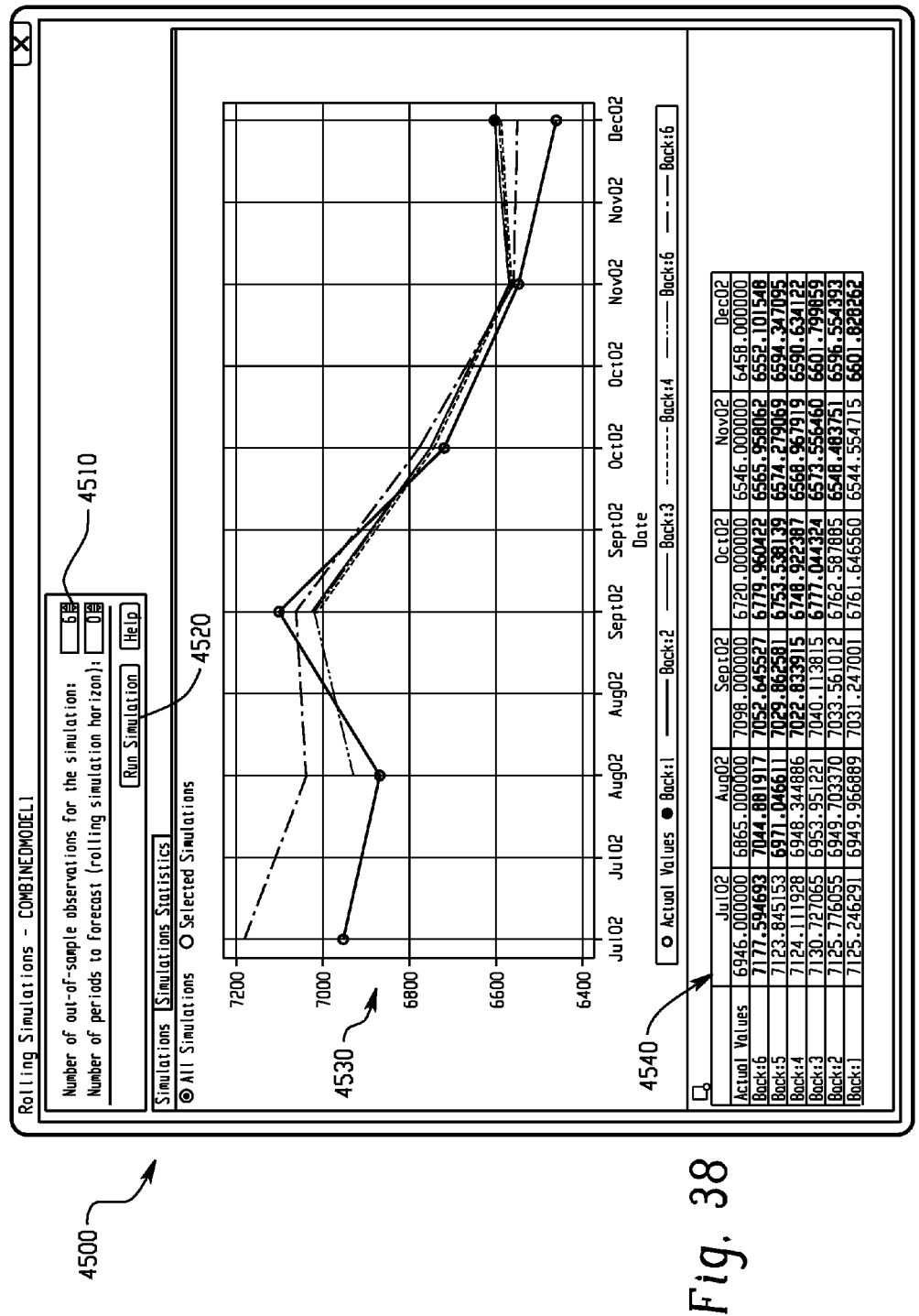

FIG. 38 depicts an example rolling simulation interface 4500 that may be displayed upon executing a rolling simulation analysis on a selected combined model. The interface 4500 includes a user-editable region 4510 for defining the number of out-of-sample observations (e.g., the number of BACK=values) to be included in the simulation. Upon selecting a number of out-of-sample observations, the user may begin the simulation, for example by selecting a Run Simulation icon 4520. In the illustrated example, a simulation has been executed after selecting 6 out-of-sample observations. The rolling simulation engine then simulates an ex-post forecast for each of out-of-sample observation (e.g., for each BACK=value 1-6), and plots the resulting forecasts on a display region 4530 of the interface 4500 along with the actual out-of-sample values. In this way, the rolling simulation interface 4500 enables the user to graphically view the predictions of the combined model at various forecast origins and compare the predictions to the actual out-of-sample data values.

For instance, in the illustrated example, six ex ante ex post forecasts (BACK:1 through BACK:6) are plotted in the display region 4530 for comparison with the actual out-of-sample data values. Specifically, in the first out-of-sample observation (BACK:1) the combined forecast is generated one period into the past (Dec. 02), in the next out-of-sample observation (BACK:2) the combined forecast is generated two periods into the past (Dec. 02 thru Nov. 02), and so on through the sixth out-of-sample observation (BACK:6).

In addition, for further comparison, the rolling simulation interface 4500 of FIG. 38 also includes a numerical display region 4540 that displays the forecast values for each out-of-sample observation (BACK:1 thru BACK:6) along with the actual values of the out-of-sample data. The forecasted values in the illustrated example are set forth in the numerical display region 4540 in bold text.

In certain embodiments, the rolling simulation engine may calculate an optimal number of out-of-sample observations to automatically populate the interface field 4510 with a back range default value. The default value for the back range field 4510 may, for example, be calculated using the following formula:

Default=min(lead,min(min(max(seasonality,4),52),
    min(*t*−6,max((int)(0.1\**t*),1))))

where:
lead—lead option value
T—length of series
S—length of seasonality
Minimum value of BackRange is: Minimum=1
Maximum value of BackRange is: Maximum=(T minus 6)

defaultBackRange=Math.min(lead,Math.min(Math.
    min(Math.max(seasonality,4),52),Math.min(*t*−6,
    Math.max((int)(0.1\**t*),1))))

Figure 39:
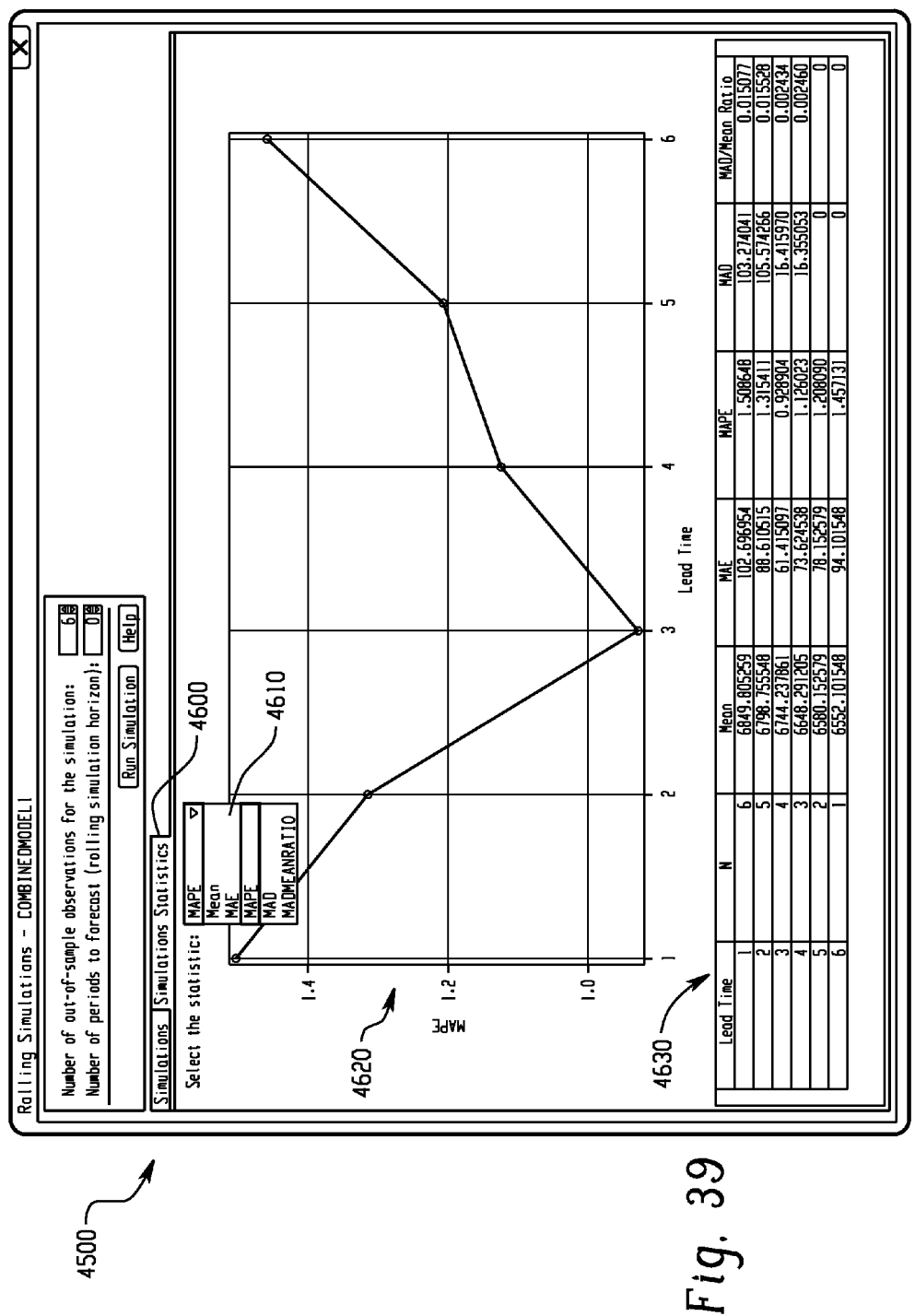

As illustrated in FIG. 39, the rolling simulation interface 4500 may also include one or more fields for use in generating and displaying one or more forecast performance statistics. The simulation statistics fields may, for example, be included in a separate tab 4600 of the rolling simulation interface 4500, as illustrated in FIG. 39. The simulation statistics tab 4600 includes a field 4610 for selecting a particular forecast performance statistic for identifying the error between the forecasted values and the actual out-of-sample values, such as a Mean, MAE, MAPE, MAD or MAD/Mean ratio calculation. A graph of the selected performance statistic at each lead time is displayed in a display region 4620 of the interface.

In addition, the simulation statistics tab 4600 may also include a numerical display region 4630 that displays the performance statistic values for each lead time. In the illustrated example, the numerical display region 4630 includes values for a plurality of different performance statistics calculated by the rolling simulation engine. In this way, the user may simultaneously view the values for multiple performance statistics for the combined model in the numerical display region 4630, and select a particular one of the performance statistic for graphical display 4620.

The graph 4620 and numerical display 4630 in the example illustrated in FIG. 39 show the performance error in terms of the lead time of the ex post forecast. For illustration, let $$\hat{e}_{t-b+l|t-b}^{(m)} = y_{t-b+l} - \hat{y}_{t-b+l|t-b}^{(m)}$$

represent the multi-step-ahead prediction error for the time (t−b+l)th period and for the mth time series model for b=1, . . . , B and l=1, . . . , b, where b is the holdback index and l is the lead index. The holdback index, b, rolls the forecast origin forward in time. For each holdback index, b=1, . . . , B, multi-step-ahead prediction errors are computed for each lead index, l=1, . . . , b. By gathering the prediction errors by the lead index, l, for all holdback indices, b=1, . . . , B, forecast performance can be evaluated by lead time. In other words, a model's l-step-ahead forecast performance can be evaluated across various forecast origins.

Figure 40:
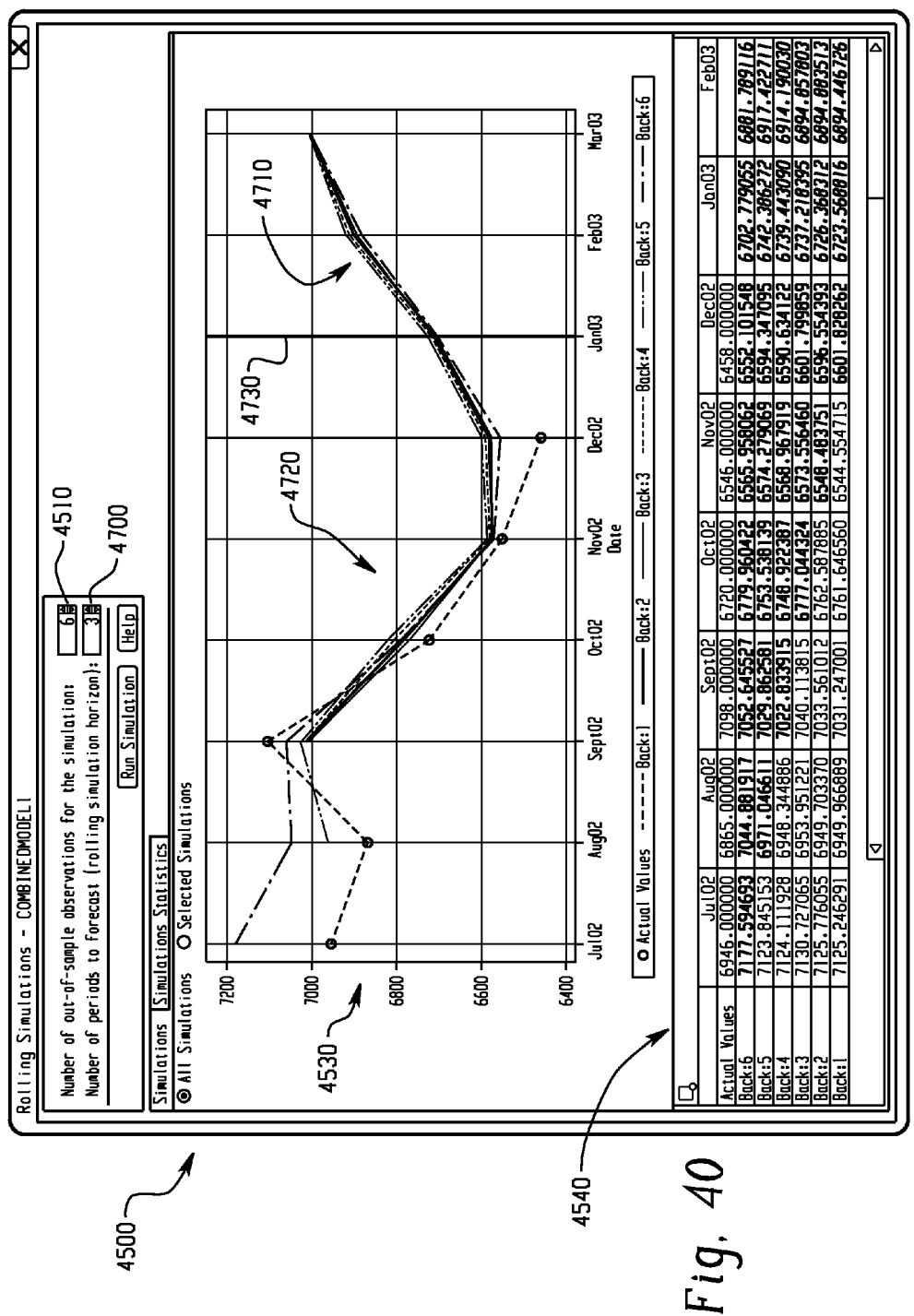

With reference again to the simulation tab of the interface 4500, FIG. 40 illustrates the further ability of the rolling simulation engine to generate ex-ante (i.e., forward-looking) forecasts for the combined model. The example interface 4500 includes a user input region 4700 to select the desired number of periods to forecast. When a simulation is executed with both the number of out-of-sample observations 4510 and a number of forecast periods 4700 selected, the rolling simulation engine generates both ex-ante and ex-post forecasts for each of the out-of-sample observations. The forecasts for each out-of-sample observation are plotted along with the actual out-of-sample data in the graphical display region 4530 of the interface 4500. A vertical line 4730 separates the ex-post forecasts 4720 (to the left of the line) from the ex-ante 4710 forecasts (to the right of the line.) Of course, actual out-of-sample data values are displayed only for past periods in which data has been recorded, which is why there are no actual out-of-sample values to the right of the vertical line 4730 in the illustrated example.

In addition, for further comparison, the example interface 4500 also includes numerical values for both the ex-ante and ex-post forecasts in the numerical display region 4540, along with the actual out-of-sample data values. The ex-ante and ex-post forecasted values in the illustrated example are set forth in the numerical display region 4540 in bold text.

Figure 41:
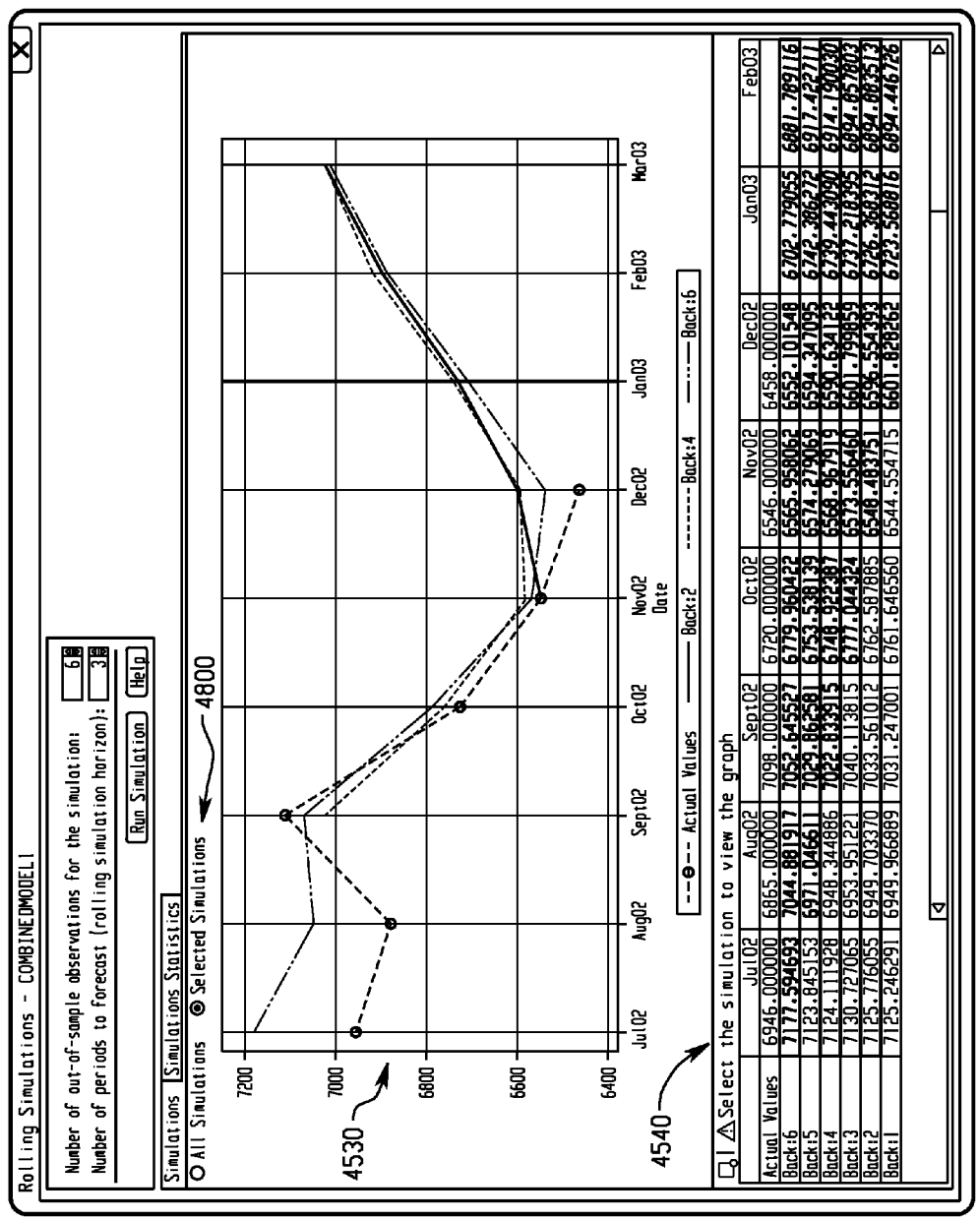

FIG. 41 illustrates an example of how the graphical display on the simulation interface 4500 may be modified to compare specific out-of-sample observations. In the illustrated example, the interface includes user input fields 4800 for selecting either all of the simulations or select simulations for display. If the "select simulations" field is selected, then the interface 4500 only displays the forecasts for out-of-sample observations that are selected in the numerical display region 4540. In the illustrated example, the Back:2, Back:4 and Back: 6 observations have been selected, and therefore only these three forecasts are displayed in the graphical display region 4530 along with the actual out-of-sample values.

The methods and systems described herein may be implemented on many different types of processing devices by program code comprising program instructions that are executable by the device processing subsystem. The software program instructions may include source code, object code, machine code, or any other stored data that is operable to cause a processing system to perform the methods and operations described herein. Other implementations may also be used, however, such as firmware or even appropriately designed hardware configured to carry out the methods and systems described herein.

The systems' and methods' data (e.g., associations, mappings, data input, data output, intermediate data results, final data results, etc.) may be stored and implemented in one or more different types of computer-implemented data stores, such as different types of storage devices and programming constructs (e.g., RAM, ROM, Flash memory, flat files, databases, programming data structures, programming variables, IF-THEN (or similar type) statement constructs, etc.). It is noted that data structures describe formats for use in organizing and storing data in databases, programs, memory, or other computer-readable media for use by a computer program.

The computer components, software modules, functions, data stores and data structures described herein may be connected directly or indirectly to each other in order to allow the flow of data needed for their operations. It is also noted that a module or processor includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Further, as used in the description herein and throughout the claims that follow, the meaning of "each" does not require "each and every" unless the context clearly dictates otherwise. Finally, as used in the description herein and throughout the claims that follow, the meanings of "and" and "or" include both the conjunctive and disjunctive and may be used interchangeably unless the context expressly dictates otherwise; the phrase "exclusive or" may be used to indicate situation where only the disjunctive meaning may apply.

It is claimed:

1. A computer-program product tangibly embodied in a non-transitory, machine-readable storage medium having instructions stored thereon, the instructions operable to cause a data processing apparatus to perform operations including:
    displaying representations of multiple models operable to provide ex-post forecasts and ex-ante forecasts with regard to a forecast variable;
    accessing an input that represents a selection of at least two of the models;
    accessing a historical time series that includes multiple historical observations of the forecast variable;
    defining multiple distinct holdout time series within the historical time series, wherein each of the holdout time series includes a portion of the historical observations of the forecast variable and spans a corresponding time period;
    generating a combination model by combining the selected models;
    evaluating multi-step forecasting characteristics of the combination model by using ex-post forecasting at multiple different points of origin, wherein evaluating includes, with respect to each of the time periods, performing operations including:
        using the combination model to generate ex-post forecasted values of the forecast variable at multiple times during the time period;
        comparing the ex-post forecasted values to coinciding historical observations included in the holdout time series that spans the time period;
        calculating ex-post forecast errors based on the comparison; and
        displaying the ex-post forecast errors.

2. The computer-program product of claim 1, wherein the ex-post forecast errors calculated with respect to each of the time periods are displayed with reference to the time periods spanned by the respective holdout time series.

3. The computer-program product of claim 1, wherein each of the time periods differs in duration from every other one of the time periods.

4. The computer-program product of claim 1, wherein the operations further include:
    displaying an indication of multiple selectable holdout time series durations; and
    receiving an input that represents a selection of at least two of the holdout time series durations, wherein the multiple holdout time series are defined based on the selected holdout time series durations.

5. The computer-program product of claim 1, wherein comparing the ex-post forecasted values to coinciding historical observations includes displaying the ex-post forecasted values and the coinciding historical observations on a same graph.

6. The computer-program product of claim 5, further comprising:
    using the combination model to generate an ex-ante forecast of the forecasting variable, wherein the ex-ante forecast includes forecasted values of the forecasting variable with respect to at least one future time or future time period.

7. The computer-program product of claim 6, wherein the operations further include:
    receiving an input representing an ex-ante forecasting step-ahead parameter, wherein generating the ex-ante forecast further includes setting a step-ahead time of the ex-ante forecast based on the input.

8. The computer-program product of claim 1, wherein defining multiple holdout time series within the historical time series is done such that no two of the time periods begin at a same time.

9. A method comprising:
    displaying representations of multiple models operable to provide ex-post forecasts and ex-ante forecasts with regard to a forecast variable;
    accessing an input that represents a selection of at least two of the models;
    accessing a historical time series that includes multiple historical observations of the forecast variable;
    defining multiple distinct holdout time series within the historical time series, wherein each of the holdout time series includes a portion of the historical observations of the forecast variable and spans a corresponding time period;

generating a combination model by combining the selected models;

evaluating multi-step forecasting characteristics of the combination model by using ex-post forecasting at multiple different points of origin, wherein evaluating includes, with respect to each of the time periods, performing operations including:

using the combination model to generate ex-post forecasted values of the forecast variable at multiple times during the time period;

comparing the ex-post forecasted values to coinciding historical observations included in the holdout time series that spans the time period;

calculating ex-post forecast errors based on the comparison; and displaying the ex-post forecast errors.

10. The method of claim 9, wherein the ex-post forecast errors calculated with respect to each of the time periods are displayed with reference to the time periods spanned by the respective holdout time series.

11. The method of claim 9, wherein each of the time periods differs in duration from every other one of the time periods.

12. The method of claim 9, further comprising:

displaying an indication of multiple selectable holdout time series durations; and receiving an input that represents a selection of at least two of the holdout time series durations, wherein the multiple holdout time series are defined based on the selected holdout time series durations.

13. The method of claim 9, wherein comparing the ex-post forecasted values to coinciding historical observations includes displaying the ex-post forecasted values and the coinciding historical observations on a same graph.

14. The method of claim 13, further comprising:

using the combination model to generate an ex-ante forecast of the forecasting variable, wherein the ex-ante forecast includes forecasted values of the forecasting variable with respect to at least one future time or future time period.

15. The method of claim 14, further comprising:

receiving an input representing an ex-ante forecasting step-ahead parameter, wherein generating the ex-ante forecast further includes setting a step-ahead time of the ex-ante forecast based on the input.

16. The method of claim 9, wherein defining multiple holdout time series within the historical time series is done such that no two of the time periods begin at a same time.

17. A computerized system comprising:

a processor configured to perform operations including:

displaying representations of multiple models operable to provide ex-post forecasts and ex-ante forecasts with regard to a forecast variable;

accessing an input that represents a selection of at least two of the models;

accessing a historical time series that includes multiple historical observations of the forecast variable;

defining multiple distinct holdout time series within the historical time series, wherein each of the holdout time series includes a portion of the historical observations of the forecast variable and spans a corresponding time period;

generating a combination model by combining the selected models;

evaluating multi-step forecasting characteristics of the combination model by using ex-post forecasting at multiple different points of origin, wherein evaluating includes, with respect to each of the time periods, performing operations including:

using the combination model to generate ex-post forecasted values of the forecast variable at multiple times during the time period;

comparing the ex-post forecasted values to coinciding historical observations included in the holdout time series that spans the time period;

calculating ex-post forecast errors based on the comparison; and displaying the ex-post forecast errors.

18. The system of claim 17, wherein the ex-post forecast errors calculated with respect to each of the time periods are displayed with reference to the time periods spanned by the respective holdout time series.

19. The system of claim 17, wherein each of the time periods differs in duration from every other one of the time periods.

20. The system of claim 17, wherein the operations further include:

displaying an indication of multiple selectable holdout time series durations; and receiving an input that represents a selection of at least two of the holdout time series durations, wherein the multiple holdout time series are defined based on the selected holdout time series durations.

21. The system of claim 17, wherein comparing the ex-post forecasted values to coinciding historical observations includes displaying the ex-post forecasted values and the coinciding historical observations on a same graph.

22. The system of claim 21, wherein the operations further include: using the combination model to generate an ex-ante forecast of the forecasting variable, wherein the ex-ante forecast includes forecasted values of the forecasting variable with respect to at least one future time or future time period.

23. The system of claim 22, wherein the operations further include: receiving an input representing an ex-ante forecasting step-ahead parameter, wherein generating the ex-ante forecast further includes setting a step-ahead time of the ex-ante forecast based on the input.

24. The system of claim 17, wherein defining multiple holdout time series within the historical time series is done such that no two of the time periods begin at a same time.

* * * * *